US008263746B2

(12) United States Patent
Tesar et al.

(10) Patent No.: US 8,263,746 B2
(45) Date of Patent: *Sep. 11, 2012

(54) ANTI-CD38 HUMAN ANTIBODIES AND USES THEREOF

(75) Inventors: Michael Tesar, Weilheim (DE); Ute Jager, Munich (DE)

(73) Assignee: Morphosys AG, Martinsried/Planegg (DE)

( * ) Notice: Subject to any disclaimer, the term of this patent is extended or adjusted under 35 U.S.C. 154(b) by 1084 days.

This patent is subject to a terminal disclaimer.

(21) Appl. No.: 10/588,568

(22) PCT Filed: Feb. 7, 2005

(86) PCT No.: PCT/IB2005/002476

§ 371 (c)(1),
(2), (4) Date: Oct. 14, 2009

(87) PCT Pub. No.: WO2005/103083

PCT Pub. Date: Nov. 3, 2005

(65) Prior Publication Data

US 2011/0268726 A9    Nov. 3, 2011

Related U.S. Application Data

(60) Provisional application No. 60/541,911, filed on Feb. 6, 2004, provisional application No. 60/547,584, filed on Feb. 26, 2004, provisional application No. 60/553,948, filed on Mar. 18, 2004, provisional application No. 60/599,014, filed on Aug. 6, 2004, provisional application No. 60/614,471, filed on Oct. 1, 2004.

(51) Int. Cl.
*C07K 16/00* (2006.01)
*C12P 21/08* (2006.01)
*A61K 39/395* (2006.01)
*A61K 39/00* (2006.01)

(52) U.S. Cl. ............. 530/387.9; 530/387.1; 530/388.15; 530/388.23; 530/389.6; 424/130.1; 424/139.1; 424/142.1; 424/158.1

(58) Field of Classification Search ........................ None
See application file for complete search history.

(56) References Cited

U.S. PATENT DOCUMENTS

| 5,545,405 | A  | 8/1996  | Page |
| 7,084,257 | B2 | 8/2006  | Deshpande et al. |
| 7,091,323 | B2 | 8/2006  | Pan et al. |
| 7,223,397 | B1 | 5/2007  | Rosenblum et al. |
| 7,262,278 | B2 | 8/2007  | Tawara et al. |
| 7,794,719 | B2 | 9/2010  | Bardroff et al. |
| 2002/0164788 | A1 | 11/2002 | Ellis et al. |
| 2003/0211553 | A1 | 11/2003 | Logtenberg et al. |
| 2004/0141982 | A1 | 7/2004  | Lust et al. |
| 2010/0172907 | A1 | 7/2010  | Bardroff et al. |

FOREIGN PATENT DOCUMENTS

| AU | 8267501 A | 1/2002 |
| EP | 1 174 440 A | 1/2002 |
| EP | 1720907 A2 | 11/2006 |
| WO | WO 94/17184 | 8/1994 |
| WO | WO 96/16990 A | 6/1996 |
| WO | WO 99/62526 | 12/1999 |
| WO | WO 00/40265 | 7/2000 |
| WO | WO 00/48361 | 8/2000 |
| WO | WO 00/48631 A2 | 8/2000 |
| WO | WO 01/05950 A2 | 1/2001 |
| WO | WO 02/06347 A | 1/2002 |
| WO | WO 02/06347 A1 | 1/2002 |
| WO | WO 02/32288 | 4/2002 |
| WO | WO 03/070760 A2 | 8/2003 |
| WO | WO 2004/003019 A2 | 1/2004 |
| WO | WO 2005/042019 | 5/2005 |
| WO | WO 2005/087806 | 9/2005 |
| WO | WO 2005103083 A2 | 11/2005 |
| WO | WO 2006/088951 A2 | 8/2006 |
| WO | WO 2006/099875 | 9/2006 |
| WO | WO 2006/110581 | 10/2006 |
| WO | WO 2006125640 A | 11/2006 |

OTHER PUBLICATIONS

Skolnick and Fetrow. From genes to protein structure and function: novel applications of computational approaches in the genomic era. Trends in Biotechnology, 2000. vol. 18, pp. 34-39.*
Burgess, Shaheen, Ravera, Jaye, Donohue, and Winkles. Possible dissociation of the heparin-binding and mitogenic activities of heparin-binding (acidic fibroblast) growth factor-1 from its receptor binding activities by site directed mutagenesis of a single lysine residue. Journal of Cell Biology, 1990. vol. 111, pp. 2129-2138.*
Lazar, Watanabe, Dalton, and Sporn. Transforming growth factor alpha: mutation of aspartic acid 47 and leucine 48 results in different biological activities. Molecular and Cellular Biology, 1988. vol. 8, pp. 1247-1252.*
Rudikoff, Giusti, Cook, and Scharff. Single amino acid substitution altering antigen binding specificity. Proceedings of the National Academy of Sciences, 1982. vol. 79, pp. 1979-1983.*
Kretzschmar et al., "Antibody discovery: phage display," Current Opinion in Biotechnology, 2002, 13:598-602.
Antonelli, et al.,"Human anti-CD38 autoantibodies raise intracellular calcium.."; Diabetes (2001) vol. 50; pp. 985-991.
Ausiello, et al.,"Functional topography of discrete domains of human CD38"; Tissue Antigens, (2000); vol. 56(6); pp. 539-547.

(Continued)

*Primary Examiner* — Anne M. Gussow
(74) *Attorney, Agent, or Firm* — Foley & Lardner LLP

(57) ABSTRACT

The present invention provides recombinant antigen-binding regions and antibodies and functional fragments containing such antigen-binding regions that are specific for CD38, which plays an integral role in various disorders or conditions. These antibodies, accordingly, can be used to treat, for example, hematological malignancies such as multiple myeloma. Antibodies of the invention also can be used in the diagnostics field, as well as for investigating the role of CD38 in the progression of disorders associated with malignancies. The invention also provides nucleic acid sequences encoding the foregoing antibodies, vectors containing the same, pharmaceutical compositions and kits with instructions for use. The invention also provides isolated novel epitopes of CD38 and methods of use therefore.

28 Claims, 24 Drawing Sheets

OTHER PUBLICATIONS

Bollen P., et al.,"The Goettingen Minipig in pharmacology and toxicology"; Pharmacology and Toxicology, (1997); vol. 80; pp. 3-4; XP009075772; ISSN 0901-9928.

Chamow, et al.,"Humanized, bispecific immunoadhesin-antibody that retargets"; J Immunol. (1994); vol. 1;153(9); pp. 4268-4280.

Deshpande Deepak, et al.,"Cloning and functional characterization of cDNA"; Faseb Journal; (2004); vol. 18, No. 4-5,; pp Abstr. 842.4 URL-http://ww. XP009075817; ISSN 0892-6638.

Ellis, J., et al.,"Enginerred anti-CD38 monoclonal antibodies for immunotherapy of multiple myeloma"; Journal of Immunology; (1995); vol. 155, No. 2; pp. 925-937; XP002146232.

Ferrero E., et al.,"Characterization and phylogenetic epitope mapping.."; BMC Immunology; (2004); vol. 5; pp. 2004-2009; XP002410155 ISSN: 1471-2172.

Flavell, D., et al.,"Therapy of human T-cell acute lymphoblastic leukaemia"; Br. J. Cancer; (2001); vol. 84; pp. 571-578.

Funaro, A., et al.,"Involvement of the multilineage CD38 molecule . . . " J. Immunol.; (1990); vol. 145; pp. 2390-2396.

Knappik., et al.,"Fully synthetic human combinatorial antibody libraries (HuCAL) based on modular.."; J Mol Biol (2000); 296; pp. 57-86.

Krebs, B., et al.,"High-throughput generation and engineering . . . "; J Immunol Methods (2001); vol. 254; pp. 67-84.

Lohning, C., et al.,"Novel methods for displaying (poly) peptides/ proteins on bacteriophage.." (2001); WO 01/05950.

Malavasi, F., et al.,"Characterization of a murine monoclonal antibody.."; Hum. Immunol. (1984); vol. 9; pp. 9-20.

Maloney D., et al.,"Antibody therapy for treatment of multiple myeloma"; Seminars in Hematology, (Jan. 1999); pp. 30-33; XP000857401 ISSN: 0037-1963.

Mehta, K., et al.,"Retinoic acid-induced CD38 antigen as a target for immunotoxin.."; Mol Cancer Ther (2004); vol. 3; pp. 345-352.

Namba, M., et al.;"Establishment of five human myeloma cell lines"; In vitro Cell Dev. Biol; (1989) vol. 25; pp. 723.

Nata, K., et al.,"Human gene encoding CD38 (ADP-ribosyl cyclase/ cyclic ADP-ribose hydrolase)"; Gene (1997); vol. 186, No. 2; pp. 285-292.

Stevenson F. K., et al."Preliminary Studies of an Immunotherapy Approach.."; Blood, W.B. Saunders (1991); vol. 77, No. 5; pp. 1071-1079; XP000930093; ISSN 006-4971.

Zhou, H., et al.,"Optimiziation of primer sequences for mouse scFv.."; Nucleic Acids Res. (1994); vol. 22; pp. 888-889.

Zocchi E., et al.,"A single protein immunologically identified as CD38.."; Biochemical and Biophysical Rsrch Comm. (1993); vol. 196, No. 3; pp. 1459-1465; XP 002410154 ISSN 0006.

Third International Workshop on Human Leukocyte Differentiation Antigens, Oxford, England; Sep. 1986.

Brorson et al., "Mutational Analysis of Avidity and Fine Specificity of Anti-Levan Antibodies," J. Immunol., 1999, 163:6694-6701.

Brummel et al., "Probing the combining site of an anti-carbohydrate antibody by saturation-mutagenesis: role of the heavy-chain CDR3 residues," Biochemistry, 1993, 32:1180-1187, PubMed abstract, 2 pages.

Burks et al., "In vitro scanning saturation mutagenesis of an antibody binding pocket," Proc. Natl. Acad. Sci. USA, Jan. 1997, 94:412-417.

Casset et al., "A peptide mimetic of an anti-CD4 monoclonal antibody by rational design," Biochemical and Biophysical Research Communications, 2003, 307:198-205.

U.S. Appl. No. 11/920,830, filed May 24, 2006, Tesar et al.

U.S. Appl. No. 12/089,806, filed Oct. 12, 2006, Tesar et al.

Chen et al., "Selection and Analysis of an Optimized Anti-VEGF Antibody: Crystal Structure of an Affinity-matured Fab in Complex with Antigen," J. Mol. Biol., 1999, 283:865-881.

Colman, P.M., "Effects of amino acid sequence changes on antibody-antigen interactions," Research in Immunol., 1994, 145:33-36.

DePascalis et al,. "Grafting of 'Abbreviated' Complementarity-Determining Regions Containing Specificity-Determining Residues Essential for Ligand Contact to Engineer a Less Immunogenic Humanized Monoclonal Antibody," J. Immunol., 2002, 169:3076-3084.

Dufner et al., "Harnessing phage and ribosome display for antibody optimization," Trends in Biotechnology, 2006, 24(11):523-529.

Holm et al., "Functional mapping and single chain construction of the anti-cytokeratin 8 monoclonal antibody TS1," Molecular Immunology, 2007, 44:1075-1084.

Jang et al., "The structural basis for DNA binding by an anti-DNA autoantibody," Molecular Immunology, 1998, 35:1207-1217.

Kobayashi et al., "Tryptophan H33 plays an important role in pyrimidine (6-4) pyrimidone photoproduct binding by a high-affinity antibody," Protein Engineering, 1999, 12(10):879-884.

Kumar et al., "Molecular Cloning and Expression of the Fabs of Human Autoantibodies in *Escherichia coli*," J. Biol. Chem., 2000, 275:35129-35136.

MacCallum et al., "Antibody-antigen Interactions: Contact Analysis and Binding Site Topography," J. Mol. Biol., 1996, 262:732-745.

Smith-Gill et al., "Contributions of Immunoglobulin Heavy and Light Chains to Antibody Specificity for Lysozyme and Two Haptens," J. Immunol., Oct. 15,1987, 139:4135-4144.

Song et al., "Light Chain of Natural Antibody Plays a Dominant Role in Protein Antigen Binding," Biochemical and Biophysical Research Communications, 2000, 268:390-394.

Vajdos et al., "Comprehensive Functional Maps of the Antigen-binding Site of an Anti-ErbB2 Antibody Obtained with Shotgun Scanning Mutagenesis," J. Mol. Biol., 2002, 320:415-428.

Ward et al., "Binding activities of a repertoire of single immunoglobulin variable domains secreted from *Escherichia coli*," Nature, 1989, 341:544-546.

Wu et al. "Humanization of a Murine Monoclonal Antibody by Simultaneous Optimization of Framework and CDR Residues," J. Mol. Biol., 1999, 294:151-162.

Hoshino et al. "Mapping of the Catalytic and Epitopic Sites of Human $CD38/NAD^+$ Glycohydrolase to a Functional Domain in the Carboxyl Terminus," J. Immunol., 1997, 158(2):741-747.

Jackson et al., "Isolation of a cDNA encoding the human CD38 (T10) molecule, a cell surface glycoprotein with an unusual discontinuous pattern of expression during lymphocyte differentiation," J. Immunol., Apr. 1, 1990, 144(7):2811-2815.

Konopleva et al., "Ligation of Cell Surface CD38 Protein with Agonistic Monoclonal Antibody Induces a Cell Growth Signal in Myeloid Leukemia Cells," J. Immunol., 1998, 161:4702-4708.

Marchetti et al., "Prolonged In Vitro Exposure to Autoantibodies Against CD38 Impairs the Function and Survival of Human Pancreatic Islets," Diabetes, Dec. 2002, 51(Supp.3):S474-S477.

\* cited by examiner

Figure 1a

Variable Heavy Chain DNA

3077_VH1B (SEQ ID NO: 1):

```
(1)   CAGGTGCAAT TGGTTCAGAG CGGCGCGGAA GTGAAAAAAC CGGGCGCGAG
(51)  CGTGAAAGTG AGCTGCAAAG CCTCCGGATA TACCTTTACT TCTTATTCTA
(101) TTAATTGGGT CCGCCAAGCC CCTGGGCAGG GTCTCGAGTG GATGGGCTAT
(151) ATCGATCCGA ATCGTGGCAA TACGAATTAC GCGCAGAAGT TTCAGGGCCG
(201) GGTGACCATG ACCCGTGATA CCAGCATTAG CACCGCGTAT ATGGAACTGA
(251) GCAGCCTGCG TAGCGAAGAT ACGGCCGTGT ATTATTGCGC GCGTGAGTAT
(301) ATTTATTTTA TTCATGGTAT GCTTGATTTT TGGGGCCAAG GCACCCTGGT
(351) GACGGTTAGC TCA
```

3079_VH3 (SEQ ID NO: 2):

```
(1)   CAGGTGCAAT TGGTGGAAAG CGGCGGCGGC CTGGTGCAAC CGGGCGGCAG
(51)  CCTGCGTCTG AGCTGCGCGG CCTCCGGATT TACCTTTTCT AATTATGGTA
(101) TGCATTGGGT GCGCCAAGCC CCTGGGAAGG GTCTCGAGTG GGTGAGCAAT
(151) ATCCGTTCTG ATGGTAGCTG GACCTATTAT GCGGATAGCG TGAAAGGCCG
(201) TTTTACCATT TCACGTGATA ATTCGAAAAA CACCCTGTAT CTGCAAATGA
(251) ACAGCCTGCG TGCGGAAGAT ACGGCCGTGT ATTATTGCGC GCGTCGTTAT
(301) TGGTCTAAGT CTCATGCTTC TGTTACTGAT TATTGGGGCC AAGGCACCCT
(351) GGTGACGGTT AGCTCA
```

3080_ VH3 (SEQ ID NO: 3):

```
(1)   CAGGTGCAAT TGGTGGAAAG CGGCGGCGGC CTGGTGCAAC CGGGCGGCAG
(51)  CCTGCGTCTG AGCTGCGCGG CCTCCGGATT TACCTTTTCT TCTTATGGTA
(101) TGCATTGGGT GCGCCAAGCC CCTGGGAAGG GTCTCGAGTG GGTGAGCAAT
(151) ATCTATTCTG ATGGTAGCAA TACCTTTTAT GCGGATAGCG TGAAAGGCCG
(201) TTTTACCATT TCACGTGATA ATTCGAAAAA CACCCTGTAT CTGCAAATGA
(251) ACAGCCTGCG TGCGGAAGAT ACGGCCGTGT ATTATTGCGC GCGTAATATG
(301) TATCGTTGGC CTTTTCATTA TTTTTTTGAT TATTGGGGCC AAGGCACCCT
(351) GGTGACGGTT AGCTCA
```

3100_VH 3 (SEQ ID NO: 4):

```
(1)   CAGGTGCAAT TGGTGGAAAG CGGCGGCGGC CTGGTGCAAC CGGGCGGCAG
(51)  CCTGCGTCTG AGCTGCGCGG CCTCCGGATT TACCTTTTCT TCTAATGGTA
(101) TGTCTTGGGT GCGCCAAGCC CCTGGGAAGG GTCTCGAGTG GGTGAGCAAT
(151) ATCTCTTATC TTTCTAGCTC TACCTATTAT GCGGATAGCG TGAAAGGCCG
(201) TTTTACCATT TCACGTGATA ATTCGAAAAA CACCCTGTAT CTGCAAATGA
(251) ACAGCCTGCG TGCGGAAGAT ACGGCCGTGT ATTATTGCGC GCGTTTTTAT
(301) GGTTATTTTA ATTATGCTGA TGTTTGGGGC CAAGGCACCC TGGTGACGGT
(351) TAGCTCA
```

3077_1_VH1B (SEQ ID NO: 31):

```
(1)   CAGGTGCAAT TAGTCCAAAG TGGTGCGGAA GTGAAAAAAC CGGGCGCGAG
(51)  CGTGAAAGTG AGCTGCAAAG CCTCCGGATA TACCTTTACT TCTTATTCTA
(101) TTAATTGGGT CCGCCAAGCC CCTGGGCAGG GTCTCGAGTG GATGGGCTAT
(151) ATCGATCCGA ATCGTGGCAA TACGAATTAC GCGCAGAAGT TTCAGGGCCG
```

Figure 1a (Continued)

```
(201) GGTGACCATG ACCCGTGATA CCAGCATTAG CACCGCGTAT ATGGAACTGA
(251) GCAGCCTGCG TAGCGAAGAT ACGGCCGTGT ATTATTGCGC GCGTGAGTAT
(301) ATTTATTTTA TTCATGGTAT GCTTGATTTT TGGGGCCAAG GCACCCTGGT
(351) GACGGTTAGC TCA
```

Figure 1b

Variable Heavy Chain Peptide (CDR Regions in Bold)

3077_VH1B (SEQ ID NO: 5):

(1)   QVQLVQSGAE VKKPGASVKV SCKASGYTFT SYSINWVRQA PGQGLEWMGY
(51)  IDPNRGNTNY AQKFQGRVTM TRDTSISTAY MELSSLRSED TAVYYCAREY
(101) IYFIHGMLDF WGQGTLVTVS S

3079_VH3 (SEQ ID NO: 6):

(1)   QVQLVESGGG LVQPGGSLRL SCAASGFTFS NYGMHWVRQA PGKGLEWVSN
(51)  IRSDGSWTYY ADSVKGRFTI SRDNSKNTLY LQMNSLRAED TAVYYCARRY
(101) WSKSHASVTD YWGQGTLVTV SS

3080_ VH3 (SEQ ID NO: 7):

(1)   QVQLVESGGG LVQPGGSLRL SCAASGFTFS SYGMHWVRQA PGKGLEWVSN
(51)  IYSDGSNTFY ADSVKGRFTI SRDNSKNTLY LQMNSLRAED TAVYYCARNM
(101) YRWPFHYFFD YWGQGTLVTV SS

3100_VH 3 (SEQ ID NO: 8):

(1)   QVQLVESGGG LVQPGGSLRL SCAASGFTFS SNGMSWVRQA PGKGLEWVSN
(51)  ISYLSSSTYY ADSVKGRFTI SRDNSKNTLY LQMNSLRAED TAVYYCARFY
(101) GYFNYADVWG QGTLVTVSS

Figure 2a

Variable Light Chain DNA

3077_Vk kappa 2 (SEQ ID NO: 9):

```
(1)   GATATCGTGA TGACCCAGAG CCCACTGAGC CTGCCAGTGA CTCCGGGCGA
(51)  GCCTGCGAGC ATTAGCTGCA GAAGCAGCCA AAGCCTGCTT TTTATTGATG
(101) GCAATAATTA TCTGAATTGG TACCTTCAAA AACCAGGTCA AAGCCCGCAG
(151) CTATTAATTT ATCTTGGTTC TAATCGTGCC AGTGGGGTCC CGGATCGTTT
(201) TAGCGGCTCT GGATCCGGCA CCGATTTTAC CCTGAAAATT AGCCGTGTGG
(251) AAGCTGAAGA CGTGGGCGTG TATTATTGCC AGCAGTATTC TTCTAAGTCT
(301) GCTACCTTTG GCCAGGGTAC GAAAGTTGAA ATTAAACGTA CG
```

3079_Vk kappa 1 (SEQ ID NO: 10):

```
(1)   GATATCCAGA TGACCCAGAG CCCGTCTAGC CTGAGCGCGA GCGTGGGTGA
(51)  TCGTGTGACC ATTACCTGCA GAGCGAGCCA GGATATTTCT GCTTTTCTGA
(101) ATTGGTACCA GCAGAAACCA GGTAAAGCAC CGAAACTATT AATTTATAAG
(151) GTTTCTAATT TGCAAAGCGG GGTCCCGTCC CGTTTTAGCG GCTCTGGATC
(201) CGGCACTGAT TTTACCCTGA CCATTAGCAG CCTGCAACCT GAAGACTTTG
(251) CGACTTATTA TTGCCAGCAG GCTTATTCTG TTCTATTAC CTTTGGCCAG
(301) GGTACGAAAG TTGAAATTAA ACGTACG
```

3080_Vl lambda 3 (SEQ ID NO: 11):

```
(1)   GATATCGAAC TGACCCAGCC GCCTTCAGTG AGCGTTGCAC CAGGTCAGAC
(51)  CGCGCGTATC TCGTGTAGCG GCGATAATAT TGGTAATAAG TATGTTTCTT
(101) GGTACCAGCA GAAACCCGGG CAGGCGCCAG TTGTTGTGAT TTATGGTGAT
(151) AATAATCGTC CCTCAGGCAT CCCGGAACGC TTTAGCGGAT CCAACAGCGG
(201) CAACACCGCG ACCCTGACCA TTAGCGGCAC TCAGGCGGAA GACGAAGCGG
(251) ATTATTATTG CTCTTCTTAT GATTCTTCTT ATTTGTGTT TGGCGGCGGC
(301) ACGAAGTTAA CCGTTCTTGG CCAG
```

3100_Vl lambda 3 (SEQ ID NO: 12):

```
(1)   GATATCGAAC TGACCCAGCC GCCTTCAGTG AGCGTTGCAC CAGGTCAGAC
(51)  CGCGCGTATC TCGTGTAGCG GCGATAATAT TGGTCATTAT TATGCTTCTT
(101) GGTACCAGCA GAAACCCGGG CAGGCGCCAG TTCTTGTGAT TTATCGTGAT
(151) AATGATCGTC CCTCAGGCAT CCCGGAACGC TTTAGCGGAT CCAACAGCGG
(201) CAACACCGCG ACCCTGACCA TTAGCGGCAC TCAGGCGGAA GACGAAGCGG
(251) ATTATTATTG CCAGTCTTAT GATTATCTTC ATGATTTGT GTTTGGCGGC
(301) GGCACGAAGT TAACCGTTCT TGGCCAG
```

Figure 2b

Variable Light Chain Peptide (CDR Regions in Bold)

3077_Vk kappa 2 (SEQ ID NO: 13):

```
(1)   DIVMTQSPLS LPVTPGEPAS ISCRSSQSLL FIDGNNYLNW YLQKPGQSPQ
(51)  LLIYLGSNRA SGVPDRFSGS GSGTDFTLKI SRVEAEDVGV YYCQQYSSKS
(101) ATFGQGTKVE IKRT
```

3079_Vk kappa 1 (SEQ ID NO: 14):

```
(1)   DIQMTQSPSS LSASVGDRVT ITCRASQDIS AFLNWYQQKP GKAPKLLIYK
(51)  VSNLQSGVPS RFSGSGSGTD FTLTISSLQP EDFATYYCQQ AYSGSITFGQ
(101) GTKVEIKRT
```

3080_Vl lambda 3 (SEQ ID NO: 15):

```
(1)   DIELTQPPSV SVAPGQTARI SCSGDNIGNK YVSWYQQKPG QAPVVVIYGD
(51)  NNRPSGIPER FSGSNSGNTA TLTISGTQAE DEADYYCSSY DSSYFVFGGG
(101) TKLTVLGQ
```

3100_Vl lambda 3 (SEQ ID NO: 16):

```
(1)   DIELTQPPSV SVAPGQTARI SCSGDNIGHY YASWYQQKPG QAPVLVIYRD
(51)  NDRPSGIPER FSGSNSGNTA TLTISGTQAE DEADYYCQSY DYLHDFVFGG
(101) GTKLTVLGQ
```

Figure 3

Variable Heavy Chain Consensus Sequences (CDR Regions in Bold)

VH1B Consensus (SEQ ID NO: 17):

```
(1)   QVQLVQSGAE VKKPGASVKV SCKAS GYTFT SYYMHWVRQA PGQGLEWMGW
(51)  INPNSGGTNY AQKFQGRVTM TRDTSISTAY MELSSLRSED TAVYYCARWG
(101) GDGFYAMDYW GQGTLVTVSS
```

VH3 Consensus (SEQ ID NO: 18):

```
(1)   QVQLVESGGG LVQPGGSLRL SCAAS GFTFS SYAMSWVRQA PGKGLEWVSA
(51)  ISGSGGSTYY ADSVKGRFTI SRDNSKNTLY LQMNSLRAED TAVYYCARWG
(101) GDGFYAMDYW GQGTLVTVS S
```

Figure 4

Variable Light Chain Consensus Sequences (CDR Regions in Bold)

VL_λ3 Consensus (SEQ ID NO: 19):

```
(1)   SYELTQPPSV SVAPGQTARI SCSGDALGDK YASWYQQKPG QAPVLVIYDD
(51)  SDRPSGIPER FSGSNSGNTA TLTISGTQAE DEADYYCQQH YTTPPVFGGG
(101) TKLTVLG
```

VL_k1 Consensus (SEQ ID NO: 20):

```
(1)   DIQMTQSPSS LSASVGDRVT ITCRASQGIS SYLAWYQQKP GKAPKLLIYA
(51)  ASSLQSGVPS RFSGSGSGTD FTLTISSLQP EDFATYYCQQ HYTTPPTFGQ
(101) GTKVEIKR
```

VL_k2 Consensus (SEQ ID NO: 21):

```
(1)   DIVMTQSPLS LPVTPGEPAS ISCRSSQSLL HSNGYNYLDW YLQKPGQSPQ
(51)  LLIYLGSNRA SGVPDRFSGS GSGTDFTLKI SRVEAEDVGV YYCQQHYTTP
(101) PTFGQGTKVE IKR
```

Figure 5

Peptide Sequence of CD38

(SEQ ID NO: 22):

| | | | | | | |
|---|---|---|---|---|---|---|
| 1 | mancefspvs | gdkpccrlsr | raqlclgvsi | lvlilvvvla | vvvprwrqqw | sgpgttkrfp |
| 61 | etvlarcvky | teihpemrhv | dcqsvwdafk | gafiskhpcn | iteedyqplm | klgtqtvpcn |
| 121 | killwsrikd | lahqftqvqr | dmftledtll | gyladdltwc | gefntskiny | qscpdwrkdc |
| 181 | snnpvsvfwk | tvsrrfaeaa | cdvvhvmlng | srskifdkns | tfgsvevhnl | qpekvqtlea |
| 241 | wvihggreds | rdlcqdptik | elesiiskrn | iqfsckniyr | pdkflqcvkn | pedssctsei |

Figure 6

Nucleotide Sequence of Chimeric OKT10

Heavy Chain (SEQ ID NO: 23):

```
caggtggaat tggtggaatc tggaggatcc ctgaaactct cctgtgcagc ctcaggattc
gattttagta gatcctggat gaattgggtc cggcaggctc caggaaaagg gctagaatgg
attggagaaa ttaatccaga tagcagtacg ataaactata cgacatctct aaaggataaa
ttcatcatct ccagagacaa cgccaaaaat acgctgtacc tgcaaatgac caaagtgaga
tctgaggaca cagcccttta ttactgtgca agatatggta actggtttcc ttattggggc
caagggactc tggtcactgt cagctcagcc tccaccaagg gtccatcggt cttccccctg
gcaccctcct ccaagagcac ctctgggggc acagcggccc tgggctgcct ggtcaaggac
tacttccccg aaccggtgac ggtgtcgtgg aactcaggcg ccctgaccag cggcgtgcac
accttcccgg ctgtcctaca gtcctcagga ctctactccc tcagcagcgt ggtgaccgtg
ccctccagca gcttgggcac ccagacctac atctgcaacg tgaatcacaa gcccagcaac
accaaggtgg acaagaaagt tgagcccaaa tcttgtgaca aaactcacac atgcccaccg
tgcccagcac ctgaactcct ggggggaccg tcagtcttcc tcttccccc aaaacccaag
gacaccctca tgatctcccg gacccctgag gtcacatgcg tggtggtgga cgtgagccac
gaagaccctg aggtcaagtt caactggtac gtggacggcg tggaggtgca taatgccaag
acaaagccgc gggaggagca gtacaacagc acgtaccggg tggtcagcgt cctcaccgtc
ctgcaccagg actggctgaa tggcaaggag tacaagtgca aggtctccaa caaagccctc
ccagcccca tcgagaaaac catctccaaa gccaaaggc agccccgaga accacaggtg
tacaccctgc ccccatcccg ggatgagctg accaagaacc aggtcagcct gacctgcctg
gtcaaaggct tctatcccag cgacatcgcc gtggagtggg agagcaatgg gcagccggag
aacaactaca agaccacgcc tcccgtgctg gactccgacg gctccttctt cctctacagc
aagctcaccg tggacaagag caggtggcag caggggaacg tcttctcatg ctccgtgatg
catgaggctc tgcacaacca ctacacgcag aagagcctct ccctgtctcc gggtaaa
```

Light Chain (SEQ ID NO: 24):

```
gatatcctga tgacccagtc tcaaaaaatc atgcccacat cagtgggaga cagggtcagc
gtcacctgca aggccagtca aatgtggat actaatgtag cctggtatca acagaaacca
```

Figure 6 (Continued)

```
ggacagtctc ctaaagcact gatttactcg gcatcctacc gatacagtgg agtccctgat cgcttcacag gcagtggatc tgggacagat ttcactctca ccatcaccaa tgtgcagtct gaggacttgg cagagtattt ctgtcagcaa tatgacagct atcctctcac gttcggtgct gggaccaagc tggacctgaa acgtacggtg gctgcaccat ctgtcttcat cttcccgcca tctgatgagc agttgaaatc tggaactgcc tctgttgtgt gcctgctgaa taacttctat cccagagagg ccaaagtaca gtggaaggtg gataacgccc tccaatcggg taactcccag gagagtgtca cagagcagga cagcaaggac agcacctaca gcctcagcag caccctgacg ctgagcaaag cagactacga gaaacacaaa gtctacgcct gcgaagtcac ccatcagggc ctgagctcgc ccgtcacaaa gagcttcaac aggggagagt gt
```

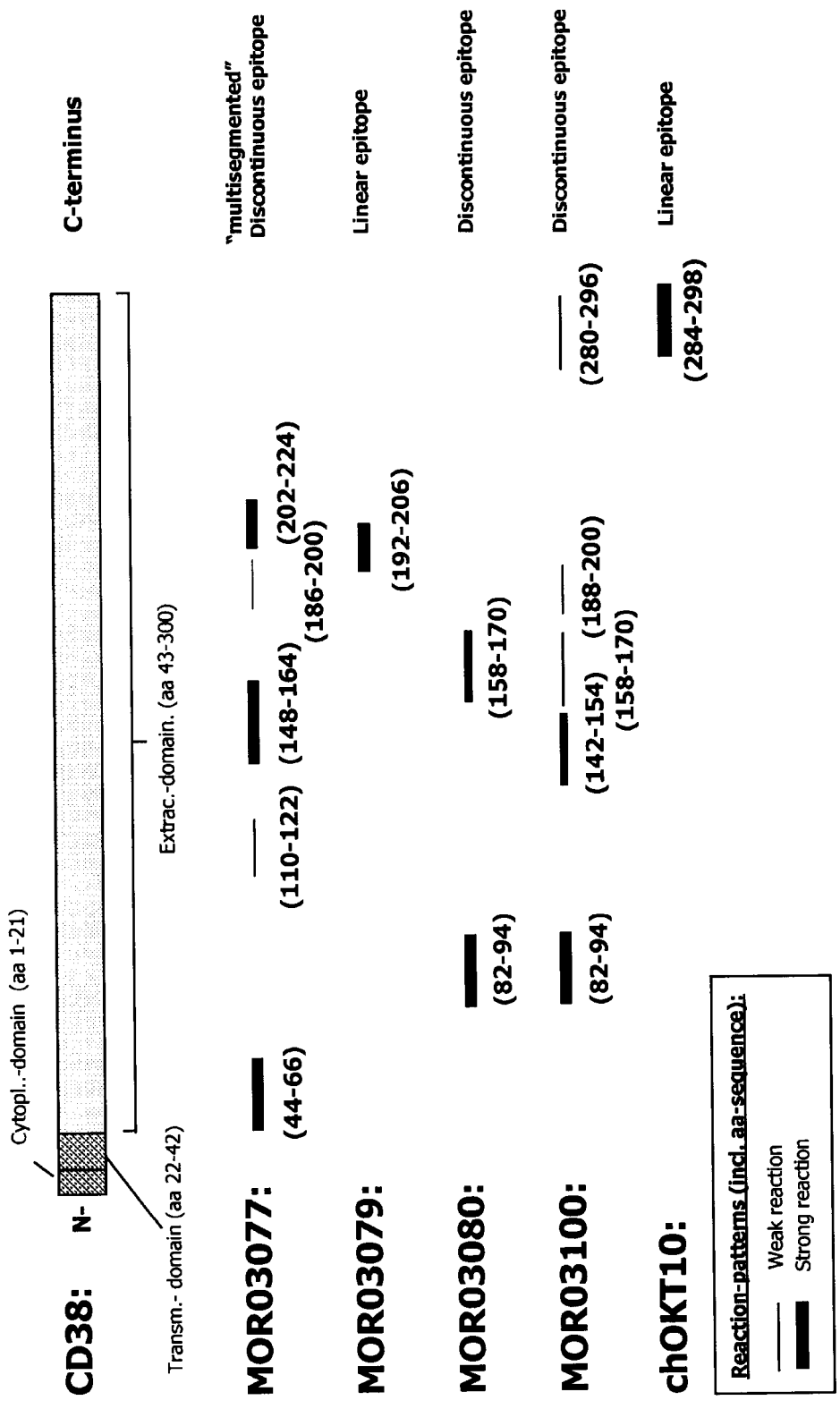

Figure 8: DNA sequence of pMOPRH®_h_IgG1_1

```
                        StyI
                      ~~~~~~
        601   TCGCTATTAC CATGGTGATG CGGTTTTGGC AGTACATCAA TGGGCGTGGA
              AGCGATAATG GTACCACTAC GCCAAAACCG TCATGTAGTT ACCCGCACCT

AatII
                                                            ~~~~~~
        651   TAGCGGTTTG ACTCACGGGG ATTTCCAAGT CTCCACCCCA TTGACGTCAA
              ATCGCCAAAC TGAGTGCCCC TAAAGGTTCA GAGGTGGGGT AACTGCAGTT

701   TGGGAGTTTG TTTTGGCACC AAAATCAACG GGACTTTCCA AAATGTCGTA
              ACCCTCAAAC AAAACCGTGG TTTTAGTTGC CCTGAAAGGT TTTACAGCAT

751   ACAACTCCGC CCCATTGACG CAAATGGGCG GTAGGCGTGT ACGGTGGGAG
              TGTTGAGGCG GGGTAACTGC GTTTACCCGC CATCCGCACA TGCCACCCTC

801   GTCTATATAA GCAGAGCTCT CTGGCTAACT AGAGAACCCA CTGCTTACTG
              CAGATATATT CGTCTCGAGA GACCGATTGA TCTCTTGGGT GACGAATGAC pMORPH®_Ig_FOR 100.0%                NheI
                    ~~~~~~~~~~~~~~~~~~~~~~~               ~~~~~~
        851   GCTTATCGAA ATTAATACGA CTCACTATAG GGAGACCCAA GCTGGCTAGC
              CGAATAGCTT TAATTATGCT GAGTGATATC CCTCTGGGTT CGACCGATCG

M   K   H   L   W   F   F   L   L   V   A   A   P   R ·
        901   GCCACCATGA AACACCTGTG GTTCTTCCTC CTGCTGGTGG CAGCTCCCAG
              CGGTGGTACT TTGTGGACAC CAAGAAGGAG GACGACCACC GTCGAGGGTC

EcoRI                BlpI          StyI
                             ~~~~~~              ~~~~~~~~         ~
                                                           A   S   T ·
              ·  W   V   L   S   Q   V   E   F   C   R   R   L   A   Q
        951   ATGGGTCCTG TCCCAGGTGG AATTCTGCAG GCGGTTAGCT CAGCCTCCAC
              TACCCAGGAC AGGGTCCACC TTAAGACGTC CGCCAATCGA GTCGGAGGTG

StyI        BbsI
              ~~~~~       ~~~~~~
              ·  K   G   P   S   V   F   P   L   A   P   S   S   K   S   T   S   G ·
       1001   CAAGGGTCCA TCGGTCTTCC CCCTGGCACC CTCCTCCAAG AGCACCTCTG
              GTTCCCAGGT AGCCAGAAGG GGGACCGTGG GAGGAGGTTC TCGTGGAGAC

·  G   T   A   L   G   C   L   V   K   D   Y   F   P   E   P
       1051   GGGGCACAGC GGCCCTGGGC TGCCTGGTCA AGGACTACTT CCCCGAACCG
              CCCCGTGTCG CCGGGACCCG ACGGACCAGT TCCTGATGAA GGGGCTTGGC
```

Figure 8 (Continued)

```
              V  T  V  S   W  N  S  G  A  L   T  S  G  V   H  T  F  ·
1101    GTGACGGTGT CGTGGAACTC AGGCGCCCTG ACCAGCGGCG TGCACACCTT
        CACTGCCACA GCACCTTGAG TCCGCGGGAC TGGTCGCCGC ACGTGTGGAA

· P  A  V   L  Q  S  S   G  L  Y   S  L  S   S  V  V  T  ·
1151    CCCGGCTGTC CTACAGTCCT CAGGACTCTA CTCCCTCAGC AGCGTGGTGA
        GGGCCGACAG GATGTCAGGA GTCCTGAGAT GAGGGAGTCG TCGCACCACT

· V  P  S   S  S  L   G  T  Q  T   Y  I  C   N  V  N
1201    CCGTGCCCTC CAGCAGCTTG GGCACCCAGA CCTACATCTG CAACGTGAAT
        GGCACGGGAG GTCGTCGAAC CCGTGGGTCT GGATGTAGAC GTTGCACTTA

StyI
                            ~~~~~~
        H  K  P  S   N  T  K   V  D  K   K  V  E  P   K  S  C  ·
1251    CACAAGCCCA GCAACACCAA GGTGGACAAG AAAGTTGAGC CCAAATCTTG
        GTGTTCGGGT CGTTGTGGTT CCACCTGTTC TTTCAACTCG GGTTTAGAAC

· D  K  T   H  T  C  P   P  C  P   A  P  E   L  L  G  G  ·
1301    TGACAAAACT CACACATGCC CACCGTGCCC AGCACCTGAA CTCCTGGGGG
        ACTGTTTTGA GTGTGTACGG GTGGCACGGG TCGTGGACTT GAGGACCCCC

BbsI                             StyI
                  ~~~~~~                           ~~~~~~
        · P  S  V   F  L  F   P  P  K  P   K  D  T   L  M  I
1351    GACCGTCAGT CTTCCTCTTC CCCCCAAAAC CCAAGGACAC CCTCATGATC
        CTGGCAGTCA GAAGGAGAAG GGGGGTTTTG GGTTCCTGTG GGAGTACTAG

BbsI
                                                    ~~~~~
        S  R  T  P   E  V  T   C  V  V   V  D  V  S   H  E  D  ·
1401    TCCCGGACCC CTGAGGTCAC ATGCGTGGTG GTGGACGTGA GCCACGAAGA
        AGGGCCTGGG GACTCCAGTG TACGCACCAC CACCTGCACT CGGTGCTTCT

BbsI
        ~
        · P  E  V   K  F  N  W   Y  V  D   G  V  E   V  H  N  A  ·
1451    CCCTGAGGTC AAGTTCAACT GGTACGTGGA CGGCGTGGAG GTGCATAATG
        GGGACTCCAG TTCAAGTTGA CCATGCACCT GCCGCACCTC CACGTATTAC

· K  T  K   P  R  E   E  Q  Y  N   S  T  Y   R  V  V
1501    CCAAGACAAA GCCGCGGGAG GAGCAGTACA ACAGCACGTA CCGGGTGGTC
        GGTTCTGTTT CGGCGCCCTC CTCGTCATGT TGTCGTGCAT GGCCCACCAG

S  V  L  T   V  L  H   Q  D  W   L  N  G  K   E  Y  K  ·
1551    AGCGTCCTCA CCGTCCTGCA CCAGGACTGG CTGAATGGCA AGGAGTACAA
        TCGCAGGAGT GGCAGGACGT GGTCCTGACC GACTTACCGT TCCTCATGTT

· C  K  V   S  N  K  A   L  P  A   P  I  E   K  T  I  S  ·
1601    GTGCAAGGTC TCCAACAAAG CCCTCCCAGC CCCCATCGAG AAAACCATCT
        CACGTTCCAG AGGTTGTTTC GGGAGGGTCG GGGGTAGCTC TTTTGGTAGA

BsrGI
                                            ~~~~~~
        · K  A  K   G  Q  P   R  E  P  Q   V  Y  T   L  P  P
1651    CCAAAGCCAA AGGGCAGCCC CGAGAACCAC AGGTGTACAC CCTGCCCCCA
        GGTTTCGGTT TCCCGTCGGG GCTCTTGGTG TCCACATGTG GGACGGGGGT
```

Figure 8 (Continued)

```
          S   R   D   E     L   T   K     N   Q   V     S   L   T   C     L   V   K  ·
1701      TCCCGGGATG       AGCTGACCAA    GAACCAGGTC    AGCCTGACCT       GCCTGGTCAA
          AGGGCCCTAC       TCGACTGGTT    CTTGGTCCAG    TCGGACTGGA       CGGACCAGTT

·   G   F   Y     P   S   D     I   A   V   E     W   E   S     N   G   Q   P   ·
1751      AGGCTTCTAT       CCCAGCGACA    TCGCCGTGGA    GTGGGAGAGC       AATGGGCAGC
          TCCGAAGATA       GGGTCGCTGT    AGCGGCACCT    CACCCTCTCG       TTACCCGTCG

·   E   N   N     Y   K   T     T   P   P   V     L   D   S       D   G   S
1801      CGGAGAACAA       CTACAAGACC    ACGCCTCCCG    TGCTGGACTC       CGACGGCTCC
          GCCTCTTGTT       GATGTTCTGG    TGCGGAGGGC    ACGACCTGAG       GCTGCCGAGG

F   F   L   Y     S   K   L     T   V   D     K   S   R     W   Q   Q   G   ·
1851      TTCTTCCTCT       ACAGCAAGCT    CACCGTGGAC    AAGAGCAGGT       GGCAGCAGGG
          AAGAAGGAGA       TGTCGTTCGA    GTGGCACCTG    TTCTCGTCCA       CCGTCGTCCC

BbsI                            NsiI
              ~~~~~~~                         ~~~~~~
          ·   N   V   F     S   C   S     V   M   H   E     A   L   H     N   H   Y   T   ·
1901      GAACGTCTTC       TCATGCTCCG    TGATGCATGA    GGCTCTGCAC       AACCACTACA
          CTTGCAGAAG       AGTACGAGGC    ACTACGTACT    CCGAGACGTG       TTGGTGATGT

SapI                                                         PmeI
              ~~~~~~~                                                      ~~~~~~~
          ·   Q   K   S     L   S   L     S   P   G   K     *
1951      CGCAGAAGAG       CCTCTCCCTG    TCTCCGGGTA    AATGAGGGCC       CGTTTAAACC
          GCGTCTTCTC       GGAGAGGGAC    AGAGGCCCAT    TTACTCCCGG       GCAAATTTGG

2001      CGCTGATCAG       CCTCGACTGT    GCCTTCTAGT    TGCCAGCCAT       CTGTTGTTTG
          GCGACTAGTC       GGAGCTGACA    CGGAAGATCA    ACGGTCGGTA       GACAACAAAC

~~~~~~~~~~~~~~~~~~~~~
                    pMORPH®_Ig_REV 100.0%
2051      CCCCTCCCCC       GTGCCTTCCT    TGACCCTGGA    AGGTGCCACT       CCCACTGTCC
          GGGGAGGGGG       CACGGAAGGA    ACTGGGACCT    TCCACGGTGA       GGGTGACAGG
```

Figure 9: DNA Sequence of Ig kappa light chain expression vector pMORPH®_h_Igκ_1

```
                        StyI
                     ~~~~~~~
  601  TCGCTATTAC CATGGTGATG CGGTTTTGGC AGTACATCAA TGGGCGTGGA
       AGCGATAATG GTACCACTAC GCCAAAACCG TCATGTAGTT ACCCGCACCT

651  TAGCGGTTTG ACTCACGGGG ATTTCCAAGT CTCCACCCCA TTGACGTCAA
       ATCGCCAAAC TGAGTGCCCC TAAAGGTTCA GAGGTGGGGT AACTGCAGTT

701  TGGGAGTTTG TTTTGGCACC AAAATCAACG GGACTTTCCA AAATGTCGTA
       ACCCTCAAAC AAAACCGTGG TTTTAGTTGC CCTGAAAGGT TTTACAGCAT

751  ACAACTCCGC CCCATTGACG CAAATGGGCG GTAGGCGTGT ACGGTGGGAG
       TGTTGAGGCG GGGTAACTGC GTTTACCCGC CATCCGCACA TGCCACCCTC

801  GTCTATATAA GCAGAGCTCT CTGGCTAACT AGAGAACCCA CTGCTTACTG
       CAGATATATT CGTCTCGAGA GACCGATTGA TCTCTTGGGT GACGAATGAC pMORPH®_Ig_FOR 100%             NheI
              ========================        ~~~~~~
  851  GCTTATCGAA ATTAATACGA CTCACTATAG GGAGACCCAA GCTGGCTAGC
       CGAATAGCTT TAATTATGCT GAGTGATATC CCTCTGGGTT CGACCGATCG

+1      M  V  L  Q  T  Q  V  F  I  S  L  L  L  W  I
             StyI
          ~~~~~~
  901  GCCACCATGG TGTTGCAGAC CCAGGTCTTC ATTTCTCTGT TGCTCTGGAT
       CGGTGGTACC ACAACGTCTG GGTCCAGAAG TAAAGAGACA ACGAGACCTA
                                                   BbsI
                                                ~~~~~~

+1  S  G  A  Y  G  D  I  V  M  I  K  R  T  V  A  A
                           EcoRV           BsiWI
                         ~~~~~~          ~~~~~~
  951  CTCTGGTGCC TACGGGGATA TCGTGATGAT TAAACGTACG GTGGCTGCAC
       GAGACCACGG ATGCCCCTAT AGCACTACTA ATTTGCATGC CACCGACGTG

+1 P  S  V  F  I  F  P  P  S  D  E  Q  L  K  S  G  T
 1001  CATCTGTCTT CATCTTCCCG CCATCTGATG AGCAGTTGAA ATCTGGAACT
       GTAGACAGAA GTAGAAGGGC GGTAGACTAC TCGTCAACTT TAGACCTTGA
          BbsI
       ~~~~~~
```

Figure 9 (Continued)

```
     +1   A   S   V   V   C   L   L   N   N   F   Y   P   R   E   A   K   V
    1051  GCCTCTGTTG TGTGCCTGCT GAATAACTTC TATCCCAGAG AGGCCAAAGT
          CGGAGACAAC ACACGGACGA CTTATTGAAG ATAGGGTCTC TCCGGTTTCA

+1   Q   W   K   V   D   N   A   L   Q   S   G   N   S   Q   E   S
    1101  ACAGTGGAAG GTGGATAACG CCCTCCAATC GGGTAACTCC CAGGAGAGTG
          TGTCACCTTC CACCTATTGC GGGAGGTTAG CCCATTGAGG GTCCTCTCAC

+1 V   T   E   Q   D   S   K   D   S   T   Y   S   L   S   S   T   L
    1151  TCACAGAGCA GGACAGCAAG GACAGCACCT ACAGCCTCAG CAGCACCCTG
          AGTGTCTCGT CCTGTCGTTC CTGTCGTGGA TGTCGGAGTC GTCGTGGGAC

+1   T   L   S   K   A   D   Y   E   K   H   K   V   Y   A   C   E   V
             BlpI
             ~~~~~~~
    1201  ACGCTGAGCA AAGCAGACTA CGAGAAACAC AAAGTCTACG CCTGCGAAGT
          TGCGACTCGT TTCGTCTGAT GCTCTTTGTG TTTCAGATGC GGACGCTTCA

+1   T   H   Q   G   L   S   S   P   V   T   K   S   F   N   R   G
    1251  CACCCATCAG GGCCTGAGCT CGCCCGTCAC AAAGAGCTTC AACAGGGGAG
          GTGGGTAGTC CCGGACTCGA GCGGGCAGTG TTTCTCGAAG TTGTCCCCTC

+1   E   C   *
                              PmeI                      pMORPH®_Ig_REV 100%
                              ~~~~~~~~                  ====================
    1301  AGTGTTAGGG GCCCGTTTAA ACCCGCTGAT CAGCCTCGAC TGTGCCTTCT
          TCACAATCCC CGGGCAAATT TGGGCGACTA GTCGGAGCTG ACACGGAAGA

=
    1351  AGTTGCCAGC CATCTGTTGT TTGCCCCTCC CCCGTGCCTT CCTTGACCCT
          TCAACGGTCG GTAGACAACA AACGGGGAGG GGGCACGGAA GGAACTGGGA
```

Figure 10: DNA Sequence of HuCAL® Ig lambda light chain vector pMORPH®_h_Igλ_1

```
              StyI
              ~~~~~~
601   TCGCTATTAC CATGGTGATG CGGTTTTGGC AGTACATCAA TGGGCGTGGA
      AGCGATAATG GTACCACTAC GCCAAAACCG TCATGTAGTT ACCCGCACCT

651   TAGCGGTTTG ACTCACGGGG ATTTCCAAGT CTCCACCCCA TTGACGTCAA
      ATCGCCAAAC TGAGTGCCCC TAAAGGTTCA GAGGTGGGGT AACTGCAGTT

701   TGGGAGTTTG TTTTGGCACC AAAATCAACG GGACTTTCCA AAATGTCGTA
      ACCCTCAAAC AAAACCGTGG TTTTAGTTGC CCTGAAAGGT TTTACAGCAT

751   ACAACTCCGC CCCATTGACG CAAATGGGCG GTAGGCGTGT ACGGTGGGAG
      TGTTGAGGCG GGGTAACTGC GTTTACCCGC CATCCGCACA TGCCACCCTC

801   GTCTATATAA GCAGAGCTCT CTGGCTAACT AGAGAACCCA CTGCTTACTG
      CAGATATATT CGTCTCGAGA GACCGATTGA TCTCTTGGGT GACGAATGAC pM_Ig_FOR  100.0%                    NheI
              ======================               ~~~~~~
851   GCTTATCGAA ATTAATACGA CTCACTATAG GGAGACCCAA GCTGGCTAGC
      CGAATAGCTT TAATTATGCT GAGTGATATC CCTCTGGGTT CGACCGATCG

+1         M  A  W  A  L    L  L  T  L    L  T  Q  G  T
            StyI
            ~~~~~~
901   GCCACCATGG CCTGGGCTCT GCTGCTCCTC ACCCTCCTCA CTCAGGGCAC
      CGGTGGTACC GGACCCGAGA CGACGAGGAG TGGGAGGAGT GAGTCCCGTG

+2                                         T  V  L  G  Q
+1    G  S  W  A  D  I    V  M  H  E    V
            BamHI      EcoRV           HpaI    StyI
            ~~~~~~     ~~~~~~          ~~~~~~  ~~~~~~
951   AGGATCCTGG GCTGATATCG TGATGCACGA AGTTAACCGT CCTAGGTCAG
      TCCTAGGACC CGACTATAGC ACTACGTGCT TCAATTGGCA GGATCCAGTC

+2    P  K  A  A  P  S    V  T  L  F    P  P  S  S  E  E  L
            StyI
            ~~~~~~
1001  CCCAAGGCTG CCCCCTCGGT CACTCTGTTC CCGCCCTCCT CTGAGGAGCT
      GGGTTCCGAC GGGGGAGCCA GTGAGACAAG GGCGGGAGGA GACTCCTCGA

+2    Q  A  N  K  A  T    L  V  C  L    I  S  D  F  Y  P
1051  TCAAGCCAAC AAGGCCACAC TGGTGTGTCT CATAAGTGAC TTCTACCCGG
      AGTTCGGTTG TTCCGGTGTG ACCACACAGA GTATTCACTG AAGATGGGCC
```

Figure 10 (Continued)

```
     +2  G    A    V    T     V    A    W     K    G    D     S    P    V     K    A    G
1101     GAGCCGTGAC  AGTGGCCTGG  AAGGGAGATA  GCAGCCCCGT  CAAGGCGGGA
         CTCGGCACTG  TCACCGGACC  TTCCCTCTAT  CGTCGGGGCA  GTTCCGCCCT

+2  V    E    T    T     T    P    S     K    Q    S     N    N    K     Y    A    A    S
1151     GTGGAGACCA  CCACACCCTC  CAAACAAAGC  AACAACAAGT  ACGCGGCCAG
         CACCTCTGGT  GGTGTGGGAG  GTTTGTTTCG  TTGTTGTTCA  TGCGCCGGTC

+2  S    Y    L    S     L    T    P     E    Q    W     K    S    H     R    S    Y
1201     CAGCTATCTG  AGCCTGACGC  TGAGCAGTG   GAAGTCCCAC  AGAAGCTACA
         GTCGATAGAC  TCGGACTGCG  GACTCGTCAC  CTTCAGGGTG  TCTTCGATGT

+2  S    C    Q    V     T    H    E     G    S    T     V    E    K     T    V    A    P
                                                                       BbsI
                                                                      ~~~~~~
1251     GCTGCCAGGT  CACGCATGAA  GGGAGCACCG  TGGAGAAGAC  AGTGGCCCCT
         CGACGGTCCA  GTGCGTACTT  CCCTCGTGGC  ACCTCTTCTG  TCACCGGGGA

+2  T    E    C    S     *
                                     PmeI
                                   ~~~~~~~~
1301     ACAGAATGTT  CATAGGGGCC  CGTTTAAACC  CGCTGATCAG  CCTCGACTGT
         TGTCTTACAA  GTATCCCCGG  GCAAATTTGG  GCGACTAGTC  GGAGCTGACA
                                                          pM_Ig_REV 100%
                                                          ==========

1351     GCCTTCTAGT  TGCCAGCCAT  CTGTTGTTTG  CCCCTCCCCC  GTGCCTTCCT
         CGGAAGATCA  ACGGTCGGTA  GACAACAAAC  GGGGAGGGGG  CACGGAAGGA
         pM_Ig_REV   100.0%
         =========
```

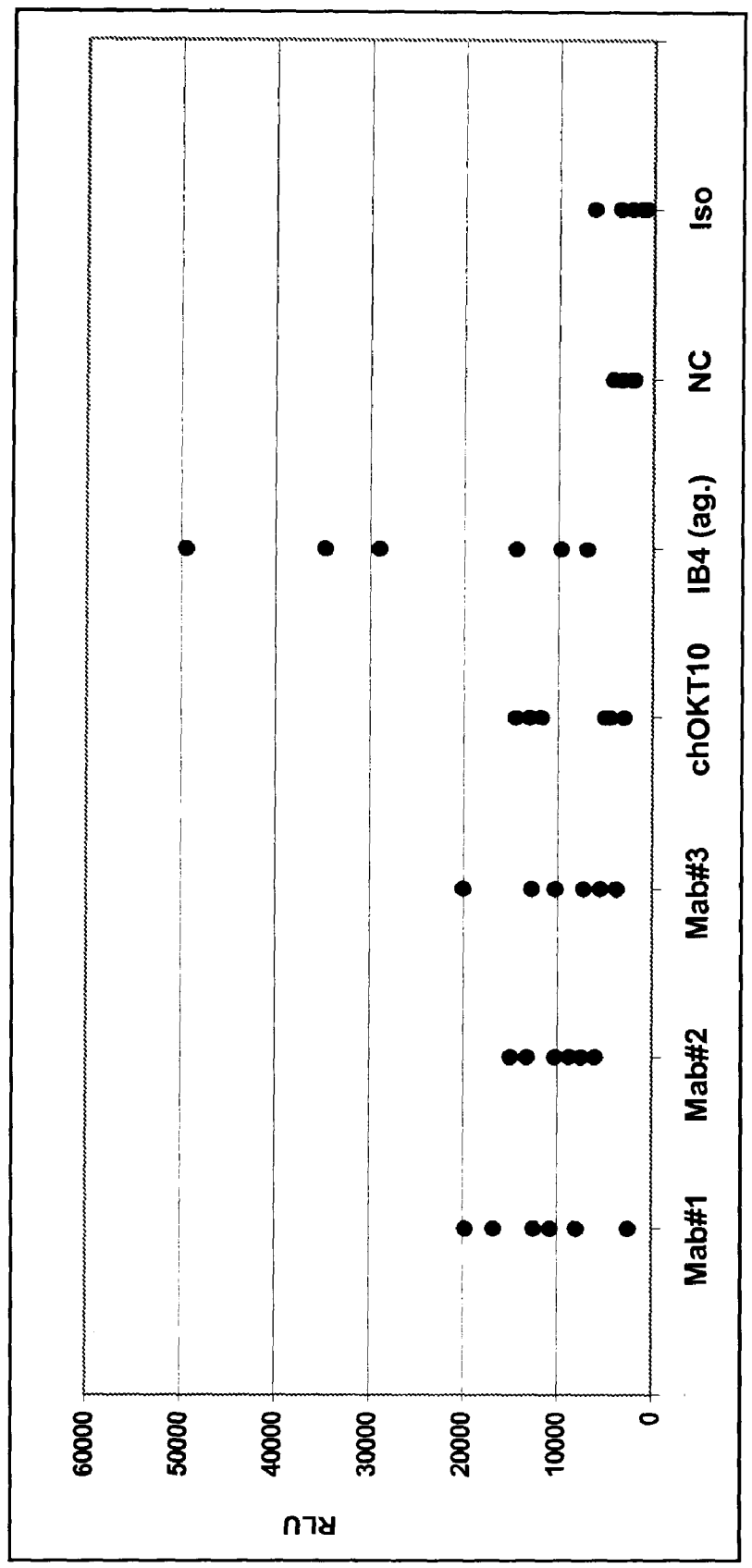
Fig. 11: Proliferation Assay

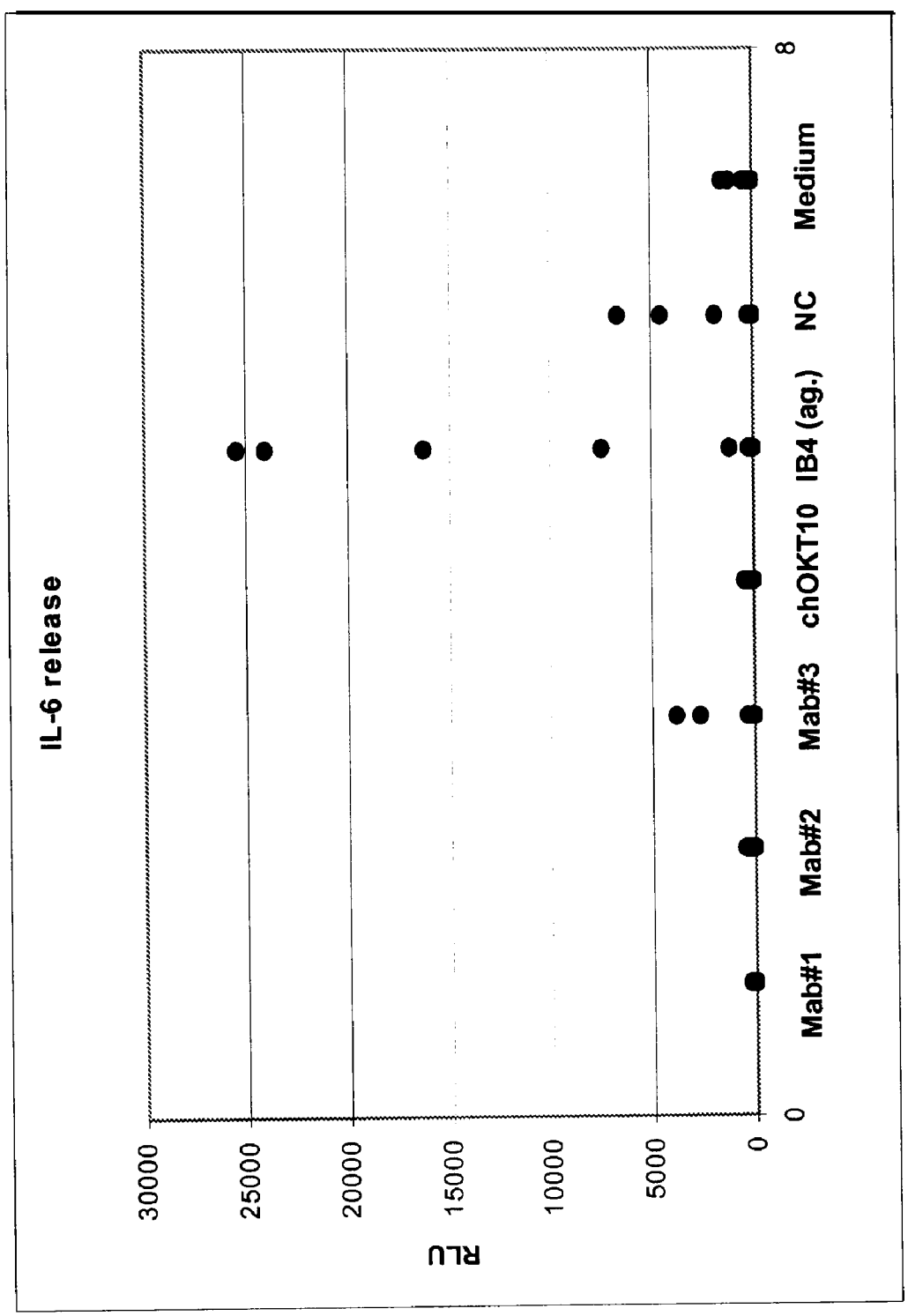
Fig. 12: IL-6 Release Assay

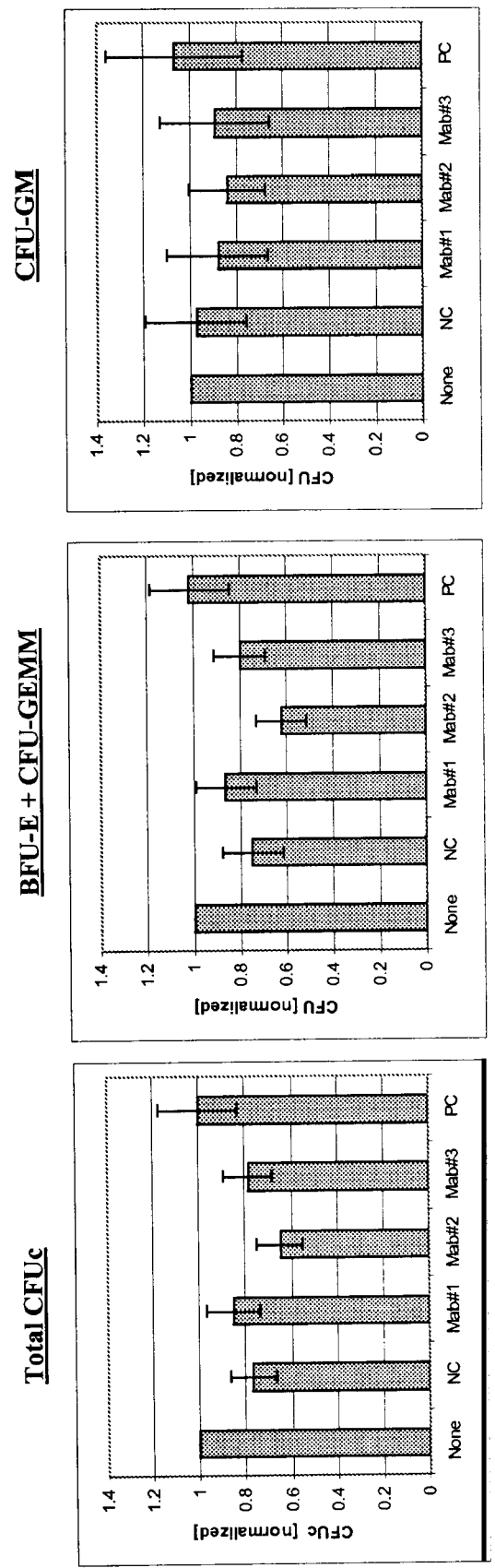
Fig. 13: Cytotoxicity towards CD34+/CD38+ progenitor cells

Fig. 14: ADCC with different cell-lines

| Cell line | Culture Collection | Origin | Expression [MFI] | Max. specific killing [%] in ADCC[a,c] | | | |
|---|---|---|---|---|---|---|---|
| | | | | Mab#1 | Mab#2 | Mab#3 | PC |
| RPMI 8226 | ATCC CCL-155 | MM | 405.71 | 56 | 58 | 54 | 46 |
| KMS-12-BM | DSMZ ACC551 | MM | 142.29 | 26 | 32 | 30 | 34 |
| NCI-H929 | ECACC95050415 | MM | 45.01 | 68 | 73 | 38 | 54 |
| OPM-2 | DSMZ ACC50 | MM | 37.99 | 6 | 13 | 3 | 7 |
| U-266 | ECACC85051003 | MM | 26.14 | 17 | 14 | 12 | 16 |
| KMS-11 | Namba et al., 1989[b] | MM | 26.81[d] | 22 | 30 | 26 | 28 |
| JVM-13 | DSMZACC19 | CLL | 463.93 | 11 | 20 | 12 | 15 |
| JVM-2 | DSMZACC12 | CLL | 140.84 | 22 | 28 | 10 | 24 |
| CCRF-CEM | ECACC85112105 | ALL | 301.46 | 24 | 29 | 20 | 22 |
| Jurkat | DSMZ ACC282 | ALL | 202.99 | 7 | 8 | 13 | 12 |
| AML-193 | DSMZ ACC549 | AML | 62.69[d] | 33 | 26 | 39 | 33 |
| OCI-AML5 | DSMZ ACC247 | AML | 207.55[d] | 20 | 21 | 16 | 26 |
| NB-4 | DSMZ ACC207 | AML | 164.7[d] | 36 | 38 | 32 | 37 |
| THP-1 | DSMZ ACC16 | AML | 34.41 | 64 | 59 | 38 | 43 |
| HL-60[d] | DSMZ ACC3 | AML | 18.43[d] | 29 | 35 | 29 | 29 |
| Raji | Burkitt's Lymph. | Burkitt's lymph. | n.d. | 53 | 62 | 48 | n.d. |

Fig. 15: ADCC with MM-samples

| Antibodies<br>Parameters: | Mab#1 | Mab#2 | Mab#3 | PC |
|---|---|---|---|---|
| MM samples: EC50 [nM][a]: | 0.116-0.202 | 0.006-0.185 | 0.027-0.249 | 0.282-0.356 |
| MM samples: Max spec. killing [%] | 13.1 - 61.6 | 16.2 - 57.9 | 13.6 - 36.0 | 15.5 - 49.5 |

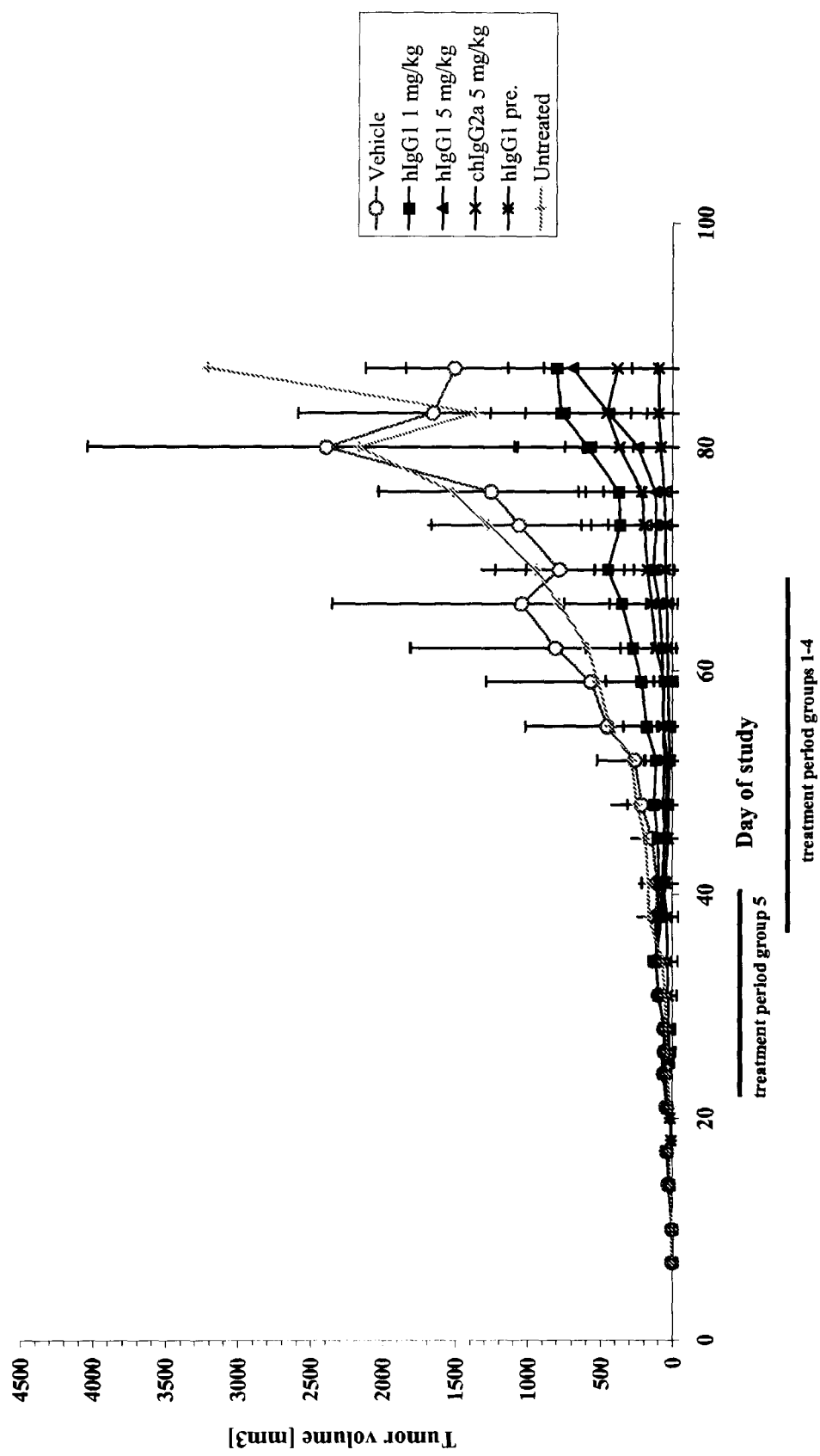
Fig. 16: Treatment of human myeloma xenograft with MOR03080

SEQUENCE LISTING

<160> NUMBER OF SEQ ID NOS: 43

<210> SEQ ID NO 1
<211> LENGTH: 363
<212> TYPE: DNA
<213> ORGANISM: Homo sapiens

<400> SEQUENCE: 1

```
caggtgcaat tggttcagag cggcgcggaa gtgaaaaaac cgggcgcgag cgtgaaagtg      60
agctgcaaag cctccggata tacctttact tcttattcta ttaattgggt ccgccaagcc     120
cctgggcagg gtctcgagtg gatgggctat atcgatccga atcgtggcaa tacgaattac     180
gcgcagaagt tcagggccg ggtgaccatg acccgtgata ccagcattag caccgcgtat     240
atggaactga gcagcctgcg tagcgaagat acggccgtgt attattgcgc gcgtgagtat     300
atttatttta ttcatggtat gcttgatttt tggggccaag gcaccctggt gacggttagc     360
tca                                                                    363
```

<210> SEQ ID NO 2
<211> LENGTH: 366
<212> TYPE: DNA
<213> ORGANISM: Homo sapiens

<400> SEQUENCE: 2

```
caggtgcaat tggtggaaag cggcggcggc ctggtgcaac cgggcggcag cctgcgtctg      60
agctgcgcgg cctccggatt tacctttct aattatggta tgcattgggt gcgccaagcc     120
cctgggaagg gtctcgagtg ggtgagcaat atccgttctg atggtagctg gacctattat     180
gcggatagcg tgaaaggccg ttttaccatt tcacgtgata attcgaaaaa caccctgtat     240
ctgcaaatga acagcctgcg tgcggaagat acggccgtgt attattgcgc gcgtcgttat     300
tggtctaagt ctcatgcttc tgttactgat tattggggcc aaggcaccct ggtgacggtt     360
agctca                                                                 366
```

<210> SEQ ID NO 3
<211> LENGTH: 366
<212> TYPE: DNA
<213> ORGANISM: Homo sapiens

<400> SEQUENCE: 3

```
caggtgcaat tggtggaaag cggcggcggc ctggtgcaac cgggcggcag cctgcgtctg      60
agctgcgcgg cctccggatt tacctttct tcttatggta tgcattgggt gcgccaagcc     120
cctgggaagg gtctcgagtg ggtgagcaat atctattctg atggtagcaa tacctttat     180
gcggatagcg tgaaaggccg ttttaccatt tcacgtgata attcgaaaaa caccctgtat     240
ctgcaaatga acagcctgcg tgcggaagat acggccgtgt attattgcgc gcgtaatatg     300
tatcgttggc cttttcatta tttttttgat tattggggcc aaggcaccct ggtgacggtt     360
agctca                                                                 366
```

<210> SEQ ID NO 4
<211> LENGTH: 357
<212> TYPE: DNA
<213> ORGANISM: Homo sapiens

<400> SEQUENCE: 4

```
caggtgcaat tggtggaaag cggcggcggc ctggtgcaac cgggcggcag cctgcgtctg      60
```

```
agctgcgcgg cctccggatt tacctttct tctaatggta tgtcttgggt gcgccaagcc      120
cctgggaagg gtctcgagtg ggtgagcaat atctcttatc tttctagctc tacctattat     180
gcggatagcg tgaaaggccg ttttaccatt tcacgtgata attcgaaaaa caccctgtat     240
ctgcaaatga acagcctgcg tgcggaagat acggccgtgt attattgcgc gcgttttat     300 ggttatttta attatgctga tgtttggggc caaggcaccc tggtgacggt tagctca       357
```

<210> SEQ ID NO 5
<211> LENGTH: 121
<212> TYPE: PRT
<213> ORGANISM: Homo sapiens

<400> SEQUENCE: 5

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
            20                  25                  30

Ser Ile Asn Trp Val Arg Gln Ala Pro Gly Gln Gly Leu Glu Trp Met
        35                  40                  45

Gly Tyr Ile Asp Pro Asn Arg Gly Asn Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Tyr Ile Tyr Phe Ile His Gly Met Leu Asp Phe Trp Gly
            100                 105                 110

Gln Gly Thr Leu Val Thr Val Ser Ser
        115                 120

<210> SEQ ID NO 6
<211> LENGTH: 122
<212> TYPE: PRT
<213> ORGANISM: Homo sapiens

<400> SEQUENCE: 6

Gln Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ser Asn Ile Arg Ser Asp Gly Ser Trp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Tyr Trp Ser Lys Ser His Ala Ser Val Thr Asp Tyr Trp
            100                 105                 110

Gly Gln Gly Thr Leu Val Thr Val Ser Ser
        115                 120

<210> SEQ ID NO 7
<211> LENGTH: 122
<212> TYPE: PRT
<213> ORGANISM: Homo sapiens

<400> SEQUENCE: 7

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ser Asn Ile Tyr Ser Asp Gly Ser Asn Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Met Tyr Arg Trp Pro Phe His Tyr Phe Phe Asp Tyr Trp
            100                 105                 110

Gly Gln Gly Thr Leu Val Thr Val Ser Ser
        115                 120

<210> SEQ ID NO 8
<211> LENGTH: 119
<212> TYPE: PRT
<213> ORGANISM: Homo sapiens

<400> SEQUENCE: 8

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Asn
            20                  25                  30

Gly Met Ser Trp Val Arg Gln Ala Pro Gly Lys Gly Leu Glu Trp Val
        35                  40                  45

Ser Asn Ile Ser Tyr Leu Ser Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Tyr Gly Tyr Phe Asn Tyr Ala Asp Val Trp Gly Gln Gly
            100                 105                 110

Thr Leu Val Thr Val Ser Ser
        115

<210> SEQ ID NO 9
<211> LENGTH: 342
<212> TYPE: DNA
<213> ORGANISM: Homo sapiens

<400> SEQUENCE: 9
gatatcgtga tgacccagag cccactgagc ctgccagtga ctccgggcga gcctgcgagc      60
attagctgca gaagcagcca aagcctgctt tttattgatg caataatta tctgaattgg     120 taccttcaaa aaccaggtca agcccgcag ctattaattt atcttggttc taatcgtgcc     180
agtggggtcc cggatcgttt tagcggctct ggatccggca ccgattttac cctgaaaatt     240
agccgtgtgg aagctgaaga cgtgggcgtg tattattgcc agcagtattc ttctaagtct     300
gctacctttg gccagggtac gaaagttgaa attaaacgta cg                        342

<210> SEQ ID NO 10

```
<211> LENGTH: 327
<212> TYPE: DNA
<213> ORGANISM: Homo sapiens

<400> SEQUENCE: 10
gatatccaga tgacccagag cccgtctagc ctgagcgcga gcgtgggtga tcgtgtgacc      60
attacctgca gagcgagcca ggatatttct gcttttctga attggtacca gcagaaacca     120
ggtaaagcac cgaaactatt aatttataag gtttctaatt tgcaaagcgg ggtcccgtcc     180
cgttttagcg gctctggatc cggcactgat tttaccctga ccattagcag cctgcaacct     240
gaagactttg cgacttatta ttgccagcag gcttattctg ttctattac ctttggccag      300 ggtacgaaag ttgaaattaa acgtacg                                         327

<210> SEQ ID NO 11
<211> LENGTH: 324
<212> TYPE: DNA
<213> ORGANISM: Homo sapiens

<400> SEQUENCE: 11
gatatcgaac tgacccagcc gccttcagtg agcgttgcac caggtcagac cgcgcgtatc      60
tcgtgtagcg gcgataatat tggtaataag tatgtttctt ggtaccagca gaaacccggg     120
caggcgccag ttgttgtgat ttatggtgat aataatcgtc cctcaggcat cccgaacgc      180 tttagcggat ccaacagcgg caacaccgcg accctgacca ttagcggcac tcaggcggaa     240
gacgaagcgg attattattg ctcttcttat gattcttctt attttgtgtt tggcggcggc     300
acgaagttaa ccgttcttgg ccag                                            324

<210> SEQ ID NO 12
<211> LENGTH: 327
<212> TYPE: DNA
<213> ORGANISM: Homo sapiens

<400> SEQUENCE: 12
gatatcgaac tgacccagcc gccttcagtg agcgttgcac caggtcagac cgcgcgtatc      60
tcgtgtagcg gcgataatat tggtcattat tatgcttctt ggtaccagca gaaacccggg     120
caggcgccag ttcttgtgat ttatcgtgat aatgatcgtc cctcaggcat cccggaacgc     180
tttagcggat ccaacagcgg caacaccgcg accctgacca ttagcggcac tcaggcggaa     240
gacgaagcgg attattattg ccagtcttat gattatcttc atgattttgt gtttggcggc     300
ggcacgaagt taaccgttct tggccag                                         327

<210> SEQ ID NO 13
<211> LENGTH: 114
<212> TYPE: PRT
<213> ORGANISM: Homo sapiens

<400> SEQUENCE: 13

Asp Ile Val Met Thr Gln Ser Pro Leu Ser Leu Pro Val Thr Pro Gly
  1               5                  10                  15

Glu Pro Ala Ser Ile Ser Cys Arg Ser Ser Gln Ser Leu Leu Phe Ile
             20                  25                  30

Asp Gly Asn Asn Tyr Leu Asn Trp Tyr Leu Gln Lys Pro Gly Gln Ser
         35                  40                  45

Pro Gln Leu Leu Ile Tyr Leu Gly Ser Asn Arg Ala Ser Gly Val Pro
     50                  55                  60

Asp Arg Phe Ser Gly Ser Gly Ser Gly Thr Asp Phe Thr Leu Lys Ile
 65                  70                  75                  80
```

Ser Arg Val Glu Ala Glu Asp Val Gly Val Tyr Tyr Cys Gln Gln Tyr
                85                  90                  95

Ser Ser Lys Ser Ala Thr Phe Gly Gln Gly Thr Lys Val Glu Ile Lys
            100                 105                 110

Arg Thr

<210> SEQ ID NO 14
<211> LENGTH: 109
<212> TYPE: PRT
<213> ORGANISM: Homo sapiens

<400> SEQUENCE: 14

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Ser Ala Phe
             20                  25                  30

Leu Asn Trp Tyr Gln Gln Lys Pro Gly Lys Ala Pro Lys Leu Leu Ile
         35                  40                  45

Tyr Lys Val Ser Asn Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Tyr Ser Gly Ser Ile
                 85                  90                  95

Thr Phe Gly Gln Gly Thr Lys Val Glu Ile Lys Arg Thr
            100                 105

<210> SEQ ID NO 15
<211> LENGTH: 108
<212> TYPE: PRT
<213> ORGANISM: Homo sapiens

<400> SEQUENCE: 15

Asp Ile Glu Leu Thr Gln Pro Pro Ser Val Ser Val Ala Pro Gly Gln
 1               5                  10                  15

Thr Ala Arg Ile Ser Cys Ser Gly Asp Asn Ile Gly Asn Lys Tyr Val
             20                  25                  30

Ser Trp Tyr Gln Gln Lys Pro Gly Gln Ala Pro Val Val Val Ile Tyr
         35                  40                  45

Gly Asp Asn Asn Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Glu
 65                  70                  75                  80

Asp Glu Ala Asp Tyr Tyr Cys Ser Ser Tyr Asp Ser Ser Tyr Phe Val
                 85                  90                  95

Phe Gly Gly Gly Thr Lys Leu Thr Val Leu Gly Gln
            100                 105

<210> SEQ ID NO 16
<211> LENGTH: 109
<212> TYPE: PRT
<213> ORGANISM: Homo sapiens

<400> SEQUENCE: 16

Asp Ile Glu Leu Thr Gln Pro Pro Ser Val Ser Val Ala Pro Gly Gln
 1               5                  10                  15

Thr Ala Arg Ile Ser Cys Ser Gly Asp Asn Ile Gly His Tyr Tyr Ala
             20                  25                  30

```
Ser Trp Tyr Gln Gln Lys Pro Gly Gln Ala Pro Val Leu Val Ile Tyr
            35                  40                  45

Arg Asp Asn Asp Arg Pro Ser Gly Ile Pro Glu Arg Phe Ser Gly Ser
            50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Tyr Asp Tyr Leu His Asp Phe
                85                  90                  95

Val Phe Gly Gly Gly Thr Lys Leu Thr Val Leu Gly Gln
                100                 105

<210> SEQ ID NO 17
<211> LENGTH: 120
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 17

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Gly Gly Asp Gly Phe Tyr Ala Met Asp Tyr Trp Gly Gln
                100                 105                 110

Gly Thr Leu Val Thr Val Ser Ser
            115                 120

<210> SEQ ID NO 18
<211> LENGTH: 120
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 18

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Ala Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 19
<211> LENGTH: 107
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 19

Ser Tyr Glu Leu Thr Gln Pro Pro Ser Val Ser Val Ala Pro Gly Gln
  1               5                  10                  15

Thr Ala Arg Ile Ser Cys Ser Gly Asp Ala Leu Gly Asp Lys Tyr Ala
             20                  25                  30

Ser Trp Tyr Gln Gln Lys Pro Gly Gln Ala Pro Val Leu Val Ile Tyr
         35                  40                  45

Asp Asp Ser Asp Arg Pro Ser Gly Ile Pro Glu Arg Phe Ser Gly Ser
     50                  55                  60

Asn Ser Gly Asn Thr Ala Thr Leu Thr Ile Ser Gly Thr Gln Ala Glu
 65                  70                  75                  80

Asp Glu Ala Asp Tyr Tyr Cys Gln Gln His Tyr Thr Thr Pro Pro Val
                 85                  90                  95

Phe Gly Gly Gly Thr Lys Leu Thr Val Leu Gly
            100                 105

<210> SEQ ID NO 20
<211> LENGTH: 108
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 20

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Ser Ser Tyr
             20                  25                  30

Leu Ala Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                 85                  90                  95

Thr Phe Gly Gln Gly Thr Lys Val Glu Ile Lys Arg
            100                 105

<210> SEQ ID NO 21
<211> LENGTH: 113
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 21
```

```
Asp Ile Val Met Thr Gln Ser Pro Leu Ser Leu Pro Val Thr Pro Gly
  1               5                  10                  15

Glu Pro Ala Ser Ile Ser Cys Arg Ser Ser Gln Ser Leu Leu His Ser
             20                  25                  30

Asn Gly Tyr Asn Tyr Leu Asp Trp Tyr Leu Gln Lys Pro Gly Gln Ser
         35                  40                  45

Pro Gln Leu Leu Ile Tyr Leu Gly Ser Asn Arg Ala Ser Gly Val Pro
     50                  55                  60

Asp Arg Phe Ser Gly Ser Gly Ser Gly Thr Asp Phe Thr Leu Lys Ile
 65              70                  75                  80

Ser Arg Val Glu Ala Glu Asp Val Gly Val Tyr Tyr Cys Gln Gln His
                 85                  90                  95

Tyr Thr Thr Pro Pro Thr Phe Gly Gln Gly Thr Lys Val Glu Ile Lys
                100                 105                 110

Arg
```

<210> SEQ ID NO 22
<211> LENGTH: 300
<212> TYPE: PRT
<213> ORGANISM: Homo sapiens

<400> SEQUENCE: 22

```
Met Ala Asn Cys Glu Phe Ser Pro Val Ser Gly Asp Lys Pro Cys Cys
  1               5                  10                  15

Arg Leu Ser Arg Arg Ala Gln Leu Cys Leu Gly Val Ser Ile Leu Val
             20                  25                  30

Leu Ile Leu Val Val Val Leu Ala Val Val Val Pro Arg Trp Arg Gln
         35                  40                  45

Gln Trp Ser Gly Pro Gly Thr Thr Lys Arg Phe Pro Glu Thr Val Leu
     50                  55                  60

Ala Arg Cys Val Lys Tyr Thr Glu Ile His Pro Glu Met Arg His Val
 65              70                  75                  80

Asp Cys Gln Ser Val Trp Asp Ala Phe Lys Gly Ala Phe Ile Ser Lys
                 85                  90                  95

His Pro Cys Asn Ile Thr Glu Glu Asp Tyr Gln Pro Leu Met Lys Leu
                100                 105                 110

Gly Thr Gln Thr Val Pro Cys Asn Lys Ile Leu Leu Trp Ser Arg Ile
            115                 120                 125

Lys Asp Leu Ala His Gln Phe Thr Gln Val Gln Arg Asp Met Phe Thr
130                 135                 140

Leu Glu Asp Thr Leu Leu Gly Tyr Leu Ala Asp Asp Leu Thr Trp Cys
145                 150                 155                 160

Gly Glu Phe Asn Thr Ser Lys Ile Asn Tyr Gln Ser Cys Pro Asp Trp
                165                 170                 175

Arg Lys Asp Cys Ser Asn Asn Pro Val Ser Val Phe Trp Lys Thr Val
            180                 185                 190

Ser Arg Arg Phe Ala Glu Ala Ala Cys Asp Val Val His Val Met Leu
        195                 200                 205

Asn Gly Ser Arg Ser Lys Ile Phe Asp Lys Asn Ser Thr Phe Gly Ser
    210                 215                 220

Val Glu Val His Asn Leu Gln Pro Glu Lys Val Gln Thr Leu Glu Ala
225                 230                 235                 240

Trp Val Ile His Gly Gly Arg Glu Asp Ser Arg Asp Leu Cys Gln Asp
                245                 250                 255
```

```
Pro Thr Ile Lys Glu Leu Glu Ser Ile Ile Ser Lys Arg Asn Ile Gln
        260                 265                 270

Phe Ser Cys Lys Asn Ile Tyr Arg Pro Asp Lys Phe Leu Gln Cys Val
        275                 280                 285

Lys Asn Pro Glu Asp Ser Ser Cys Thr Ser Glu Ile
        290                 295                 300

<210> SEQ ID NO 23
<211> LENGTH: 1317
<212> TYPE: DNA
<213> ORGANISM: Homo sapiens

<400> SEQUENCE: 23
caggtggaat tggtggaatc tggaggatcc ctgaaactct cctgtgcagc ctcaggattc      60
gattttagta gatcctggat gaattgggtc cggcaggctc caggaaaagg gctagaatgg     120
attggagaaa ttaatccaga tagcagtacg ataaactata cgacatctct aaaggataaa     180
ttcatcatct ccagagacaa cgccaaaaat acgctgtacc tgcaaatgac caaagtgaga     240
tctgaggaca cagccctttta ttactgtgca agatatggta actggtttcc ttattggggc     300
caagggactc tggtcactgt cagctcagcc tccaccaagg gtccatcggt cttccccctg     360
gcaccctcct ccaagagcac ctctgggggc acagcggccc tgggctgcct ggtcaaggac     420
tacttccccg aaccggtgac ggtgtcgtgg aactcaggcg ccctgaccag cggcgtgcac     480
accttcccgg ctgtcctaca gtcctcagga ctctactccc tcagcagcgt ggtgaccgtg     540
ccctccagca gcttgggcac ccagacctac atctgcaacg tgaatcacaa gcccagcaac     600
accaaggtgg acaagaaagt tgagcccaaa tcttgtgaca aaactcacac atgcccaccg     660
tgcccagcac ctgaactcct ggggggaccg tcagtcttcc tcttcccccc aaaacccaag     720
gacaccctca tgatctcccg gacccctgag gtcacatgcg tggtggtgga cgtgagccac     780
gaagaccctg aggtcaagtt caactggtac gtggacggcg tggaggtgca taatgccaag     840
acaaagccgc gggaggagca gtacaacagc acgtaccggg tggtcagcgt cctcaccgtc     900
ctgcaccagg actggctgaa tggcaaggag tacaagtgca aggtctccaa caaagccctc     960
ccagccccca tcgagaaaac catctccaaa gccaaagggc agccccgaga accacaggtg    1020
tacaccctgc ccccatcccg ggatgagctg accaagaacc aggtcagcct gacctgcctg    1080
gtcaaaggct tctatcccag cgacatcgcc gtggagtggg agagcaatgg gcagccggag    1140
aacaactaca agaccacgcc tcccgtgctg gactccgacg gctccttctt cctctacagc    1200
aagctcaccg tggacaagag caggtggcag caggggaacg tcttctcatg ctccgtgatg    1260
catgaggctc tgcacaacca ctacacgcag aagagcctct ccctgtctcc gggtaaa       1317

<210> SEQ ID NO 24
<211> LENGTH: 642
<212> TYPE: DNA
<213> ORGANISM: Homo sapiens

<400> SEQUENCE: 24
gatatcctga tgacccagtc tcaaaaaatc atgcccacat cagtgggaga cagggtcagc      60
gtcacctgca aggccagtca aaatgtggat actaatgtag cctggtatca acagaaacca     120
ggacagtctc ctaaagcact gatttactcg gcatcctacc gatacagtgg agtccctgat     180
cgcttcacag gcagtggatc tgggacagat ttcactctca ccatcaccaa tgtgcagtct     240
gaggacttgg cagagtattt ctgtcagcaa tatgacagct atcctctcac gttcggtgct     300
gggaccaagc tggacctgaa acgtacggtg gctgcaccat ctgtcttcat cttcccgcca     360
```

```
tctgatgagc agttgaaatc tggaactgcc tctgttgtgt gcctgctgaa taacttctat      420
cccagagagg ccaaagtaca gtggaaggtg ataacgccc tccaatcggg taactcccag       480
gagagtgtca cagagcagga cagcaaggac agcacctaca gcctcagcag caccctgacg      540
ctgagcaaag cagactacga gaaacacaaa gtctacgcct gcgaagtcac ccatcagggc      600
ctgagctcgc ccgtcacaaa gagcttcaac aggggagagt gt                        642
```

```
<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
atggccaact gcgagttcag c                                               21

<210> SEQ ID NO 26
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
tcagatctca gatgtgcaag atgaatc                                         27

<210> SEQ ID NO 27
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ttggtaccag gtggcgccag cagtg                                           25

<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ttggtaccat ggccaactgc gag                                             23

<210> SEQ ID NO 29
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ccgatatcag atctcagatg tgcaagatg                                       29

<210> SEQ ID NO 30
<211> LENGTH: 28
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 30
ccgatatcga tctcagatgt gcaagatg                                           28

<210> SEQ ID NO 31
<211> LENGTH: 363
<212> TYPE: DNA
<213> ORGANISM: Homo sapiens

<400> SEQUENCE: 31
caggtgcaat tagtccaaag tggtgcggaa gtgaaaaaac cgggcgcgag cgtgaaagtg         60
agctgcaaag cctccggata tacctttact tcttattcta ttaattgggt ccgccaagcc        120
cctgggcagg gtctcgagtg gatgggctat atcgatccga atcgtggcaa tacgaattac        180
gcgcagaagt ttcagggccg ggtgaccatg acccgtgata ccagcattag caccgcgtat        240
atggaactga gcagcctgcg tagcgaagat acggccgtgt attattgcgc gcgtgagtat        300
atttatttta tcatggtat gcttgatttt tggggccaag gcaccctggt gacggttagc        360
tca                                                                     363

<210> SEQ ID NO 32
<211> LENGTH: 1500
<212> TYPE: DNA
<213> ORGANISM: Artificial Sequence
<220> FEATURE:
<223> OTHER INFORMATION: Description of Artificial Sequence: Synthetic
      nucleotide construct
<220> FEATURE:
<221> NAME/KEY: CDS
<222> LOCATION: (307)..(393)

<400> SEQUENCE: 32
tcgctattac catggtgatg cggttttggc agtacatcaa tgggcgtgga tagcggtttg         60
actcacgggg atttccaagt ctccaccccca ttgacgtcaa tgggagtttg ttttggcacc       120
aaaatcaacg ggactttcca aatgtcgta acaactccgc cccattgacg caaatgggcg        180
gtaggcgtgt acggtgggag gtctatataa gcagagctct ctggctaact agagaaccca        240
ctgcttactg gcttatcgaa attaatacga ctcactatag ggagacccaa gctggctagc        300 gccacc atg aaa cac ctg tgg ttc ttc ctc ctg ctg gtg gca gct ccc          348
       Met Lys His Leu Trp Phe Phe Leu Leu Leu Val Ala Ala Pro
         1               5                  10 aga tgg gtc ctg tcc cag gtg gaa ttc tgc agg cgg tta gct cag            393
Arg Trp Val Leu Ser Gln Val Glu Phe Cys Arg Arg Leu Ala Gln
 15                  20                  25 cctccaccaa gggtccatcg gtcttccccc tggcaccctc ctccaagagc acctctgggg       453
gcacagcggc cctgggctgc ctggtcaagg actacttccc cgaaccggtg acggtgtcgt       513
ggaactcagg cgccctgacc agcggcgtgc acaccttccc ggctgtccta cagtcctcag       573
gactctactc cctcagcagc gtggtgaccg tgccctccag cagcttgggc acccagacct       633
acatctgcaa cgtgaatcac aagcccagca caccaaggt ggacaagaaa gttgagccca        693
aatcttgtga caaaactcac acatgcccac cgtgcccagc acctgaactc ctggggggac       753
cgtcagtctt cctcttcccc ccaaaaccca aggacaccct catgatctcc cggacccctg       813
aggtcacatg cgtggtggtg gacgtgagcc acgaagaccc tgaggtcaag ttcaactggt       873
acgtggacgg cgtggaggtg cataatgcca agacaaagcc gcgggaggag cagtacaaca       933
```

-continued

```
gcacgtaccg ggtggtcagc gtcctcaccg tcctgcacca ggactggctg aatggcaagg      993
agtacaagtg caaggtctcc aacaaagccc tcccagcccc catcgagaaa accatctcca     1053
aagccaaagg gcagcccga gaaccacagg tgtacaccct gcccccatcc cgggatgagc      1113
tgaccaagaa ccaggtcagc ctgacctgcc tggtcaaagg cttctatccc agcgacatcg     1173
ccgtggagtg ggagagcaat gggcagccgg agaacaacta caagaccacg cctcccgtgc     1233
tggactccga cggctccttc ttcctctaca gcaagctcac cgtggacaag agcaggtggc     1293
agcaggggaa cgtcttctca tgctccgtga tgcatgaggc tctgcacaac cactacacgc     1353
agaagagcct ctccctgtct ccgggtaaat gagggcccgt ttaaacccgc tgatcagcct     1413
cgactgtgcc ttctagttgc cagccatctg ttgtttgccc ctccccgtg ccttccttga      1473 ccctggaagg tgccactccc actgtcc                                          1500
```

<210> SEQ ID NO 33
<211> LENGTH: 800
<212> TYPE: DNA
<213> ORGANISM: Artificial Sequence
<220> FEATURE:
<223> OTHER INFORMATION: Description of Artificial Sequence: Synthetic
      nucleotide construct
<220> FEATURE:
<221> NAME/KEY: CDS
<222> LOCATION: (307)..(705)

<400> SEQUENCE: 33

```
tcgctattac catggtgatg cggttttggc agtacatcaa tgggcgtgga tagcggtttg       60
actcacgggg atttccaagt ctccacccca ttgacgtcaa tgggagtttg ttttggcacc      120
aaaatcaacg ggactttcca aaatgtcgta acaactccgc cccattgacg caaatgggcg      180
gtaggcgtgt acggtgggag gtctatataa gcagagctct ctggctaact agagaaccca     240
ctgcttactg gcttatcgaa attaatacga ctcactatag ggagacccaa gctggctagc     300 gccacc atg gtg ttg cag acc cag gtc ttc att tct ctg ttg ctc tgg          348
       Met Val Leu Gln Thr Gln Val Phe Ile Ser Leu Leu Leu Trp
         1               5                  10 atc tct ggt gcc tac ggg gat atc gtg atg att aaa cgt acg gtg gct         396
Ile Ser Gly Ala Tyr Gly Asp Ile Val Met Ile Lys Arg Thr Val Ala
 15              20                  25                  30 gca cca tct gtc ttc atc ttc ccg cca tct gat gag cag ttg aaa tct         444
Ala Pro Ser Val Phe Ile Phe Pro Pro Ser Asp Glu Gln Leu Lys Ser
             35                  40                  45 gga act gcc tct gtt gtg tgc ctg ctg aat aac ttc tat ccc aga gag         492
Gly Thr Ala Ser Val Val Cys Leu Leu Asn Asn Phe Tyr Pro Arg Glu
         50                  55                  60 gcc aaa gta cag tgg aag gtg gat aac gcc ctc caa tcg ggt aac tcc         540
Ala Lys Val Gln Trp Lys Val Asp Asn Ala Leu Gln Ser Gly Asn Ser
     65                  70                  75 cag gag agt gtc aca gag cag gac agc aag gac agc acc tac agc ctc         588
Gln Glu Ser Val Thr Glu Gln Asp Ser Lys Asp Ser Thr Tyr Ser Leu
 80                  85                  90 agc agc acc ctg acg ctg agc aaa gca gac tac gag aaa cac aaa gtc         636
Ser Ser Thr Leu Thr Leu Ser Lys Ala Asp Tyr Glu Lys His Lys Val
 95                 100                 105                 110 tac gcc tgc gaa gtc acc cat cag ggc ctg agc tcg ccc gtc aca aag         684
Tyr Ala Cys Glu Val Thr His Gln Gly Leu Ser Ser Pro Val Thr Lys
            115                 120                 125 agc ttc aac agg gga gag tgt tagggcccg tttaaacccg ctgatcagcc             735
Ser Phe Asn Arg Gly Glu Cys
            130
```

```
tcgactgtgc cttctagttg ccagccatct gttgtttgcc cctccccgt gccttccttg    795 accct                                                                800

<210> SEQ ID NO 34
<211> LENGTH: 800
<212> TYPE: DNA
<213> ORGANISM: Artificial Sequence
<220> FEATURE:
<223> OTHER INFORMATION: Description of Artificial Sequence: Synthetic
      nucleotide construct
<220> FEATURE:
<221> NAME/KEY: CDS
<222> LOCATION: (307)..(384)
<220> FEATURE:
<221> NAME/KEY: CDS
<222> LOCATION: (386)..(712)

<400> SEQUENCE: 34
tcgctattac catggtgatg cggttttggc agtacatcaa tgggcgtgga tagcggtttg     60
actcacgggg atttccaagt ctccacccca ttgacgtcaa tgggagtttg ttttggcacc    120
aaaatcaacg ggactttcca aaatgtcgta acaactccgc cccattgacg caaatgggcg    180
gtaggcgtgt acggtgggag gtctatataa gcagagctct ctggctaact agagaaccca    240
ctgcttactg gcttatcgaa attaatacga ctcactatag ggagacccaa gctggctagc    300 gccacc atg gcc tgg gct ctg ctg ctc ctc acc ctc ctc act cag ggc      348
       Met Ala Trp Ala Leu Leu Leu Leu Thr Leu Leu Thr Gln Gly
         1               5                  10 aca gga tcc tgg gct gat atc gtg atg cac gaa gtt a acc gtc cta ggt   397
Thr Gly Ser Trp Ala Asp Ile Val Met His Glu Val   Thr Val Leu Gly
 15                  20                  25                      30 cag ccc aag gct gcc ccc tcg gtc act ctg ttc ccg ccc tcc tct gag     445
Gln Pro Lys Ala Ala Pro Ser Val Thr Leu Phe Pro Pro Ser Ser Glu
                 35                  40                  45 gag ctt caa gcc aac aag gcc aca ctg gtg tgt ctc ata agt gac ttc     493
Glu Leu Gln Ala Asn Lys Ala Thr Leu Val Cys Leu Ile Ser Asp Phe
             50                  55                  60 tac ccg gga gcc gtg aca gtg gcc tgg aag gga gat agc agc ccc gtc     541
Tyr Pro Gly Ala Val Thr Val Ala Trp Lys Gly Asp Ser Ser Pro Val
 65                  70                  75 aag gcg gga gtg gag acc acc aca ccc tcc aaa caa agc aac aac aag     589
Lys Ala Gly Val Glu Thr Thr Thr Pro Ser Lys Gln Ser Asn Asn Lys
         80                  85                  90 tac gcg gcc agc agc tat ctg agc ctg acg cct gag cag tgg aag tcc     637
Tyr Ala Ala Ser Ser Tyr Leu Ser Leu Thr Pro Glu Gln Trp Lys Ser
     95                 100                 105                 110 cac aga agc tac agc tgc cag gtc acg cat gaa ggg agc acc gtg gag     685
His Arg Ser Tyr Ser Cys Gln Val Thr His Glu Gly Ser Thr Val Glu
                115                 120                 125 aag aca gtg gcc cct aca gaa tgt tca tagggcccg tttaaacccg             732
Lys Thr Val Ala Pro Thr Glu Cys Ser
                130                 135 ctgatcagcc tcgactgtgc cttctagttg ccagccatct gttgtttgcc cctccccgt    792 gccttcct                                                            800

<210> SEQ ID NO 35
<211> LENGTH: 359
<212> TYPE: PRT
<213> ORGANISM: Artificial Sequence
<220> FEATURE:
<223> OTHER INFORMATION: Description of Artificial Sequence: Synthetic
      protein construct
```

<400> SEQUENCE: 35

```
Met Lys His Leu Trp Phe Phe Leu Leu Val Ala Ala Pro Arg Trp
 1               5                  10                  15
Val Leu Ser Gln Val Glu Phe Cys Arg Arg Leu Ala Gln Ala Ser Thr
                20                  25                  30
Lys Gly Pro Ser Val Phe Pro Leu Ala Pro Ser Ser Lys Ser Thr Ser
            35                  40                  45
Gly Gly Thr Ala Ala Leu Gly Cys Leu Val Lys Asp Tyr Phe Pro Glu
    50                  55                  60
Pro Val Thr Val Ser Trp Asn Ser Gly Ala Leu Thr Ser Gly Val His
65                  70                  75                  80
Thr Phe Pro Ala Val Leu Gln Ser Ser Gly Leu Tyr Ser Leu Ser Ser
                85                  90                  95
Val Val Thr Val Pro Ser Ser Ser Leu Gly Thr Gln Thr Tyr Ile Cys
            100                 105                 110
Asn Val Asn His Lys Pro Ser Asn Thr Lys Val Asp Lys Lys Val Glu
        115                 120                 125
Pro Lys Ser Cys Asp Lys Thr His Thr Cys Pro Pro Cys Pro Ala Pro
    130                 135                 140
Glu Leu Leu Gly Gly Pro Ser Val Phe Leu Phe Pro Pro Lys Pro Lys
145                 150                 155                 160
Asp Thr Leu Met Ile Ser Arg Thr Pro Glu Val Thr Cys Val Val Val
                165                 170                 175
Asp Val Ser His Glu Asp Pro Glu Val Lys Phe Asn Trp Tyr Val Asp
            180                 185                 190
Gly Val Glu Val His Asn Ala Lys Thr Lys Pro Arg Glu Glu Gln Tyr
        195                 200                 205
Asn Ser Thr Tyr Arg Val Val Ser Val Leu Thr Val Leu His Gln Asp
    210                 215                 220
Trp Leu Asn Gly Lys Glu Tyr Lys Cys Lys Val Ser Asn Lys Ala Leu
225                 230                 235                 240
Pro Ala Pro Ile Glu Lys Thr Ile Ser Lys Ala Lys Gly Gln Pro Arg
                245                 250                 255
Glu Pro Gln Val Tyr Thr Leu Pro Pro Ser Arg Asp Glu Leu Thr Lys
            260                 265                 270
Asn Gln Val Ser Leu Thr Cys Leu Val Lys Gly Phe Tyr Pro Ser Asp
        275                 280                 285
Ile Ala Val Glu Trp Glu Ser Asn Gly Gln Pro Glu Asn Asn Tyr Lys
    290                 295                 300
Thr Thr Pro Pro Val Leu Asp Ser Asp Gly Ser Phe Phe Leu Tyr Ser
305                 310                 315                 320
Lys Leu Thr Val Asp Lys Ser Arg Trp Gln Gln Gly Asn Val Phe Ser
                325                 330                 335
Cys Ser Val Met His Glu Ala Leu His Asn His Tyr Thr Gln Lys Ser
            340                 345                 350
Leu Ser Leu Ser Pro Gly Lys
        355
```

<210> SEQ ID NO 36
<211> LENGTH: 133
<212> TYPE: PRT
<213> ORGANISM: Artificial Sequence
<220> FEATURE:
<223> OTHER INFORMATION: Description of Artificial Sequence: Synthetic protein construct

```
<400> SEQUENCE: 36

Met Val Leu Gln Thr Gln Val Phe Ile Ser Leu Leu Leu Trp Ile Ser
 1               5                  10                  15

Gly Ala Tyr Gly Asp Ile Val Met Ile Lys Arg Thr Val Ala Ala Pro
                20                  25                  30

Ser Val Phe Ile Phe Pro Pro Ser Asp Glu Gln Leu Lys Ser Gly Thr
            35                  40                  45

Ala Ser Val Val Cys Leu Leu Asn Asn Phe Tyr Pro Arg Glu Ala Lys
        50                  55                  60

Val Gln Trp Lys Val Asp Asn Ala Leu Gln Ser Gly Asn Ser Gln Glu
 65                  70                  75                  80

Ser Val Thr Glu Gln Asp Ser Lys Asp Ser Thr Tyr Ser Leu Ser Ser
                85                  90                  95

Thr Leu Thr Leu Ser Lys Ala Asp Tyr Glu Lys His Lys Val Tyr Ala
            100                 105                 110

Cys Glu Val Thr His Gln Gly Leu Ser Ser Pro Val Thr Lys Ser Phe
        115                 120                 125

Asn Arg Gly Glu Cys
    130

<210> SEQ ID NO 37
<211> LENGTH: 135
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 37

Met Ala Trp Ala Leu Leu Leu Leu Thr Leu Leu Thr Gln Gly Thr Gly
 1               5                  10                  15

Ser Trp Ala Asp Ile Val Met His Glu Val Thr Val Leu Gly Gln Pro
                20                  25                  30

Lys Ala Ala Pro Ser Val Thr Leu Phe Pro Pro Ser Ser Glu Glu Leu
            35                  40                  45

Gln Ala Asn Lys Ala Thr Leu Val Cys Leu Ile Ser Asp Phe Tyr Pro
        50                  55                  60

Gly Ala Val Thr Val Ala Trp Lys Gly Asp Ser Ser Pro Val Lys Ala
 65                  70                  75                  80

Gly Val Glu Thr Thr Thr Pro Ser Lys Gln Ser Asn Asn Lys Tyr Ala
                85                  90                  95

Ala Ser Ser Tyr Leu Ser Leu Thr Pro Glu Gln Trp Lys Ser His Arg
            100                 105                 110

Ser Tyr Ser Cys Gln Val Thr His Glu Gly Ser Thr Val Glu Lys Thr
        115                 120                 125

Val Ala Pro Thr Glu Cys Ser
    130                 135

<210> SEQ ID NO 38
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Val Ser Arg Arg Phe Ala Glu Ala Ala Cys Asp Val Val His Val
```

<210> SEQ ID NO 39
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 39

Phe Leu Gln Cys Val Lys Asn Pro Glu Asp Ser Ser Cys Thr Ser
 1               5                  10                  15

<210> SEQ ID NO 40
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 40

Cys Gln Ser Val Trp Asp Ala Phe Lys Gly Ala Phe Ile
 1               5                  10

<210> SEQ ID NO 41
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 41

Thr Trp Cys Gly Glu Phe Asn Thr Ser Lys Ile Asn Tyr
 1               5                  10

<210> SEQ ID NO 42
<211> LENGTH: 120
<212> TYPE: PRT
<213> ORGANISM: Homo sapiens

<400> SEQUENCE: 42

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 43
<211> LENGTH: 113
<212> TYPE: PRT

-continued

```
<213> ORGANISM: Homo sapiens

<400> SEQUENCE: 43

Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gln Gln His
                85                  90                  95

Tyr Thr Thr Pro Pro Thr Phe Gly Gln Gly Thr Lys Leu Glu Ile Lys
            100                 105                 110

Arg
```

ANTI-CD38 HUMAN ANTIBODIES AND USES THEREOF

This application claims priority to U.S. provisional application Nos. 60/541,911 filed Feb. 6, 2004, 60/547,584 filed Feb. 26, 2004, 60/553,948 filed Mar. 18, 2004, and 60/599,014 filed Aug. 6, 2004, the contents of which are incorporated herein in their entirety.

BACKGROUND OF THE INVENTION

CD38 is a type-II membrane glycoprotein and belongs to the family of ectoenzymes, due to its enzymatic activity as ADP ribosyl-cyclase and cADP—hydrolase. During ontogeny, CD38 appears on CD34+ committed stem cells and lineage-committed progenitors of lymphoid, erythroid and myeloid cells. It is understood that CD38 expression persists only in the lymphoid lineage, through the early stages of T- and B-cell development.

The up-regulation of CD38 serves as a marker for lymphocyte activation—in particular B-cell differentiation along the plasmacytoid pathway. (Co-)receptor functions of CD38 leading to intracellular signaling or intercellular communication via its ligand, CD31, are postulated, as well as its role as an intracellular regulator of a second messenger, cyclic ADPr, in a variety of signaling cascades. However, its physiological importance remains to be elucidated, since knock out of the murine analogue or anti-CD38 auto-antibodies in humans do not appear to be detrimental.

Apart from observing its expression in the hematopoetic system, researchers have noted the up-regulation of CD38 on various cell-lines derived from B-, T-, and myeloid/monocytic tumors, including B- or T-cell acute lymphoblastic leukemia (ALL), acute myeloid leukemia (AML), Non-Hodgkin's lymphoma (NHL) and multiple myelonia (MM). In MM, for example, strong CD38 expression is witnessed in the majority of all patient samples.

Hence, over-expression of CD38 on malignant cells provides an attractive therapeutic target for immunotherapy. Of special attraction is the fact that the most primitive pluripotent stem cells of the hematopoietic system are CD38-negative and that the extent of cytotoxic effects by ADCC or CDC correlates well with the expression-levels of the respective target.

Current approaches of anti-CD38 therapies can be divided in two groups: in vivo and ex vivo approaches. In in vivo approaches, anti-CD38 antibodies are administered to a subject in need of therapy in order to cause the antibody-mediated depletion of CD38-overexpressing malignant cells. Depletion can either be achieved by antibody-mediated ADCC and/or CDC by effector cells, or by using the anti-CD38 antibodies as targeting moieties for the transport of cytotoxic substances, e.g. saporin, to the target cells, and subsequent internalization. In the ex vivo approach, cell population, e.g. bone marrow cells, comprising CD38 overexpressing malignant cells are removed from an individual in need of treatment and are contacted with anti-CD38 antibodies. The target cells are either destroyed by cytotoxic substances, e.g. saporin, as described for the in vivo approach, or are removed by contacting the cell population with immobilized anti-CD38 antibodies, thus removing CD38 overexpressing target cells from the mixture. Thereafter, the depleted cell population is reinserted into the patient.

Antibodies specific for CD38 can be divided in different groups, depending on various properties. Binding of some antibodies to the CD38 molecule (predominantly aa 220-300) can trigger activities within the target cell, such as Ca2+ release, cytokine release, phosphorylation events and growth stimulation based on the respective antibody specificity (Konopleva et al., 1998; Ausiello et al., 2000), but no clear correlation between the binding site of the various known antibodies and their (non-)agonistic properties could be seen (Funaro et al., 1990).

Relatively little is known about the efficacy of published anti-CD38 antibodies. What is known is that all known antibodies seem to exclusively recognize epitopes (amino acid residues 220 to 300) located in the C-terminal part of CD38. No antibodies are known so far that are specific for epitopes in the N-terminal part of CD38 distant from the active site in the primary protein sequence. However, we have found that OKT10, which has been in clinical testing, has a relatively low affinity and efficacy when analyzed as chimeric construct comprising a human Fc part. Furthermore, OKT10 is a murine antibody rendering it unsuitable for human administration. A human anti-CD38 scFv antibody fragment has recently been described (WO 02/06347). However, that antibody is specific for a selectively expressed CD38 epitope.

Correspondingly, in light of the great potential for anti-CD38 antibody therapy, there is a high need for human anti-CD38 antibodies with high affinity and with high efficacy in mediating killing of CD38 overexpressing malignant cells by ADCC and/or CDC.

The present invention satisfies these and other needs by providing fully human and highly efficacious anti-CD38 antibodies, which are described below.

SUMMARY OF THE INVENTION

It is an object of the invention to provide human and humanized antibodies that can effectively mediate the killing of CD38-overexpressing cells.

It is another object of the invention to provide antibodies that are safe for human administration.

It is also an object of the present invention to provide methods for treating disease or and/or conditions associated with CD38 up-regulation by using one or more antibodies of the invention. These and other objects of the invention are more fully described herein.

In one aspect, the invention provides an isolated antibody or functional antibody fragment that contains an antigen-binding region that is specific for an epitope of CD38, where the antibody or functional fragment thereof is able to mediate killing of a CD38+ target cell (LP-1 (DSMZ: ACC41) and RPMI-8226 (ATCC: CCL-155)) by antibody-dependent cellular cytotoxicity ("ADCC") with an at least two- to five-fold better efficacy than the chimeric OKT10 antibody having SEQ ID NOS: 23 and 24 (under the same or substantially the same conditions), when a human PBMC cell is employed as an effector cell, and when the ratio of effector cells to target cells is between about 30:1 and about 50:1. Such an antibody or functional fragment thereof may contain an antigen-binding region that contains an H-CDR3 region depicted in SEQ ID NO: 5, 6, 7, or 8; the antigen-binding region may further include an H-CDR2 region depicted in SEQ ID NO: 5, 6, 7, or 8; and the antigen-binding region also may contain an H-CDR1 region depicted in SEQ ID NO: 5, 6, 7, or 8. Such a CD38-specific antibody of the invention may contain an antigen-binding region that contains an L-CDR3 region depicted in SEQ ID NO: 13, 14, 15, or 16; the antigen-binding region may further include an L-CDR1 region depicted in SEQ ID NO: 13, 14, 15, or 16; and the antigen-binding region also may contain an L-CDR2 region depicted in SEQ ID NO: 13, 14, 15, or 16.

In another aspect, the invention provides an isolated antibody or functional antibody fragment that contains an antigen-binding region that is specific for an epitope of CD38, where the antibody or functional fragment thereof is able to mediate killing of a CD38-transfected CHO cell by CDC with an at least two-fold better efficacy than chimeric OKT10 (SEQ ID NOS: 23 and 24) under the same or substantially the same conditions as in the previous paragraph. An antibody satisfying these criteria may contain an antigen-binding region that contains an H-CDR3 region depicted in SEQ ID NO: 5, 6, or 7; the antigen-binding region may further include an H-CDR2 region depicted in SEQ ID NO: 5, 6, or 7; and the antigen-binding region also may contain an H-CDR1 region depicted in SEQ ID NO: 5, 6, or 7. Such a CD38-specific antibody of the invention may contain an antigen-binding region that contains an L-CDR3 region depicted in SEQ ID NO: 13, 14, or 15; the antigen-binding region may further include an L-CDR1 region depicted in SEQ ID NO: 13, 14, or 15; and the antigen-binding region also may contain an L-CDR2 region depicted in SEQ ID NO: 13, 14, or 15.

Antibodies (and functional fragments thereof) of the invention may contain an antigen-binding region that is specific for an epitope of CD38, which epitope contains one or more amino acid residues of amino acid residues 43 to 215 of CD38, as depicted by SEQ ID NO: 22. More specifically, an epitope to which the antigen-binding region binds may contain one or more amino acid residues found in one or more of the amino acid stretches taken from the list of amino acid stretches 44-66, 82-94, 142-154, 148-164, 158-170, and 192-206. For certain antibodies, the epitope maybe linear, whereas for others, it may be conformational (i.e., discontinuous). An antibody or functional fragment thereof having one or more of these properties may contain an antigen-binding region that contains an H-CDR3 region depicted in SEQ ID NO: 5, 6, 7, or 8; the antigen-binding region may further include an H-CDR2 region depicted in SEQ ID NO: 5, 6, 7, or 8; and the antigen-binding region also may contain an H-CDR1 region depicted in SEQ ID NO: 5, 6, 7, or 8. Such a CD38-specific antibody of the invention may contain an antigen-binding region that contains an L-CDR3 region depicted in SEQ ID NO: 13, 14, 15, or 16; the antigen-binding region may further include an L-CDR1 region depicted in SEQ ID NO: 13, 14, 15, or 16; and the antigen-binding region also may contain an L-CDR2 region depicted in SEQ ID NO: 13, 14, 15, or 16.

Peptide variants of the sequences disclosed herein are also embraced by the present invention. Accordingly, the invention includes anti-CD38 antibodies having a heavy chain amino acid sequence with: at least 60 percent sequence identity in the CDR regions with the CDR regions depicted in SEQ ID NO: 5, 6, 7, or 8; and/or at least 80 percent sequence homology in the CDR regions with the CDR regions depicted in SEQ ID NO: 5, 6, 7, or 8. Further included are anti-CD38 antibodies having a light chain amino acid sequence with: at least 60 percent sequence identity in the CDR regions with the CDR regions depicted in SEQ ID NO: 13, 14, 15 or 16; and/or at least 80 percent sequence homology in the CDR regions with the CDR regions depicted in SEQ ID NO: 13, 14, 15 or 16.

An antibody of the invention may be an IgG (e.g., $IgG_1$), while an antibody fragment may be a Fab or scFv, for example. An inventive antibody fragment, accordingly, may be, or may contain, an antigen-binding region that behaves in one or more ways as described herein.

The invention also is related to isolated nucleic acid sequences, each of which can encode an antigen-binding region of a human antibody or functional fragment thereof that is specific for an epitope of CD38. Such a nucleic acid sequence may encode a variable heavy chain of an antibody and include a sequence selected from the group consisting of SEQ ID NOS: 1, 2, 3, or 4, or a nucleic acid sequence that hybridizes under high stringency conditions to the complementary strand of SEQ ID NO: 1, 2, 3, or 4. The nucleic acid might encode a variable light chain of an isolated antibody or functional fragment thereof, and may contain a sequence selected from the group consisting of SEQ ID NOS: 9, 10, 11, or 12, or a nucleic acid sequence that hybridizes under high stringency conditions to the complementary strand of SEQ ID NO: 9, 10, 11, or 12.

Nucleic acids of the invention are suitable for recombinant production. Thus, the invention also relates to vectors and host cells containing a nucleic acid sequence of the invention.

Compositions of the invention may be used for therapeutic or prophylactic applications. The invention, therefore, includes a pharmaceutical composition containing an inventive antibody (or functional antibody fragment) and a pharmaceutically acceptable carrier or excipient therefor. In a related aspect, the invention provides a method for treating a disorder or condition associated with the undesired presence of CD38 or CD38 expressing cells. Such method contains the steps of administering to a subject in need thereof an effective amount of the pharmaceutical composition that contains an inventive antibody as described or contemplated herein.

The invention also relates to isolated epitopes of CD38, either in linear or conformational form, and their use for the isolation of an antibody or functional fragment thereof, which antibody of antibody fragment comprises an antigen-binding region that is specific for said epitope. In this regard, a linear epitope may contain amino acid residues 192-206, while a conformational epitope may contain one or more amino acid residues selected from the group consisting of amino acids 44-66, 82-94, 142-154, 148-164, 158-170 and 202-224 of CD38. An epitope of CD38 can be used, for example, for the isolation of antibodies or functional fragments thereof (each of which antibodies or antibody fragments comprises an antigen-binding region that is specific for such epitope), comprising the steps of contacting said epitope of CD38 with an antibody library and isolating the antibody(ies) or functional fragment(s) thereof.

In another embodiment, the invention provides an isolated epitope of CD38, which consists essentially of an amino acid sequence selected from the group consisting of amino acids 44-66, 82-94, 142-154, 148-164, 158-170, 192-206 and 202-224 of CD38. As used herein, such an epitope "consists essentially of" one of the immediately preceding amino acid sequences plus additional features, provided that the additional features do not materially affect the basic and novel characteristics of the epitope.

In yet another embodiment, the invention provides an isolated epitope of CD38 that consists of an amino acid sequence selected from the group consisting of amino acids 44-66, 82-94, 142-154, 148-164, 158-170, 192-206 and 202-224 of CD38.

The invention also provides a kit containing (i) an isolated epitope of CD38 comprising one or more amino acid stretches taken from the list of 44-66, 82-94, 142-154, 148-164, 158-170, 192-206 and 202-224; (ii) an antibody library; and (iii) instructions for using the antibody library to isolate one or more members of such library that binds specifically to such epitope.

BRIEF DESCRIPTION ON THE FIGURES

FIG. 1a provides nucleic acid sequences of various novel antibody variable heavy regions.

FIG. 1b provides amino acid sequences of various novel antibody variable heavy regions. CDR regions HCDR1, HCDR2 and HCDR3 are designated from N- to C-terminus in boldface.

FIG. 2a provides nucleic acid sequences of various novel antibody variable light regions.

FIG. 2b provides amino acid sequences of various novel antibody variable light regions. CDR regions LCDR1, LCDR2 and LCDR3 are designated from N- to C-terminus in boldface.

FIG. 3 provides amino acid sequences of variable heavy regions of various consensus-based HuCAL antibody master gene sequences. CDR regions HCDR1, HCDR2 and HCDR3 are designated from N- to C-terminus in boldface.

FIG. 4 provides amino acid sequences of variable light regions of various consensus-based HuCAL antibody master gene sequences. CDR regions LCDR1, LCDR2 and LCDR3 are designated from N- to C-terminus in boldface.

FIG. 5 provides the amino acid sequence of CD38 (SWISS-PROT primary accession number P28907).

FIG. 6 provides the nucleotide sequences of the heavy and light chains of chimeric OKT10.

FIG. 7 provides a schematic overview of epitopes of representative antibodies of the present invention.

FIG. 8 provides the DNA sequence of pMORPH®_h_IgG1_1 (bp 601-2100) (SEQ ID NO: 32): The vector is based on the pcDNA3.1+ vectors (Invitrogen). The amino acid sequence of the VH-stuffer sequence is indicated in bold, whereas the final reading frames of the VH-leader sequence and the constant region gene are printed in non-bold. Restriction sites are indicated above the sequence. The priming sites of the sequencing primers are underlined.

FIG. 9 provides the DNA sequence of Ig kappa light chain expression vector pMORPH®_h_Igκ_1 (bp 601-1400) (SEQ ID NO: 33): The vector is based on the pcDNA3.1+ vectors (Invitrogen). The amino acid sequences of the Vκ-stuffer sequence is indicated in bold, whereas the final reading frames of the Vκ-leader sequence and of the constant region gene are printed in non-bold. Restriction sites are indicated above the sequence. The priming sites of the sequencing primers are underlined.

FIG. 10 provides the DNA sequence of HuCAL Ig lambda light chain vector pMORPH®_h_Igλ_1 (bp 601-1400) (SEQ ID NO: 34): The amino acid sequence of the Vλ stuffer sequence is indicated in bold, whereas the final reading frames of the Vλ leader sequence and of the constant region gene are printed in non-bold. Restriction sites are indicated above the sequence. The priming sites of the sequencing primers are underlined.

FIG. 11 provides the results of the proliferation assay: PBMCs from 6 different healthy donors (as indicated by individual dots) were cultured for 3 days in the presence of HuCAL® antibodies Mab#1 (=MOR03077), Mab#2 (=MOR03079), and Mab#3 (=MOR03080), the reference antibody chOKT10, the agonistic (ag.) control IB4, an irrelevant HuCAL® negative control IgG1 (NC) and a murine IgG2a (Iso) as matched isotype control for IB4. A standard labeling with BrdU was used to measure proliferation activity and its incorporation (as RLU=relative light units) analyzed via a chemiluminescence-based ELISA.

FIG. 12 provides the results of the IL-6 Release Assay: PBMCs from 4-8 different healthy donors (as indicated by individual dots) were cultured for 24 hrs in the presence of HuCAL® antibodies Mab#1 (=MOR03077), Mab#2 (=MOR03079), and Mab#3 (=MOR03080), the reference antibody chOKT10, the agonistic (ag.) control IB4, an irrelevant HuCAL® negative control (NC) and medium only (Medium). IL-6 content in relative light units (RLU) was analyzed from culture supernatants via a chemiluminescence based ELISA.

FIG. 13 provides data about the cytotoxicity towards CD34+/CD38+ progenitor cells: PBMCs from healthy donors harboring autologous CD34+/CD38+ progenitor cells were incubated with HuCAL® Mab#1 (=MOR03077), Mab#2 (MOR03079), and Mab#3 (=MOR03080), the positive control (PC chOKT10) and an irrelevant HuCAL® negative control for 4 hours, respectively. Afterwards, the cell suspension was mixed with conditioned methyl-cellulose medium and incubated for 2 weeks. Colony forming units (CFU) derived from erythroid burst forming units (BFU-E; panel B) and granulocyte/erythroid/macrophage/megakaryocyte stem cells (CFU-GEMM; panels B) and granulocyte/macrophage stem cells (CFU-GM; panel C) were counted and normalized against the medium control ("none"=medium). Panel A represents the total number of CFU (Total CFUc) for all progenitors. Mean values from at least 10 different PBMC donors are given. Error bars represent standard error of the mean.

FIG. 14 provides data about ADCC with different cell-lines:
a: Single measurements (except for RPMI8226: average from 4 indiv. Assays); E:T-ratio: 30:1
b: Namba et al., 1989
c. 5 µg/ml used for antibody conc. (except for Raji with 0.1 µg/ml)
d: addition of retinoic assay for stimulation of CD38-expression specific killing [%]=[(exp. killing−medium killing)/(1−medium killing)]*100
PC: Positive control (=chOKT10)
MM: Multiple myeloma
CLL: Chronic B-cell leukemia
ALL: Acute lymphoblastic leukemia
AML: Acute myeloid leukemia
DSMZ: Deutsche Sammlung für Mikroorganismen and Zellkulturen GmbH
ATCC: American type culture collection
ECACC: European collection of cell cultures
MFI: Mean fluorescence intensities.

FIG. 15 provides data about ADCC with MM-samples:
$^a$: 2-4 individual analyses

FIG. 16 provides the experimental results of mean tumor volumes after treatment of human myeloma xenograft with MOR03080: group 1: vehicle; group 2: MOR03080 as hIgG1 1 mg/kg 32-68 days every second day; group 3: MOR03080 as hIgG1 5 mg/kg 32-68 days every second day; group 4: MOR03080 as chIgG2a 5 mg/kg 32-68 days every second day; group 5: MOR03080 as hIgG1 1 mg/kg, 14-36 days every second day; group 6: untreated

DETAILED DESCRIPTION OF THE INVENTION

The present invention is based on the discovery of novel antibodies that are specific to or have a high affinity for CD38 and can deliver a therapeutic benefit to a subject. The antibodies of the invention, which may be human or humanized, can be used in many contexts, which are more fully described herein.

A "human" antibody or functional human antibody fragment is hereby defined as one that is not chimeric (e.g., not "humanized") and not from (either in whole or in part) a non-human species. A human antibody or functional antibody fragment can be derived from a human or can be a synthetic human antibody. A "synthetic human antibody" is defined herein as an antibody having a sequence derived, in whole or in part, in silico from synthetic sequences that are based on the analysis of known human antibody sequences. In silico design of a human antibody sequence or fragment thereof can be achieved, for example, by analyzing a database of human antibody or antibody fragment sequences and devising a polypeptide sequence utilizing the data obtained therefrom. Another example of a human antibody or functional antibody fragment, is one that is encoded by a nucleic acid isolated from a library of antibody sequences of human origin (i.e., such library being based on antibodies taken from a human natural source).

A "humanized antibody" or functional humanized antibody fragment is defined herein as one that is (i) derived from a non-human source (e.g., a transgenic mouse which bears a heterologous immune system), which antibody is based on a human germline sequence; or (ii) chimeric, wherein the variable domain is derived from a non-human origin and the constant domain is derived from a human origin or (iii) CDR-grafted, wherein the CDRs of the variable domain are from a non-human origin, while one or more frameworks of the variable domain are of human origin and the constant domain (if any) is of human origin.

As used herein, an antibody "binds specifically to," is "specific to/for" or "specifically recognizes" an antigen (here, CD38) if such antibody is able to discriminate between such antigen and one or more reference antigen(s), since binding specificity is not an absolute, but a relative property. In its most general form (and when no defined reference is mentioned), "specific binding" is referring to the ability of the antibody to discriminate between the antigen of interest and an unrelated antigen, as determined, for example, in accordance with one of the following methods. Such methods comprise, but are not limited to Western blots, ELISA-, RIA-, ECL-, IRMA-tests and peptide scans. For example, a standard ELISA assay can be carried out. The scoring may be carried out by standard color development (e.g. secondary antibody with horseradish peroxide and tetramethyl benzidine with hydrogenperoxide). The reaction in certain wells is scored by the optical density, for example, at 450 nm. Typical background (=negative reaction) may be 0.1 OD; typical positive reaction may be 1 OD. This means the difference positive/negative can be more than 10-fold. Typically, determination of binding specificity is performed by using not a single reference antigen, but a set of about three to five unrelated antigens, such as milk powder, BSA, transferrin or the like.

However, "specific binding" also may refer to the ability of an antibody to discriminate between the target antigen and one or more closely related antigen(s), which are used as reference points, e.g. between CD38 and CD157. Additionally, "specific binding" may relate to the ability of an antibody to discriminate between different parts of its target antigen, e.g. different domains or regions of CD38, such as epitopes in the N-terminal or in the C-terminal region of CD38, or between one or more key amino acid residues or stretches of amino acid residues of CD38.

Also, as used herein, an "immunoglobulin" (Ig) hereby is defined as a protein belonging to the class IgG, IgM, IgE, IgA, or IgD (or any subclass thereof), and includes all conventionally known antibodies and functional fragments thereof. A "functional fragment" of an antibody/immunoglobulin hereby is defined as a fragment of an antibody/immunoglobulin (e.g., a variable region of an IgG) that retains the antigen-binding region. An "antigen-binding region" of an antibody typically is found in one or more hypervariable region(s) of an antibody, i.e., the CDR-1, -2, and/or -3 regions; however, the variable "framework" regions can also play an important role in antigen binding, such as by providing a scaffold for the CDRs. Preferably, the "antigen-binding region" comprises at least amino acid residues 4 to 103 of the variable light (VL) chain and 5 to 109 of the variable heavy (VH) chain, more preferably amino acid residues 3 to 107 of VL and 4 to 111 of VH, and particularly preferred are the complete VL and VH chains (amino acid positions 1 to 109 of VL and 1 to 113 of VH; numbering according to WO 97/08320). A preferred class of immunoglobulins for use in the present invention is IgG. "Functional fragments" of the invention include the domain of a F(ab')$_2$ fragment, a Fab fragment and scFv. The F(ab')$_2$ or Fab may be engineered to minimize or completely remove the intermolecular disulphide interactions that occur between the $C_{H1}$ and $C_L$ domains.

An antibody of the invention may be derived from a recombinant antibody library that is based on amino acid sequences that have been designed in silico and encoded by nucleic acids that are synthetically created. In silico design of an antibody sequence is achieved, for example, by analyzing a database of human sequences and devising a polypeptide sequence utilizing the data obtained therefrom. Methods for designing and obtaining in silico-created sequences are described, for example, in Knappik et al., J. Mol. Biol. (2000) 296:57; Krebs et al., J. Immunol. Methods. (2001) 254:67; and U.S. Pat. No. 6,300,064 issued to Knappik et al., which hereby are incorporated by reference in their entirety.

Antibodies of the Invention

Throughout this document, reference is made to the following representative antibodies of the invention: "antibody nos." or "LACS" or "MOR" 3077, 3079, 3080 and 3100. LAC 3077 represents an antibody having a variable heavy region corresponding to SEQ ID NO: 1 (DNA)/SEQ ID NO: 5 (protein) and a variable light region corresponding to SEQ ID NO: 9 (DNA)/SEQ ID NO: 13 (protein). LAC 3079 represents an antibody having a variable heavy region corresponding to SEQ ID) NO: 2 (DNA)/SEQ ID) NO: 6 (protein) and a variable light region corresponding to SEQ ID) NO: 10 (DNA)/SEQ ID NO: 14 (protein). LAC 3080 represents an antibody having a variable heavy region corresponding to SEQ ID NO: 3 (DNA)/SEQ ID NO: 7 (protein) and a variable light region corresponding to SEQ ID NO: 11 (DNA)/SEQ ID NO: 15 (protein). LAC 3100 represents an antibody having a variable heavy region corresponding to SEQ ID NO: 4 (DNA)/SBQ ID NO: 8 (protein) and a variable light region corresponding to SEQ ID NO: 12 (DNA)/SEQ ID NO: 16 (protein).

In one aspect, the invention provides antibodies having an antigen-binding region that can bind specifically to or has a high affinity for one or more regions of CD38, whose amino acid sequence is depicted by SEQ ID NO: 22. An antibody is said to have a "high affinity" for an antigen if the affinity measurement is at least 100 nM (monovalent affinity of Fab fragment). An inventive antibody or antigen-binding region preferably can bind to CD38 with an affinity of about less than 100 nM, more preferably less than about 60 nM, and still more preferably less than about 30 nM. Further preferred are antibodies that bind to CD38 with an affinity of less than about 10 nM, and more preferably less than 3 about nM. For instance, the affinity of an antibody of the invention against CD38 may be about 10.0 nM or 2.4 nM (monovalent affinity of Fab fragment).

Table 1 provides a summary of affinities of representative antibodies of the invention, as determined by surface plasmon resonance (Biacore) and FACS Scatchard analysis:

TABLE 1

Antibody Affinities

| Antibody (Fab or IgG1) | BIACORE (Fab) $K_D$ [nM][a] | FACS Scatchard (IgG1)[b] $K_D$ [nM][a] |
|---|---|---|
| MOR03077 | 56.0 | 0.89 |
| MOR03079 | 2.4 | 0.60 |
| MOR03080 | 27.5 | 0.47 |
| MOR03100 | 10.0 | 6.31 |
| Chimeric OKT10 | not determined | 8.28 |

[a]mean from at least 2 different affinity determinations
[b]RPMI8226 MM cell-line used for FACS-Scatchards With reference to Table 1, the affinity of LACs 3077, 3079, 3080 and 3100 was measured by surface plasmon resonance (Biacore) on immobilized recombinant CD38 and by a flow cytometry procedure utilizing the CD38-expressing human RPM18226 cell line. The Biacore studies were performed on directly immobilized antigen (CD38-Fc fusion protein). The Fab format of LACs 3077, 3079, 3080 and 3100 exhibit an monovalent affinity range between about 2.4 and 56 nM on immobilized CD38-Fc fusion protein with LAC 3079 showing the highest affinity, followed by Fabs 3100, 3080 and 3077.

The IgG1 format was used for the cell-based affinity determination (FACS Scatchard). The right column of Table 1 denotes the binding strength of the LACS in this format. LAC 3080 showed the strongest binding, which is slightly stronger than LACS 3079 and 3077.

Another preferred feature of preferred antibodies of the invention is their specificity for an area within the N-terminal region of CD38. For example, LACs 3077, 3079, 3080, and 3100 of the invention can bind specifically to the N-terminal region of CD38.

The type of epitope to which an antibody of the invention binds may be linear (i.e. one consecutive stretch of amino acids) or conformational (i.e. multiple stretches of amino acids). In order to determine whether the epitope of a particular antibody is linear or conformational, the skilled worker can analyze the binding of antibodies to overlapping peptides (e.g., 13-mer peptides with an overlap of 11 amino acids) covering different domains of CD38. Using this analysis, the inventors have discovered that LACS 3077, 3080, and 3100 recognize discontinuous epitopes in the N-terminal region of CD38, whereas the epitope of LAC 3079 can be described as linear (see FIG. 7). Combined with the knowledge provided herein, the skilled worker in the art will know how to use one or more isolated epitopes of CD38 for generating antibodies having an antigen-binding region that is specific for said epitopes (e.g. using synthetic peptides of epitopes of CD38 or cells expressing epitopes of CD38).

An antibody of the invention preferably is species cross-reactive with humans and at least one other species, which may be a rodent species or a non-human primate. The non-human primate can be rhesus, baboon and/or cynomolgus. The rodent species can be mouse, rat and/or hamster. An antibody that is cross reactive with at least one rodent species, for example, can provide greater flexibility and benefits over known anti-CD38 antibodies, for purposes of conducting in vivo studies in multiple species with the same antibody.

Preferably, an antibody of the invention not only is able to bind to CD38, but also is able to mediate killing of a cell expressing CD38. More specifically, an antibody of the invention can mediate its therapeutic effect by depleting CD38-positive (e.g., malignant) cells via antibody-effector functions. These functions include antibody-dependent cellular cytotoxicity (ADCC) and complement-dependent cytotoxicity (CDC).

Table 2 provides a summary of the determination of EC50 values of representative antibodies of the invention in both ADCC and CDC:

TABLE 2

EC50 Values of Antibodies

| Antibody (IgG1) | ADCC EC50 [nM] | | CJ)C EC50 [nM] |
|---|---|---|---|
| | LP-1 | RPM18226 | CHO-transfectants |
| MOR03077 | 0.60[a] | 0.08[a] | 0.8[c]; 0.94[d] |
| MOR03079 | 0.09[a] | 0.04[a] | 0.41[c] |
| MOR03080 | 0.17[b] | 0.05[a] | 3.2[c]; 2.93[d] |
| MORO3100 | 1.00[b] | 0.28[a] | 10.9[c]; 13.61[e] |
| Chimeric OKT10 | 5.23[a] | 4.10[a] | 9.30[c] |

[a]mean from at least 2 EC50 determinations
[b]single determination
[c]mean from 2 EC50 determinations
[d]mean from 3 EC50 determinations
[e]mean from 4 EC50 determinations CD38-expression, however, is not only found on immune cells within the myeloid (e.g. monocytes, granulocytes) and lymphoid lineage (e.g. activated B and T-cells; plasma cells), but also on the respective precursor cells. Since it is important that those cells are not affected by antibody-mediated killing of malignant cells, the antibodies of the present invention are preferably not cytotoxic to precursor cells.

In addition to its catalytic activities as a cyclic ADP-ribose cyclase and hydrolase, CD38 displays the ability to transduce signals of biological relevance (Hoshino et al., 1997; Ausiello et al., 2000). Those functions can be induced in vivo by, e.g. receptor-ligand interactions or by cross-linking with agonistic anti-CD38 antibodies, leading, e.g. to calcium mobilization, lymphocyte proliferation and release of cytokines. Preferably, the antibodies of the present invention are non-agonistic antibodies.

Peptide Variants

Antibodies of the invention are not limited to the specific peptide sequences provided herein. Rather, the invention also embodies variants of these polypeptides.

With reference to the instant disclosure and conventionally available technologies and references, the skilled worker will be able to prepare, test and utilize functional variants of the antibodies disclosed herein, while appreciating that variants having the ability to mediate killing of a CD38+ target cell fall within the scope of the present invention. As used in this context, "ability to mediate killing of a CD38+ target cell" means a functional characteristic ascribed to an anti-CD38 antibody of the invention. Ability to mediate killing of a CD38+ target cell, thus, includes the ability to mediate killing of a CD38+ target cell, e.g. by ADCC and/or CDC, or by toxin constructs conjugated to an antibody of the invention.

A variant can include, for example, an antibody that has at least one altered complementarity determining region (CDR) (hyper-variable) and/or framework (FR) (variable) domain/position, vis-à-vis a peptide sequence disclosed herein. To better illustrate this concept, a brief description of antibody structure follows.

An antibody is composed of two peptide chains, each containing one (light chain) or three (heavy chain) constant domains and a variable region (VL, VH), the latter of which is in each case made up of four FR regions and three interspaced CDRs. The antigen-binding site is formed by one or more CDRs, yet the FR regions provide the structural framework for the CDRs and, hence, play an important role in antigen binding. By altering one or more amino acid residues in a CDR or FR region, the skilled worker routinely can generate mutated or diversified antibody sequences, which can be screened against the antigen, for new or improved properties, for example.

Tables 3a (VH) and 3b (VL) delineate the CDR and FR regions for certain antibodies of the invention and compare amino acids at a given position to each other and to corresponding consensus or "master gene" sequences (as described in U.S. Pat. No. 6,300,064):

TABLE 3a

VH Sequences

VH sequences CD38 binders

Framework 1 / CDR 1

Position: 1 2 3 4 5 6 7 8 9 0 1 2 3 4 5 6 7 8 9 0 1 2 3 4 5 6 7 8 9 0 1 a b 2 3 4 5

MfeI ... BspEI

| SEQ ID NO | | Framework 1 | CDR 1 |
|---|---|---|---|
| SEQ ID NO VH1B  | Q V Q L | V Q S G A E V K K P G A S V K V S C K A | S G Y T F T S _ _ Y Y M H |
| SEQ ID NO 3077  | Q V Q L | V Q S G A E V K K P G A S V K V S C K A | S G Y T F T S _ _ Y S I N |
| SEQ ID NO VH3   | E V Q L | V E S G G G L V Q P G G S L R L S C A A | S G F T F S S _ _ Y A M S |
| SEQ ID NO 3079  | Q V Q L | V E S G G G L V Q P G G S L R L S C A A | S G F T F S N _ _ Y G M H |
| SEQ ID NO 3080  | Q V Q L | V E S G G G L V Q P G G S L R L S C A A | S G F T F S S _ _ Y G M H |
| SEQ ID NO 3100  | Q V Q L | V E S G G G L V Q P G G S L R L S C A A | S G F T F S S _ _ N G M S |

Framework 2 / CDR 2

Position: 6 7 8 9 0 1 2 3 4 5 6 7 8 9 0 1 2 a b c 3 4 5 6 7 8 9 0 1 2 3 4 5

BstXI ... XhoI

| SEQ ID NO | Framework 2 | CDR 2 |
|---|---|---|
| SEQ ID NO VH1B  | W V R Q A P G Q G L E W M G | W I N P _ _ N S G G T N Y A Q K F Q G |
| SEQ ID NO 3077  | W V R Q A P G Q G L E W M G | Y I D P _ _ N R G N T N Y A Q K F Q G |
| SEQ ID NO VH3   | W V R Q A P G K G L E W V S | A I S G _ _ S G G S T Y Y A D S V K G |
| SEQ ID NO 3079  | W V R Q A P G K G L E W V S | N I R S _ _ D G S W T Y Y A D S V K G |
| SEQ ID NO 3080  | W V R Q A P G K G L E W V S | N I Y S _ _ D G S N T F Y A D S V K G |
| SEQ ID NO 3100  | W V R Q A P G K G L E W V S | N I S Y _ _ L S S S T Y Y A D S V K G |

VH — Framework 3

Position: 6 7 8 9 0 1 2 3 4 5 6 7 8 9 0 1 2 a b c 3 4 5 6 7 8 9 0 1 2 3 4

BstEII ... EagI ... BssHII

| SEQ ID NO | Framework 3 |
|---|---|
| SEQ ID NO VH1B  | R V T M T R D T S I S T A Y M E L S S L R S E D T A V Y Y C A R |
| SEQ ID NO 3077  | R V T M T R D T S I S T A Y M E L S S L R S E D T A V Y Y C A R |
| SEQ ID NO VH3   | R F T I S R D N S K N T L Y L Q M N S L R A E D T A V Y Y C A R |
| SEQ ID NO 3079  | R F T I S R D N S K N T L Y L Q M N S L R A E D T A V Y Y C A R |
| SEQ ID NO 3080  | R F T I S R D N S K N T L Y L Q M N S L R A E D T A V Y Y C A R |
| SEQ ID NO 3100  | R F T I S R D N S K N T L Y L Q M N S L R A E D T A V Y Y C A R |

CDR 3 / Framework 4

Position: 5 6 7 8 9 0 a b c d e f g h i j 1 2 3 4 5 6 7 8 9 0 1 2 3

StyI ... BlpI

| SEQ ID NO | CDR 3 | Framework 4 |
|---|---|---|
| SEQ ID NO VH1B  | W G G D G F Y A _ _ _ _ _ _ _ M D Y | W G Q G T L V T V S S |
| SEQ ID NO 3077  | E Y I Y F I H G M _ _ _ _ _ _ L D F | W G Q G T L V T V S S |
| SEQ ID NO VH3   | W G G D G F Y A _ _ _ _ _ _ _ M D Y | W G Q G T L V T V S S |
| SEQ ID NO 3079  | R Y W S K S H A S V _ _ _ _ _ T D Y | W G Q G T L V T V S S |
| SEQ ID NO 3080  | N M Y R W P F H Y F _ _ _ _ _ F D Y | W G Q G T L V T V S S |
| SEQ ID NO 3100  | F Y G Y F N Y _ _ _ _ _ _ _ _ A D V | W G Q G T L V T V S S |

TABLE 3B

VL Sequences

VL sequences CD38 binders

Framework 1 / CDR 1

| SEQ ID | VL | Position: 1 2 3 4 5 6 7 8 9 0 1 2 3 4 5 6 7 8 9 0 1 2 3 4 5 6 7 8 9 0 a b c |
|---|---|---|
| | | EcoRV / SexAI / BssSI |
| SEQ ID NO 21 | VL13 | S Y E L T Q P P - S V S V A P G Q T A R I S C S G D A L G D - - - |
| SEQ ID NO 13 | 3080 | D I E L T Q P P - S V S V A P G Q T A R I S C S G D N I G N - - - |
| SEQ ID NO 15 | 3100 | D I E L T Q P P - S V S V A P G Q T A R I S C S G D N I G H - - - |
| SEQ ID NO 22 | VLx1 | D I Q M T Q S P S S L S A S V G D R V T I T C R A S Q G I S - - - |
| SEQ ID NO 14 | 3079 | D I Q M T Q S P S S L S A S V G D R V T I T C R A S Q D I S - - - |
| SEQ ID NO 22 | VLx2 | D I V M T Q S P L S L P V T P G E P A S I S C R S S Q S L L H S - |
| SEQ ID NO 14 | 3077 | D I V M T Q S P L S L P V T P G E P A S I S C R S S Q S L L F I - |

CDR 1 / Framework 2 / CDR 2

| SEQ ID | VL | Position: d e f 1 2 3 4 5 6 7 8 9 0 1 2 3 4 5 6 7 8 9 0 1 2 3 4 5 6 7 8 9 |
|---|---|---|
| | | KpnI / XmaI / BbeI / Bsu36I |
| SEQ ID NO 21 | VL13 | - - - K Y A S W Y Q Q K P G Q A P V L V I Y D D S D R P S G I P |
| SEQ ID NO 13 | 3080 | - - - K Y V S W Y Q Q K P G Q A P V V V I Y G D N N R P S G I P |
| SEQ ID NO 15 | 3100 | - - - Y Y A S W Y Q Q K P G Q A P V L V I Y R D N D R P S G I P |
| SEQ ID NO 22 | VLx1 | - - - S Y L A W Y Q Q K P G K A P K L L I Y A A S S L Q S G V P |
| SEQ ID NO 14 | 3079 | - - - A F L N W Y Q Q K P G K A P K L L I Y K V S N L Q S G V P |
| SEQ ID NO 22 | VLx2 | N G Y N Y L D W Y L Q K P G Q S P Q L L I Y L G S N R A S G V P |
| SEQ ID NO 14 | 3077 | D G N N Y L N W Y L Q K P G Q S P Q L L I Y L G S N R A S G V P |

Framework 3

| SEQ ID | VL | Position: 6 0 1 2 3 4 5 6 7 8 9 0 1 2 3 4 5 6 7 8 9 0 1 2 3 4 5 6 7 8 |
|---|---|---|
| | | BamHI / BbsI |
| SEQ ID NO 21 | VL13 | E R F S G S N S G N T A T L T I S G T Q A E D E A D Y Y C |
| SEQ ID NO 13 | 3080 | E R F S G S N S G N T A T L T I S G T Q A E D E A D Y Y C |
| SEQ ID NO 15 | 3100 | E R F S G S N S G N T A T L T I S G T Q A E D E A D Y Y C |
| SEQ ID NO 22 | VLx1 | S R F S G S G S G T D F T L T I S S L Q P E D F A T Y Y C |
| SEQ ID NO 14 | 3079 | S R F S G S G S G T D F T L T I S S L Q P E D F A T Y Y C |
| SEQ ID NO 22 | VLx2 | D R F S G S G S G T D F T L K I S R V E A E D V G V Y Y C |
| SEQ ID NO 14 | 3077 | D R F S G S G S G T D F T L K I S R V E A E D V G V Y Y C |

CDR 3 / Framework 4

| SEQ ID | VL | Position: 9 0 1 2 3 4 5 a b 6 7 8 9 0 1 2 3 4 5 6 7 8 9 |
|---|---|---|
| | | HpaI / MscI |
| SEQ ID NO 21 | VL13 | Q Q H Y T T P - - P V F G G G T K L T V L G |
| SEQ ID NO 13 | 3080 | S S Y D S S Y - - F V F G G G T K L T V L G Q |
| SEQ ID NO 15 | 3100 | Q S Y D Y L H D - F V F G G G T K L T V L G Q |
| SEQ ID NO 22 | VLx1 | Q Q H Y T T P - - P T F G Q G T K V E I K R |
| SEQ ID NO 14 | 3079 | Q Q A Y S G S - - I T F G Q G T K V E I K R T |
| SEQ ID NO 22 | VLx2 | Q Q H Y T T P - - P T F G Q G T K L E I K R |
| SEQ ID NO 14 | 3077 | Q Q Y S S K S - - A T F G Q G T K V E I K R T |

The skilled worker can use the data in Tables 3a and 3b to design peptide variants that are within the scope of the present invention. It is preferred that variants are constructed by changing amino acids within one or more CDR regions; a variant might also have one or more altered framework regions. With reference to a comparison of the novel antibodies to each other, candidate residues that can be changed include e.g. residues 4 or 37 of the variable light and e.g. residues 13 or 43 of the variable heavy chains of LACs 3080 and 3077, since these are positions of variance vis-à-vis each other. Alterations also may be made in the framework regions. For example, a peptide FR domain might be altered where there is a deviation in a residue compared to a germline sequence.

With reference to a comparison of the novel antibodies to the corresponding consensus or "master gene" sequence, candidate residues that can be changed include e.g. residues 27, 50 or 90 of the variable light chain of LAC 3080 compared to VU3 and e.g. residues 33, 52 and 97 of the variable heavy chain of LAC 3080 compared to VH3. Alternatively, the skilled worker could make the same analysis by comparing the amino acid sequences disclosed herein to known sequences of the same class of such antibodies, using, for example, the procedure described by Knappik et al, 2000 and U.S. Pat. No. 6,300,064 issued to Knappik et al.

Furthermore, variants may be obtained by using one LAC as starting point for optimization by diversifying one or more amino acid residues in the LAC, preferably amino acid residues in one or more CDRs, and by screening the resulting collection of antibody variants for variants with improved properties. Particularly preferred is diversification of one or more amino acid residues in CDR-3 of VL, CDR-3 of VH, CDR-1 of VL and/or CDR-2 of VH. Diversification can be done by synthesizing a collection of DNA molecules using trinucleotide mutagenesis (TRIM) technology (Virnekiis, B., Ge, L., Plückthun, A., Schneider, K. C., Wellnhofer, G., and Moroney S. E. (1994) Trinucleotide phosphoramidites: ideal reagents for the synthesis of mixed oligonucleotides for random mutagenesis. Nucl. Acids Res. 22, 5600.).

Conservative Amino Add Variants

Polypeptide variants may be made that conserve the overall molecular structure of an antibody peptide sequence described herein. Given the properties of the individual amino acids, some rational substitutions will be recognized by the skilled worker. Amino acid substitutions, i.e., "conservative substitutions," may be made, for instance, on the basis of similarity in polarity, charge, solubility, hydrophobicity, hydrophilicity, and/or the amphipathic nature of the residues involved.

For example, (a) nonpolar (hydrophobic) amino acids include alanine, leucine, isoleucine, valine, proline, phenylalanine, tryptophan, and methionine; (b) polar neutral amino acids include glycine, serine, threonine, cysteine, tyrosine, asparagine, and glutamine; (c) positively charged (basic) amino acids include arginine, lysine, and histidine; and (d) negatively charged (acidic) amino acids include aspartic acid and glutamic acid. Substitutions typically may be made within groups (a)-(d). In addition, glycine and proline may be substituted for one another based on their ability to disrupt α-helices. Similarly, certain amino acids, such as alanine, cysteine, leucine, methionine, glutamic acid, glutamine, histidine and lysine are more commonly found in α-helices, while valine, isoleucine, phenylalanine, tyrosine, tryptophan and threonine are more commonly found in β-pleated sheets. Glycine, serine, aspartic acid, asparagine, and proline are commonly found in turns. Some preferred substitutions may be made among the following groups: (i) S and T; (ii) P and G; and (iii) A, V, L and I. Given the known genetic code, and recombinant and synthetic DNA techniques, the skilled scientist readily can construct DNAs encoding the conservative amino acid variants. In one particular example, amino acid position 3 in SEQ ID NOS: 5, 6, 7, and/or 8 can be changed from a Q to an E.

As used herein, "sequence identity" between two polypeptide sequences indicates the percentage of amino acids that are identical between the sequences. "Sequence similarity" indicates the percentage of amino acids that either are identical or that represent conservative amino acid substitutions. Preferred polypeptide sequences of the invention have a sequence identity in the CDR regions of at least 60%, more preferably, at least 70% or 80%, still more preferably at least 90% and most preferably at least 95%. Preferred antibodies also have a sequence similarity in the CDR regions of at least 80%, more preferably 90% and most preferably 95%.

DNA Molecules of the Invention

The present invention also relates to the DNA molecules that encode an antibody of the invention. These sequences include, but are not limited to, those DNA molecules set forth in FIGS. 1a and 2a.

DNA molecules of the invention are not limited to the sequences disclosed herein, but also include variants thereof. DNA variants within the invention may be described by reference to their physical properties in hybridization. The skilled worker will recognize that DNA can be used to identify its complement and, since DNA is double stranded, its equivalent or homolog, using nucleic acid hybridization techniques. It also will be recognized that hybridization can occur with less than 100% complementarity. However, given appropriate choice of conditions, hybridization techniques can be used to differentiate among DNA sequences based on their structural relatedness to a particular probe. For guidance regarding such conditions see, Sambrook et al., 1989 (Sambrook, J., Fritsch, E. F. and Maniatis, T. (1989) Molecular Cloning: A laboratory manual, Cold Spring Harbor Laboratory Press, Cold Spring Harbor, USA) and Ausubel et al., 1995 (Ausubel, F. M., Brent, R., Kingston, R. E., Moore, D. D., Sedman, J. G., Smith, J. A., & Struhl, K. eds. (1995). Current Protocols in Molecular Biology. New York: John Wiley and Sons).

Structural similarity between two polynucleotide sequences can be expressed as a function of "stringency" of the conditions under which the two sequences will hybridize with one another. As used herein, the term "stringency" refers to the extent that the conditions disfavor hybridization. Stringent conditions strongly disfavor hybridization, and only the most structurally related molecules will hybridize to one another under such conditions. Conversely, non-stringent conditions favor hybridization of molecules displaying a lesser degree of structural relatedness. Hybridization stringency, therefore, directly correlates with the structural relationships of two nucleic acid sequences. The following relationships are useful in correlating hybridization and relatedness (where $T_m$ is the melting temperature of a nucleic acid duplex):

a. $T_m$ 69.3+0.41(G+C) %
b. The $T_m$ of a duplex DNA decreases by 1° C. with every increase of 1% in the number of mismatched base pairs.
c. $(T_m)_{\mu 2} - (T_m)_{\mu 1} = 18.5 \log_{10} \mu 2/\mu 1$
where $_\mu 1$ and $_\mu 2$ are the ionic strengths of two solutions.

Hybridization stringency is a function of many factors, including overall DNA concentration, ionic strength, temperature, probe size and the presence of agents which disrupt hydrogen bonding. Factors promoting hybridization include high DNA concentrations, high ionic strengths, low temperatures, longer probe size and the absence of agents that disrupt hydrogen bonding. Hybridization typically is performed in two phases: the "binding" phase and the "washing" phase.

First, in the binding phase, the probe is bound to the target under conditions favoring hybridization. Stringency is usually controlled at this stage by altering the temperature. For high stringency, the temperature is usually between 65° C. and 70° C., unless short (<20 nt) oligonucleotide probes are used. A representative hybridization solution comprises 6×SSC, 0.5% SDS, 5×Denhardt's solution and 100 µg of nonspecific carrier DNA. See Ausubel et al., section 2.9, supplement 27 (1994). Of course, many different, yet functionally equivalent, buffer conditions are known. Where the degree of relatedness is lower, a lower temperature may be chosen. Low stringency binding temperatures are between about 25° C. and 40° C. Medium stringency is between at least about 40° C. to less than about 65° C. High stringency is at least about 65° C.

Second, the excess probe is removed by washing. It is at this phase that more stringent conditions usually are applied. Hence, it is this "washing" stage that is most important in determining relatedness via hybridization. Washing solutions typically contain lower salt concentrations. One exemplary medium stringency solution contains 2×SSC and 0.1% SDS. A high stringency wash solution contains the equivalent (in ionic strength) of less than about 0.2×SSC, with a preferred stringent solution containing about O.1×SSC. The temperatures associated with various stringencies are the same as discussed above for "binding." The washing solution also typically is replaced a number of times during washing. For example, typical high stringency washing conditions comprise washing twice for 30 minutes at 55° C. and three times for 15 minutes at 60° C.

Accordingly, the present invention includes nucleic acid molecules that hybridize to the molecules of set forth in FIGS. 1a and 2a under high stringency binding and washing conditions, where such nucleic molecules encode an antibody or functional fragment thereof having properties as described herein. Preferred molecules (from an mRNA perspective) are those that have at least 75% or 80% (preferably at least 85%, more preferably at least 90% and most preferably at least 95%) homology or sequence identity with one of the DNA molecules described herein. In one particular example of a variant of the invention, nucleic acid position 7 in SEQ ID NOS: 1, 2, 3 and/or 4 can be substituted from a C to a G, thereby changing the codon from CAA to GAA.

Functionally Equivalent Variants

Yet another class of DNA variants within the scope of the invention may be described with reference to the product they encode (see the peptides listed in FIGS. 1b and 2b). These functionally equivalent genes are characterized by the fact that they encode the same peptide sequences found in FIGS. 1b and 2b due to the degeneracy of the genetic code. SEQ ID NOS: 1 and 31 are an example of functionally equivalent variants, as their nucleic acid sequences are different, yet they encode the same polypeptide, i.e. SEQ ID NO: 5.

It is recognized that variants of DNA molecules provided herein can be constructed in several different ways. For example, they may be constructed as completely synthetic DNAs. Methods of efficiently synthesizing oligonucleotides in the range of 20 to about 150 nucleotides are widely available. See Ausubel et al., section 2.11, Supplement 21 (1993). Overlapping oligonucleotides may be synthesized and assembled in a fashion first reported by Khorana et al., J. Mol. Biol. 72:209-217 (1971); see also Ausubel et al., supra, Section 8.2. Synthetic DNAs preferably are designed with convenient restriction sites engineered at the 5' and 3' ends of the gene to facilitate cloning into an appropriate vector.

As indicated, a method of generating variants is to start with one of the DNAs disclosed herein and then to conduct site-directed mutagenesis. See Ausubel et al., supra, chapter 8, Supplement 37 (1997). In a typical method, a target DNA is cloned into a single-stranded DNA bacteriophage vehicle. Single-stranded DNA is isolated and hybridized with an oligonucleotide containing the desired nucleotide alteration(s). The complementary strand is synthesized and the double stranded phage is introduced into a host. Some of the resulting progeny will contain the desired mutant, which can be confirmed using DNA sequencing. In addition, various methods are available that increase the probability that the progeny phage will be the desired mutant. These methods are well known to those in the field and kits are commercially available for generating such mutants.

Recombinant DNA Constructs and Expression

The present invention further provides recombinant DNA constructs comprising one or more of the nucleotide sequences of the present invention. The recombinant constructs of the present invention are used in connection with a vector, such as a plasmid or viral vector, into which a DNA molecule encoding an antibody of the invention is inserted.

The encoded gene may be produced by techniques described in Sambrook et al., 1989, and Ausubel et al., 1989. Alternatively, the DNA sequences may be chemically synthesized using, for example, synthesizers. See, for example, the techniques described in OLIGONUCLEOTIDE SYNTHESIS (1984, Gait, ed., IRL Press, Oxford), which is incorporated by reference herein in its entirety. Recombinant constructs of the invention are comprised with expression vectors that are capable of expressing the RNA and/or protein products of the encoded DNA(s). The vector may further comprise regulatory sequences, including a promoter operably linked to the open reading frame (ORF). The vector may further comprise a selectable marker sequence. Specific initiation and bacterial secretory signals also may be required for efficient translation of inserted target gene coding sequences.

The present invention further provides host cells containing at least one of the DNAs of the present invention. The host cell can be virtually any cell for which expression vectors are available. It may be, for example, a higher eukaryotic host cell, such as a mammalian cell, a lower eukaryotic host cell, such as a yeast cell, but preferably is a prokaryotic cell, such as a bacterial cell. Introduction of the recombinant construct into the host cell can be effected by calcium phosphate transfection, DEAE, dextran mediated transfection, electroporation or phage infection.

Bacterial Expression

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and, if desirable, to provide amplification within the host. Suitable prokaryotic hosts for transformation include *E. coli, Bacillus subtilis, Salmonella typhimurium* and various species within the genera *Pseudomonas, Streptomyces,* and *Staphylococcus.*

Bacterial vectors may be, for example, bacteriophage-, plasmid- or phagemid-based. These vectors can contain a selectable marker and bacterial origin of replication derived from commercially available plasmids typically containing elements of the well known cloning vector pBR322 (ATCC 37017). Following transformation of a suitable host strain and growth of the host strain to an appropriate cell density, the selected promoter is de-repressed/induced by appropriate means (e.g., temperature shift or chemical induction) and cells are cultured for an additional period. Cells are typically harvested by centrifugation, disrupted by physical or chemical means, and the resulting crude extract retained for further purification.

In bacterial systems, a number of expression vectors may be advantageously selected depending upon the use intended for the protein being expressed. For example, when a large quantity of such a protein is to be produced, for the generation of antibodies or to screen peptide libraries, for example, vectors which direct the expression of high levels of fusion protein products that are readily purified may be desirable.

Therapeutic Methods

Therapeutic methods involve administering to a subject in need of treatment a therapeutically effective amount of an antibody contemplated by the invention. A "therapeutically effective" amount hereby is defined as the amount of an antibody that is of sufficient quantity to deplete CD38-positive cells in a treated area of a subject—either as a single dose or according to a multiple dose regimen, alone or in combination with other agents, which leads to the alleviation of an adverse condition, yet which amount is toxicologically tolerable. The subject may be a human or non-human animal (e.g., rabbit, rat, mouse, monkey or other lower-order primate).

An antibody of the invention might be co-administered with known medicaments, and in some instances the antibody might itself be modified. For example, an antibody could be conjugated to an immunotoxin or radioisotope to potentially further increase efficacy.

The inventive antibodies can be used as a therapeutic or a diagnostic tool in a variety of situations where CD38 is undesirably expressed or found. Disorders and conditions particularly suitable for treatment with an antibody of the inventions are multiple myeloma (MM) and other haematological diseases, such as chronic lymphocytic leukemia (CLL), chronic myelogenous leukemia (CML), acute myelogenous leukemia (AML), and acute lymphocytic leukemia (ALL). An antibody of the invention also might be used to treat inflammatory disease such as rheumatoid arthritis (RA) or systemic lupus erythematosus (SLE).

To treat any of the foregoing disorders, pharmaceutical compositions for use in accordance with the present invention may be formulated in a conventional manner using one or more physiologically acceptable carriers or excipients. An antibody of the invention can be administered by any suitable means, which can vary, depending on the type of disorder being treated. Possible administration routes include parenteral (e.g., intramuscular, intravenous, intraarterial, intraperitoneal, or subcutaneous), intrapulmonary and intranasal, and, if desired for local immunosuppressive treatment, intralesional administration. In addition, an antibody of the invention might be administered by pulse infusion, with, e.g., declining doses of the antibody. Preferably, the dosing is given by injections, most preferably intravenous or subcutaneous injections, depending in part on whether the administration is brief or chronic. The amount to be administered will depend on a variety of factors such as the clinical symptoms, weight of the individual, whether other drugs are administered. The skilled artisan will recognize that the route of administration will vary depending on the disorder or condition to be treated.

Determining a therapeutically effective amount of the novel polypeptide, according to this invention, largely will depend on particular patient characteristics, route of administration, and the nature of the disorder being treated. General guidance can be found, for example, in the publications of the International Conference on Harmonisation and in REMINGTON'S PHARMACEUTICAL SCIENCES, chapters 27 and 28, pp. 484-528 (18th ed., Alfonso R. Gennaro, Ed., Easton, Pa.: Mack Pub. Co., 1990). More specifically, determining a therapeutically effective amount will depend on such factors as toxicity and efficacy of the medicament. Toxicity may be determined using methods well known in the art and found in the foregoing references. Efficacy may be determined utilizing the same guidance in conjunction with the methods described below in the Examples.

Diagnostic Methods

CD38 is highly expressed on hematological cells in certain malignancies; thus, an anti-CD38 antibody of the invention may be employed in order to image or visualize a site of possible accumulation of malignant cells in a patient. In this regard, an antibody can be detectably labeled, through the use of radioisotopes, affinity labels (such as biotin, avidin, etc.) fluorescent labels, paramagnetic atoms, etc. Procedures for accomplishing such labeling are well known to the art. Clinical application of antibodies in diagnostic imaging are reviewed by Grossman, H. B., Urol. Clin. North Amer. 13:465-474 (1986)), Unger, E. C. et al., Invest. Radiol. 20:693-700 (1985)), and Khaw, B. A. et al., Science 209:295-297 (1980)).

The detection of foci of such detectably labeled antibodies might be indicative of a site of tumor development, for example. In one embodiment, this examination is done by removing samples of tissue or blood and incubating such samples in the presence of the detectably labeled antibodies. In a preferred embodiment, this technique is done in a non-invasive manner through the use of magnetic imaging, fluorography, etc. Such a diagnostic test may be employed in monitoring the success of treatment of diseases, where presence or absence of CD38-positive cells is a relevant indicator. The invention also contemplates the use of an anti-CD38 antibody, as described herein for diagnostics in an ex vivo setting.

Therapeutic and Diagnostic Compositions

The antibodies of the present invention can be formulated according to known methods to prepare pharmaceutically useful compositions, wherein an antibody of the invention (including any functional fragment thereof) is combined in a mixture with a pharmaceutically acceptable carrier vehicle. Suitable vehicles and their formulation are described, for example, in REMINGTON'S PHARMACEUTICAL SCIENCES (18th ed., Alfonso R. Gennaro, Ed., Easton, Pa.: Mack Pub. Co., 1990). In order to form a pharmaceutically acceptable composition suitable for effective administration, such compositions will contain an effective amount of one or more of the antibodies of the present invention, together with a suitable amount of carrier vehicle.

Preparations may be suitably formulated to give controlled-release of the active compound. Controlled-release preparations may be achieved through the use of polymers to complex or absorb anti-CD38 antibody. The controlled delivery may be exercised by selecting appropriate macromolecules (for example polyesters, polyamino acids, polyvinyl, pyrrolidone, ethylenevinyl-acetate, methylcellulose, carboxymethylcellulose, or protamine, sulfate) and the concentration of macromolecules as well as the methods of incorporation in order to control release. Another possible method to control the duration of action by controlled release preparations is to incorporate anti-CD38 antibody into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, by coacervation techniques or by interfacial polymerization, for example, hydroxymethylcellulose or gelatine-microcapsules and poly (methylmethacylate) microcapsules, respectively, or in colloidal drug delivery systems, for example, liposomes, albumin microspheres, microemulsions, nanoparticles, and nanocapsules or in macroemulsions. Such techniques are disclosed in Remington's Pharmaceutical Sciences (1980).

The compounds may be formulated for parenteral administration by injection, e.g., by bolus injection or continuous infusion. Formulations for injection may be presented in unit dosage form, e.g., in ampules, or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compositions may, if desired, be presented in a pack or dispenser device, which may contain one or more unit dosage forms containing the active ingredient. The pack may for example comprise metal or plastic foil, such as a blister pack. The pack or dispenser device may be accompanied by instructions for administration.

The invention further is understood by reference to the following working examples, which are intended to illustrate and, hence, not limit the invention.

EXAMPLES

Cell-Lines

The following cell-lines were obtained from the European Collection of Cell Cultures (ECACC), the German Collection of Microorganisms (DSMZ) or the American Type Culture collection (ATCC): hybridoma cell line producing the CD38 mouse IgG1 monoclonal antibody OKT10 (ECACC, #87021903), Jurkat cells (DSMZ, ACC282), LP-1 (DSMZ, ACC41), RPMI8226 (ATCC, CCL-155), HEK293 (ATCC, CRL-1573), CHO-K1 (ATCC, CRL-61) and Raji (ATCC, CCL-86)

Cells and Culture-Conditions

All cells were cultured under standardized conditions at 37° C. and 5% $CO_2$ in a humidified incubator. The cell-lines LP-1, RPMI8226, Jurkat and Raji were cultured in RPMI1640 (Pan biotech GmbH, #P04-16500) supplemented with 10% FCS (PAN biotech GmbH, #P30-3302), 50 U/ml penicillin, 50 µg/ml streptomycin (Gibco, #15140-122) and 2 mM glutamine (Gibco, #25030-024) and, in case of Jurkat- and Raji-cells, additionally 10 mM Hepes (Pan biotech GmbH, #P05-01100) and 1 mM sodium pyruvate (Pan biotech GmbH, #P04-43 100) had to be added.

CHO-K1 and HEK293 were grown in DMEM (Gibco, #10938-025) supplemented with 2 mM glutamine and 10% FCS. Stable CD38 CHO-K1 transfectants were maintained in the presence of G418 (PAA GmbH, P 11-012) whereas for HEK293 the addition of 1 mM sodium-pyruvate was essential. After transient transfection of HEK293 the 10% FCS was replaced by Ultra low IgG FCS (Invitrogen, #16250-078). The cell-line OKT10 was cultured in IDMEM (Gibco, #31980-022), supplemented with 2 mM glutamine and 20% FCS.

Preparation of Single Cell Suspensions from Peripheral Blood

All blood samples were taken after informed consent. Peripheral blood mononuclear cells (PBMC) were isolated by Histopaque®-1077 (Sigma) according to the manufacturer's instructions from healthy donors. Red blood cells were depleted from these cell suspensions by incubation in ACK Lysis Buffer (0.15 M NH4Cl, 10 mM KHCO3, 0.1 M EDTA) for 5 min at RT or a commercial derivative (Bioscience, #00-4333). Cells were washed twice with PBS and then further processed for flow cytometry or ADCC (see below).

Flow Cytometry ("FACS")

All stainings were performed in round bottom 96-well culture plates (Nalge Nunc) with $2 \times 10^5$ cells per well. Cells were incubated with Fab or IgG antibodies at the indicated concentrations in 50 µl FACS buffer (PBS, 3% FCS, 0.02% NaN3) for 40 min at 4° C. Cells were washed twice and then incubated with R-Phycoerythrin (PE) conjugated goat-anti-human or goat-anti-mouse IgG (H+L) F(ab')2 (Jackson Immuno Research), diluted 1:200 in FACS buffer, for 30 min at 4° C. Cells were again washed, resuspended in 0.3 ml FACS buffer and then analyzed by flow cytometry in a FACSCalibur (Becton Dickinson, San Diego, Calif.).

For FACS based Scatchard analyses RPMI8226 cells were stained with at 12 different dilutions (1:2") starting at 12.5 µg/ml (IgG) final concentration. At least two independent measurements were used for each concentration and $K_D$ values extrapolated from median fluorescence intensities according to Chamow et al. (1994).

Surface Plasmon Resonance

The kinetic constants $k_{on}$ and $k_{off}$ were determined with serial dilutions of the respective Fab binding to covalently immobilized CD38-Fc fusion protein using the BIAcore 3000 instrument (Biacore, Uppsala, Sweden). For covalent antigen immobilization standard EDC-NHS amine coupling chemistry was used. For direct coupling of CD38 Fc-fusion protein CM5 sensor chips (Biacore) were coated with ~600-700 RU in 10 mM acetate buffer, pH 4.5. For the reference flow cell a respective amount of HSA (human serum albumin) was used. Kinetic measurements were done in PBS (136 mM NaCl, 2.7 mM KCl, 10 mM $Na_2HPO_4$, 1.76 mM $KH_2PO_4$ pH 7.4) at a flow rate of 20 µl/min using Fab concentration range from 1.5-500 nM. Injection time for each concentration was 1 min, followed by 2 min dissociation phase. For regeneration 5 µl 10 mM HCl was used. All sensograms were fitted locally using BIA evaluation software 3.1 (Biacore).

Example 1

Antibody Generation from HuCAL Libraries

For the generation of therapeutic antibodies against CD38, selections with the MorphoSys HuCAL GOLD phage display library were carried out. HuCAL GOLD® is a Fab library based on the HuCAL® concept (Knappik et al., 2000; Krebs et al., 2001), in which all six CDRs are diversified, and which employs the CysDisplay™ technology for linking Fab fragments to the phage surface (Löbning, 2001).

A. Phagemid Rescue, Phage Amplification and Purification

HuCAL GOLD® phagemid library was amplified in 2×TY medium containing 34 µg/ml chloraunphenicol and 1% glucose (2×TY-CG). After helper phage infection (VCSM13) at an O600 of 0.5 (30 mint 37° C. without shaking; 30 min at 37° C. shaking at 250 rpm), cells were spun down (4120 g; 5 min; 4° C.), resuspended in 2×TY/34 µg/ml chloramphenicol/50 µg/ml kanamycin and grown overnight at 22° C. Phages were PEG-precipitated from the supernatant, resuspended in PBS/20% glycerol and stored at −80° C. Phage amplification between two panning rounds was conducted as follows: mid-log phase TG1 cells were infected with eluted phages and plated onto LB-agar supplemented with 1% of glucose and 34 µg/ml of chloramphenicol (LB-CG). After overnight incubation at 30° C., colonies were scraped off, adjusted to an OD600 of 0.5 and helper phage added as described above.

B. Pannings with HuCAL GOLD®

For the selections HuCAL GOLD® antibody-phages were divided into three pools corresponding to different VH master genes pool 1: VH1/5λκ, pool 2: VH3λκ, pool 3: VH2/4/6λκ). These pools were individually subjected to 3 rounds of whole cell panning on CD38-expressing CHO-K1 cells followed by pH-elution and a post-adsorption step on CD38-negative CHO-K1-cells for depletion of irrelevant antibody-phages. Finally, the remaining antibody phages were used to infect *E. coli* TG1 cells. After centrifugation the bacterial pellet was resuspended in 2×TY medium, plated on agar plates and incubated overnight at 30° C. The selected clones were then scraped from the plates, phages were rescued and amplified. The second and the third round of selections were performed as the initial one.

The Fab encoding inserts of the selected HuCAL GOLD® phages were subcloned into the expression vector pMORPH®x9_Fab_FS (Rauchenberger et al., 2003) to facilitate rapid expression of soluble Fab. The DNA of the selected clones was digested with XbaI and EcoRI thereby cutting out the Fab encoding insert (ompA-VLCL and phoA-Fd), and cloned into the XbaI/EcoRI cut vector pMORPH®x9_Fab_FS. Fab expressed in this vector carry two C-terminal tags (FLAG™ and Strep-Tag® II) for detection and purification.

Example 2

Biological Assays

Antibody dependent cellular cytotoxicity (ADCC) and complement-dependent cytotoxicity was measured according to a published protocol based on flow-cytometry analysis (Naundorf et al., 2002) as follows:
ADCC:

For ADCC measurements, target cells (T) were adjusted to 2.0E+05 cells/ml and labeled with 100 ng/ml Calcein AM (Molecular Probes, C-3099) in RPMI1640 medium (Pan biotech GmbH) for 2 minutes at room temperature. Residual calcein was removed by 3 washing steps in RPMI1640 medium. In parallel PBMC were prepared as source for (natural killer) effector cells (E), adjusted to 1.0E+07 and mixed with the labeled target cells to yield a final B:T-ratio of 50:1 or less, depending on the assay conditions. Cells were washed once and the cell-mix resuspended in 200 µl RPMI1640 medium containing the respective antibody at different dilutions. The plate was incubated for 4 hrs under standardized conditions at 37° C. and 5% $CO_2$ in a humidified incubator. Prior to FACS analysis cells were labeled with propidium-iodide (PI) and analyzed by flow-cytometry (Becton-Dickinson). Between 50.000 and 150.000 events were counted for each assay. The following equation gave rise to the killing activity [in %]:

$$\frac{ED^A}{EL^A + ED^A} \times 100$$

with $ED^A$=events dead cells (calcein+PI stained cells), and $EL^A$=events living cells (calcein stained cells)
CDC:

For CDC measurements, 5.0E+04 CD38 CHO-K1 transfectants were added to a microtiter well plate (Nunc) together with a 1:4 dilution of human serum (Sigma, #S-41 1764) and the respective antibody. All reagents and cells were diluted in RPMI1640 medium (Pan biotech GmbH) supplemented with 10% FCS. The reaction-mix was incubated for 2 firs under standardized conditions at 37° C. and 5% $CO_2$ in a humidified incubator. As negative controls served either heat-inactivated complement or CD38-transfectants without antibody. Cells were labeled with PI and subjected to FACS-analysis.

In total 5000 events were counted and the number of dead cells at different antibody concentrations used for the determination of EC50 values. The following equation gave rise to the killing activity [in %]:

$$\frac{ED^C}{EL^C + ED^C} \times 100$$

with $ED^C$=events dead cells (PI stained cells), and
$EL^C$=events living cells (unstained)
Cytotoxicity values from a total of 12 different antibody-dilutions (1:2") in triplicates were used in ADCC and duplicates in CDC for each antibody in order obtain EC-50 values with a standard analysis software (PRISM®, Graph Pad Software).

Example 3

Generation of Stable CD38-Transfectants and CD38 Fc-Fusion Proteins

In order to generate CD38 protein for panning and screening two different expression systems had to be established. The first strategy included the generation of CD38-Fc-fusion protein, which was purified from supernatants after transient transfection of HEK293 cells. The second strategy involved the generation of a stable CHO-K1-cell line for high CD38 surface expression to be used for selection of antibody-phages via whole cell panning.

As an initial step Jurkat cells (DSMZ ACC282) were used for the generation of cDNA (Invitrogen) followed by amplification of the entire CD38-coding sequence using primers complementary to the first 7 and the last 9 codons of CD38, respectively (primer MTE001 & MTE002rev; Table 4). Sequence analysis of the CD38-unsert confirmed the published amino acid sequence by Jackson et al. (1990) except for position 49 which revealed a glutamune instead of a tyrosine as described by Nata et al. (1997). For introduction of restriction endonuclease sites and cloning into different derivatives of expression vector pcDNA3.1 (Stratagene), the purified PCR-product served as a template for the re-amplification of the entire gene (primers MTE006 & MTE007rev, Table 4) or a part (primers MTE004 & MTE009rev, Table 4) of it. In the latter case a fragment encoding for the extracellular domain (aa 45 to 300) was amplified and cloned in frame between a human Vkappa leader sequence and a human Fc-gamma 1 sequence. This vector served as expression vector for the generation of soluble CD38-Fc fusion-protein. Another pcDNA3.1-derivative without leader-sequence was used for insertion of the CD38 full-length gene. In this case a stop codon in front of the Fc-coding region and the missing leader-sequence gave rise to CD38-surface expression. HEK293 cells were transiently transfected with the Fc-fusion protein vector for generation of soluble CD38 Fc-fusion protein and, in case of the full-length derivative, CHO-K1-cells were transfected for the generation of a stable CD38-expressing cell line.

TABLE 4

| Primer # | Sequence (5'->3') |
| --- | --- |
| MTE001 | ATG GCC AAC TGC GAG TTC AGC (SEQ ID NO: 25) |
| MTE002rev | TCA GAT CTC AGA TGT GCA AGA TGA ATC (SEQ ID NO: 26) |
| MTE004 | TT GGT ACC AGG TGG CGC CAG CAG TG (SEQ ID NO: 27) |
| MTE006 | TT GGT ACC ATG GCC AAC TGC GAG (SEQ ID NO: 28) |
| MTE007rev | CCG ATA TCA\* GAT CTC AGA TGT GCA AGA TG (SEQ ID NO: 29) |
| MTE009rev | CCG ATA TC GAT CTC AGA TGT GCA AGA TG (SEQ ID NO: 30) |

*leading to a stop codon (TGA) in the sense orientation.

Example 4

Cloning, Expression and Purification of HuCAL® IgG1

In order to express full length IgG, variable domain fragments of heavy (VH) and light chains (VL) were subcloned from Fab expression vectors into appropriate pMORPH®_hIg vectors (see FIGS. 8 to 10). Restriction endonuclease pairs BlpI/MfeI (insert-preparation) and BlpI/EcoRI (vector-preparation) were used for subcloning of the VH domain fragment into pMORPH®_hIgG1. Enzyme-pairs EcoRV/HpaI (lambda-insert) and EcoRV/BsiWI (kappa-insert) were used for subcloning of the VL domain fragment into the respective pMORPH®_hIgk_1 or pMORPH®_h_Igλ_1 vectors. Resulting IgG constructs were expressed in HEK293 cells (ATCC CRL-1573) by transient transfection using standard calcium phosphate-DNA coprecipitation technique. IgGs were purified from cell culture supernatants by affinity chromatography via Protein A Sepharose column. Further down stream processing included a buffer exchange by gel filtration and sterile filtration of purified IgG. Quality control revealed a purity of >90% by reducing SDS-PAGE and >90% monomeric IgG as determined by analytical size exclusion chromatography. The endotoxin content of the material was determined by a kinetic LAL based assay (Cambrex European Endotoxin Testing Service, Belgium).

Example 5

Generation and Production of Chimeric OKT10 (chOKT10; SEQ ID NOS: 23 and 24)

For the construction of chOKT10 the mouse VH and VL regions were amplified by PCR using cDNA prepared from the murine OKT10 hybridoma cell line (ECACC #87021903). A set of primers was used as published (Dattamajumdar et al., 1996; Zhou et al., 1994). PCR products were used for Topo-cloning (Invitrogen; pCRII-vector) and single colonies subjected to sequence analysis (M13 reverse primer) which revealed two different kappa light chain sequences and one heavy chain sequence. According to sequence alignments (EMBL-nucleotide sequence database) and literature (Krebber et al, 1997) one of the kappa-sequence belongs to the intrinsic repertoire of the tumor cell fusion partner X63Ag8.653 and hence does not belong to OKT10 antibody. Therefore, only the new kappa sequence and the single VH-fragment was used for further cloning. Both fragments were reamplified for the addition of restriction endonuclease sites followed by cloning into the respective pMORPH® IgGI-expression vectors. The sequences for the heavy chain (SEQ ID NO: 23) and light chain (SEQ ID NO: 24) are given in FIG. 6. HEK293 cells were transfected transiently and the supernatant analyzed in FACS for the chimeric OKT10 antibody binding to the CD38 over-expressing Raji cell line (ATCC).

Example 6

Epitope Mapping

1. Materials and Methods:
Antibodies:
The following anti-CD38 IgGs were sent for epitope mappings:

| MOR# | Lot # | Format | Conc. [mg/ml]/ Vol.[µl] |
|---|---|---|---|
| MOR03077 | 2CHE106_030602 | human IgG1 | 0.44/1500 |
| MOR03079 | 2APO31 | human IgG1 | 0.38/500 |
| M0R03080 | 030116_4CUE16 | human IgG1 | 2.28/200 |
| MORO3100 | 030612_6SBA6 | human IgG1 | 0.39/500 |
| chim. OKT10* | 030603_2CHE111 | human IgG1 | 0.83/500 |

*chimeric OKT10 consisting of human Fc and mouse variable regions.

CD38-Sequence:
The amino acid (aa) sequence (position 44-300) is based on human CD3S taken from the published sequence under SWISS-PROT primary accession number P28907. At position 49 the aa Q (instead of T) has been used for the peptide-design.

PepSpot-Analysis:
The antigen peptides were synthesized on a cellulose membrane in a stepwise manner resulting in a defined arrangement (peptide array) and are covalently bound to the cellulose membrane. Binding assays were performed directly on the peptide array. In general an antigen peptide array is incubated with blocking buffer for several hours to reduce non-specific binding of the antibodies. The incubation with the primary (antigen peptide-binding) antibody in blocking buffer occurs followed by the incubation with the peroxidase (POD)-labelled secondary antibody, which binds selectively the primary antibody. A short T (Tween)-TBS-buffer washing directly after the incubation of the antigen peptide array with the secondary antibody followed by the first chemiluminescence experiment is made to get a first overview which antigen peptides do bind the primary antibody. Several buffer washing steps follow (T-TBS- and TBS-buffer) to reduce false positive binding (unspecific antibody binding to the cellulose membrane itself). After these washing steps the final chemiluminescence analysis is performed. The data were analysed with an imaging system showing the signal intensity (Boehringer Light units, BLU) as single measurements for each peptide. In order to evaluate nonspecific binding of the secondary antibodies (anti-human IgG), these antibodies were incubated with the peptide array in the absence of primary antibodies as the first step. If the primary antibody does not show any binding to the peptides it can be directly labelled with POD, which increases the sensitivity of the system (as performed for MOR3077). In this case a conventional coupling chemistry via free amino-groups is performed. The antigen was scanned with 13-mer peptides (11 amino acids overlap). This resulted in arrays of 123 peptides. Binding assays were performed directly on the array. The peptide-bound antibodies MOR03077, MOR03079, MOR03080, MOR03100 and chimeric OKT10 were detected using a peroxidase-labelled secondary antibody (peroxidase conjugate-goat anti-human IgG, gamma chain specific, affinity isolated antibody; Sigma-Aldrich, A6029). The mappings were performed with a chemiluminescence substrate in combination with an imaging system. Additionally, a direct POD-labelling of MOR03077 was performed in order to increase the sensitivity of the system.

2. Summary and Conclusions:

All five antibodies showed different profiles in the PepSpot analysis. A schematic summary is given in FIG. 7, which illustrates the different aa sequences of CD38 being recognized. The epitope for MOR03079 and chimeric OKT10 can clearly be considered as linear. The epitope for MOR03079 can be postulated within aa 192-206(VSRRFAEAACDV-VHV (SEQ ID NO: 38) of CD38 whereas for chimeric OKT10 a sequence between aa 284 and 298 (FLQCVKN-PEDSSCTS (SEQ ID NO: 39) is recognized predominantly. The latter results confirm the published data for the parental murine OKT10(Hoshino et al., 1997), which postulate its epitope between aa 280-298. Yet, for a more precise epitope definition and determination of key amino acids (main antigen-antibody interaction sites) a shortening of peptides VSR-RFAEAACDVVHV (SEQ ID NO: 38) and FLQCVKN-PEDSSCTS (SEQ ID NO: 39) and an alanine-scan of both should be envisaged.

The epitopes for MOR03080 and MOR03100 can be clearly considered as discontinuous since several peptides covering different sites of the protein sites were recognized. Those peptides comprise aa 82-94 and aa 158-170 for MOR03080 and aa 82-94, 142-154, 158-170, 188-200 and 280-296 for MOR03100. However, some overlaps between both epitopes can be postulated since two different sites residing within aa positions 82-94(CQSVWDAFKGAFI (SEQ ID NO: 40); peptide #20) and 158-170 (TWCGEFNTSKINY (SEQ ID NO: 41); peptide #58) are recognized by both antibodies.

The epitope for MOR03077 can be considered as clearly different from the latter two and can be described as multi-segmented discontinuous epitope. The epitope includes aa 44-66, 110-122, 148-164, 186-200 and 202-224.

Example 7

IL-6-Release/Proliferation Assay

1. Materials and Methods:

Proliferation- and a IL-6 release assays have been performed according to Ausiello et al. (2000) with the following modifications: PBMCs from different healthy donors (after obtaining informed consent) were purified by density gradient centrifugation using the Histopaque cell separation system according to the instructions of the supplier (Sigma) and cultured under standard conditions (5% CO2, 37° C.) in RPMI1640 medium, supplemented with 10% FCS and glutamine ("complete RPMI1640"). For both assays the following antibodies were used: HuCAL® anti-CD38 IgG1s Mabs MOR03077, MOR03079, and MOR03080, an agonistic murine IgG2a monoclonal antibody (IB4; Malavasi et al., 1984), an irrelevant HuCAL® IgG1 antibody, a matched isotype control (murine IgG2a: anti-trinitrophenol, hapten-specific antibody; cat.#: 555571, clone G155-178; Becton Dickinson) or a medium control. For the IL-6 release assay, 1.0 E+06 PBMCs in 0.5 ml complete RPMI1640 medium were incubated for 24 hrs in a 15 ml culture tube (Falcon) in the presence of 20 µg/ml antibodies. Cell culture supernatants were harvested and analysed for IL-6 release using the Quantikine kit according to the manufacturer's protocol (R&D systems). For the proliferation assay 2.0E+05 PBMCs were incubated for 3 days in a 96-well flat bottom plate (Nunc) in the presence of 20 µg/ml antibodies. Each assay was carried out in duplicates. After 4 days BrdU was added to each well and cells incubated for an additional 24 hrs at 37° C. prior to cell fixation and DNA denaturation according to the protocol of the supplier (Roche). Incorporation of BrdU was measured via an anti-BrdU peroxidase-coupled antibody in a chemiluminescence-based setting.

2. Summary and Conclusions:

Proliferation Assay:

In addition to its catalytic activities as a cyclic ADP-ribose cyclase and hydrolase, CD38 displays the ability to transduce signals of biological relevance (Hoshino et al., 1997; Ausiello et al., 2000). Those functions can be induced in vivo by e.g. receptor-ligand interactions or by cross-linking with anti-CD38 antibodies. Those signalling events lead e.g. to calcium mobilization, lymphocyte proliferation and release of cytokines. However, this signalling is not only dependent on the antigenic epitope but might also vary from donor to donor (Ausiello et al., 2000). In the view of immunotherapy non-agonistic antibodies are preferable over agonistic antibodies. Therefore, HuCAL® anti-CD38 antibodies (Mabs MOR03077; MOR03079, MOR03080) were further characterized in a proliferation assay and IL-6- (important MM growth-factor) release assay in comparison to the reference antibody chOKT10 and the agonistic anti-CD38 monoclonal antibody 1B4.

As demonstrated in FIG. 11 and FIG. 12 the HuCAL anti-CD38 antibodies Mab#1, 2 and 3 as well as the reference antibody chOKT10 and corresponding negative controls showed no or only weak induction of proliferation and no IL-6-release as compared to the agonistic antibody IB4.

Example 8

Clonogenic Assay

1. Materials and Methods:

PBMCs harbouring autologous CD34+/CD38+ precursor cells were isolated from healthy individuals (after obtaining informed consent) by density gradient centrifugation using the Histopaque cell separation system according to the instructions of the supplier (Sigma) and incubated with different HuCAL® IgG1 anti-CD38 antibodies (Mabs MOR03077, MOR03079, and MOR03080) and the positive control (PC) chOKT10 at 10 µg/ml. Medium and an irrelevant HuCAL® IgG1 served as background control. Each ADCC-assay consisted of 4.0E+05 PBMCs which were incubated for 4 hrs at 37° C. in RPMI1640 medium supplemented with 10% FCS. For the clonogenic assay 2.50 ml "complete" methylcellulose (CellSystems) was inoculated with 2.5 E+05 cells from the ADCC-assay and incubated for colony-development for at least 14 days in a controlled environment (37° C.; 5% CO2). Colonies were analyzed by two independent operators and grouped into BFU-E+CFU-GEMM (erythroid burst forming units and granulocyte/erythroid/macrophage/megakaryocyte stem cells) and CFU-GM (granulocyte/macrophage stem cells).

2. Summary and Conclusions:

Since CD38-expression is not only found on immune cells within the myeloid (e.g. monocytes, granulocytes) and lymphoid lineage (e.g. activated B and T-cells; plasma cells) but also on the respective precursor cells (CD34+/CD38+), it is important that those cells are not affected by antibody-mediated killing. Therefore, a clonogenic assay was applied in order to analyse those effects on CD34+/CD38+ progenitors.

PBMCs from healthy donors were incubated with HuCAL® anti-CD38 antibodies (Mab#1, Mab#2 and Mab#3) or several controls (irrelevant HuCAL® antibody, medium and reference antibody chOKT10 as positive control) according to a standard ADCC-protocol followed by further incubation in conditioned methylcellulose for colony-development. As shown in FIG. 13 no significant reduction of colony-forming units are shown for all HuCAL® anti-CD38 antibodies as compared to an irrelevant antibody or the reference antibody.

Example 9

ADCC Assays with Different Cell-Lines and Primary Multiple Myeloma Cells

1. Materials and Methods:

Isolation and ADCC of MM-patient samples: Bone marrow aspirates were obtained from multiple myeloma patients (after obtaining informed consent). Malignant cells were purified via a standard protocol using anti-CD138 magnetic beads (Milteny Biotec) after density gradient centrifugation (Sigma). An ADCC-assay was performed as described before.

2. Summary and Conclusions:

Several cell-lines derived from different malignancies were used in ADCC in order to show the cytotoxic effect of the HuCAL® anti-CD38 antibodies on a broader spectrum of cell-lines including different origins and CD38 expression-levels. As shown in FIG. 14, all cells were killed in ADCC at constant antibody concentrations (5 µg/ml) and E:T ratios at 30:1. Cytotoxicity via ADCC was also shown for several multiple myeloma samples from patients. All HuCAL® anti-CD38 antibodies were able to perform a dose-dependent killing of MM-cells and the EC50-values varied between 0.006 and 0.249 nM (FIG. 15).

Example 10

Cross-Reactivity Analysis by FACS and Immunohisto-Chemistry (IHC)

1. Materials and Methods:

IHC with tonsils: For IHC HuCAL® anti-CD38 Mabs and an irrelevant negative control antibody were converted into the bivalent dHLX-format (Plüclethun & Pack, 1997). 5 µm cryo sections from lymph nodes derived from Cynomolgus monkey, Rhesus monkey and humans (retrieved from the archives of the Institute of Pathology of the University of Graz/Austria) were cut with a Leica CM3050 cryostat. Sections were air-dried for 30 minutes to 1 hour and fixed in ice-cold methanol for 10 minutes and washed with PBS. For the detection of the dHLX-format a mouse anti-His antibody (Dianova) in combination with the Envision Kit (DAKO) was used. For the detection of the anti-CD38 mouse antibodies (e.g. reference mouse monoclonal OKT10) the Envison kit was used only.

FACS-analysis of lymphocytes: EDTA-treated blood samples were obtained from healthy humans (after obtaining informed consent), from Rhesus and Cynomolgus monkeys and subjected to density gradient centrifugation using the Histopaque cell separation system according to the instructions of the supplier (Sigma). For FACS-analysis cells from the interphase were incubated with primary antibodies (HuCAL® anti-CD38 and negative control Mabs as murine IgG2a or Fab-format, the positive control murine antibody OKT10 and a matched isotype control) followed by incubation with anti-M2 Flag (Sigma; only for Fab-format) and a phycoerythrin (PE)-labeled anti-mouse conjugate (Jackson Research). FACS analysis was performed on the gated lymphocyte population.

2. Summary and Conclusions:

HuCAL® anti-CD38 were analyzed for inter-species CD3S cross-reactivity. Whereas all anti-CD38 Mabs were able to detect human CD38 on lymphocytes in FACS and IHC, only MOR03080 together with the positive control OKT10 showed an additional reactivity with Cynomolgus and Rhesus monkey CD38 (see Table 5: Cross-reactivity analysis).

TABLE 5

| | Lymphocytes (FACS) and lymph-nodes (IHC) from: | | |
|---|---|---|---|
| Antibody | Human | Cynomolgus Monkey | Rhesus Monkey |
| Mab#1 | ++ | − | − |
| Mab#2 | ++ | − | − |
| Mab#3 | ++ | ++ | ++ |
| PC | ++ | ++ | ++ |
| NC | − | − | − |

++: strong positive staining;
−: no staining;
NC: negative control;
PC: positive control (=reference cMAb)

Example 11

Treatment of Human Myeloma Xenografts in Mice (Using the RPM18226 Cell Line) with MOR03080

1. Establishment of Subcutaneous Mouse Model:

A subcutaneous mouse model for the human myeloma-derived tumor cell line RPMI8226 in female C.B-17-SCID mice was established as follows by Aurigon Life Science GmbH (Tutzing, Germany): on day −1, 0, and 1, anti-asialo GM1 polyclonal antibodies (ASGM) (WAKO-Chemicals), which deplete the xenoreactive NK-cells in the SCID mice were applied intravenously in order to deactivate any residual specific immune reactivity in C.B-17-SCID mice. On day 0, either $5 \times 10^6$ or $1 \times 10^7$ RPMI8226 tumor cells in 50 µl PBS were inoculated subcutaneously into the right flank of mice either treated with ASGM (as described above) or untreated (each group consisting of five mice). Tumor development was similar in all 4 inoculated groups with no significant difference being found for treatment with or without anti-asialo GM1 antibodies or by inoculation of different cell numbers. Tumors appear to be slowly growing with the tendency of stagnation or oscillation in size for some days. Two tumors oscillated in size during the whole period of investigation, and one tumor even regarded and disappeared totally from a peak volume of 321 mm³. A treatment study with this tumor model should include a high number of tumor-inoculated animals per group.

2. Treatment with MOR03080:

2.1 Study Objective

This study was performed by Aurigon Life Science GmbH (Tutzing, Germany) to compare the anti-tumor efficacy of intraperitoneally applied antibodies (HuCAL® anti-CD38) as compared to the vehicle treatment (PBS). The human antibody hMOR03080 (isotype IgG1) was tested in different amounts and treatment schedules. In addition the chimeric antibody chMOR03080 (isotype IgG2a: a chimeric antibody comprising the variable regions of MOR03080 and murine constant regions constructed in a similar way as described in Example 5 for chimeric OKT10 (murine VH/VL and human constant regions)) was tested. The RPMI8226 cancer cell line had been chosen as a model and was inoculated subcutaneously in female SCID mice as described above. The endpoints in the study were body weight (b.w.), tumor volume and clinical signs.

2.2 Antibodies and Vehicle

The antibodies were provided ready to use to Aurigon at concentrations of 2.13 mg/ml (MOR03080 hIgG1) and 1.73 mg/ml (MOR03080 chIgG2a, and stored at −80° C. until application. The antibodies were thawed and diluted with PBS to the respective end concentration. The vehicle (PBS) was provided ready to use to Aurigon and stored at 4° C. until application.

2.3 Animal Specification
  Species: mouse
  Strain: Fox chase C.B-17-scid (C.B-Igh-lb/IcrTac)
  Number and sex: 75 females
  Supplier: Taconic M&B, Bomholtvej 10, DK-8680 Ry
  Health status: SPF
  Weight ordered: appr. 18 g
  Acclimatization: 9 days 2.4 Tumor Cell Line The tumor cells (RPMI8226 cell line) were grown and transported to Aurigon Life Science GmbH, where the cells were splitted and grown for another cycle. Aurigon prepared the cells for injection on the day of inoculation. The culture medium used for cell propagation was RPMI 1640 supplemented with 5% FCS, 2 mM L-Glutamin and PenStrep. The cells showed no unexpected growth rate or behaviour.

For inoculation, tumor cells were suspended in PBS and adjusted to a final concentration of $1\times10^7$ cells/50 µl in PBS. The tumor cell suspension was mixed thoroughly before being injected.

2.5 Experimental Procedure

On day 0, $1\times10^7$ RPMI8226 tumor cells were inoculated subcutaneously into the right dorsal flank of 75 SCID mice. A first group was built with 15 randomly chosen animals (group 5) directly after inoculation. This group was treated with 1 mg/kg b.w. hIgG11-MOR03080 every second day between day 14 and 36. From all other 60 animals 4 groups were built with ten animals in each group on day 31 (tumor volume of about 92 mm$^3$). Groups 1-4 were built with comparable means tumor sizes and standard deviations. An additional group of 5 animals (group 6) was chosen showing relatively small tumor volumes (tumor volume of about 50 mm$^3$) for comparison with pre-treated group 5 (all but three mice showing tumor volumes of less than 10 mm$^3$, one with about 22 mm$^3$, one with about 44 mm$^3$ and one with about 119 mm$^3$). Groups 1 to 4 were treated every second day from day 32 to day 68 with either PBS (Vehicle; group 1), 1 mg/kg b.w. hIgG1-MOR03080 (group 2) or 5 mg/kg b.w.hIgG1-MOR03080 (group 3), or with 5 mg/kg b.w. chIgG2a-MOR03080 (group 4). Group 6 did not receive any treatment (see Table 6). Tumor volumes, body weight and clinical signs were measured two times a week until end of study.

TABLE 6

| Group | No. of animals | Type of application | Substance | Schedule | Treatment dose [mg/kg] | Appl. volume [µl/kg] |
|---|---|---|---|---|---|---|
| 1 | 10 | i.p. | vehicle (PBS) | every second day between day 32 and day 68 | — | 10 |
| 2 | 10 | i.p. | MOR03080 human IgG1 | every second day between day 32 and day 68 | 1 | 10 |
| 3 | 10 | i.p. | MOR03080 human IgG1 | every second day between day 32 and day 68 | 5 | 10 |
| 4 | 10 | i.p. | MOR03080 chimeric IgG2a | every second day between day 32 and day 68 | 5 | 10 |
| 5 | 15 | i.p. | MOR03080 human IgG1 | every second day between day 14 and day 36 | 1 | 10 |
| 6 | 5 | — | — | — | — | — |

2.6 Results

Clinical Observations and Mortality

No specific tumor or substance related clinical findings or mortality were observed. In group 3 (hIgG1 5 mg/kg) four animals died during blood sampling (one on day 3, one on day 34; two on day 52). In group 4 (muIgG2a 1 mg/kg) a single animal died during blood sampling (day 34). All other animals, that died during the study have been euthanized because of the tumor size.

Body Weight Development

No drug related interference with weight development was observed in comparison to group 1 (vehicle). Body weight was markedly influenced by blood sampling in groups 3 (hIgG1 5 mg/kg) and 4 (muIgG2a 5 mg/kg). Despite such interruptions the mean weight gain of all groups was continuous.

Tumor Development (See FIG. 16)

In group 1 (vehicle) tumor growth was found in the expected rate with a slow progression. As this cell line has a pronounced standard deviation values for the largest and smallest tumor have been excluded from further statistical analysis. The tumor growth of animals in group 1 was comparable to the tumor growth in group 6 (untreated), although this group started with a lower mean tumor volume on day 31. Treatment might therefore have a slight influence on the tumor growth rate. In group 1, two mice had to be euthanized before day 83 because of the tumor size, and a further one before day 87, so that the mean value of tumor volume is no longer representative after day 80. In group 6, one mouse had to be euthanized before day 80 because of the tumor size, two mice before day 83, and a further one before day 87, so that the mean value of tumor volume is no longer representative after day 76.

In group 2, treated with 1 mg/kg b.w. of hIgG1, one animal has been excluded from further analysis, because the tumor grew into the muscular tissue and this usually enhances the speed of tumor growth. Compared with the control group 1 (vehicle) the mean tumor size started to differ significantly starting with day 45 until the end of the study. No enhanced tumor growth was observed after end of treatment (day 68).

Animals of group 3 (5 mg/kg b.w. hIgG1) revealed a marked decrease in tumor growth in comparison to group 1 (vehicle), getting statistically significant with day 38 until day 83. The mean tumor volume started to strongly regrow about two weeks after the end of treatment. One out of ten tumors disappeared at day 45 and did not regrow up to 19 days after end of treatment.

The best performance of all treatment groups starting with 92 mm$^3$ tumor volume was found in group 4 (5 mg/kg b.w. muIgG2a), where the mean tumor volume showed clear regression and tumors even disappeared in 4 animals until the end of the observation period. The difference to the mean tumor volume of group 1 (vehicle) was highly significant beginning from day 38 until the end of study.

The early treatment with 1 mg/kg b.w. hIgG1 between days 14 and 36 (group 5) revealed an early as well as long lasting effect on tumor development. One animal has been excluded from further analysis as the tumor grew into muscular tissue. On day 31, only five animals had a measurable tumor at the site of inoculation, in comparison to the rest of the inoculated animals, where only 2 out of 60 did not respond to tumor inoculation. The tumor progression was delayed of about 31 days (comparison of day 52 of control group 1 with day 83 of group 5). About 50% of the animals did not show tumors at the site of inoculation at the end of the study.

2.7 Conclusion

No specific tumor or substance related clinical findings or mortality were observed in comparison with group 1 (control).

No drug related interference with weight development was observed.

Tumor growth of RPMI8226 tumor cells after treatment was reduced in the order of efficiency: hIgG1 1 mg/kg, 14-36 days every second day (group 5)>muIgG2a 5 mg/kg 32-68 days every second day (group 4)>hIgG1 5 mg/kg 32-68 days every second day (group 3)>hIgG1 1 mg/kg 32-68 days every second day (group 2). In groups 2 to 4, mean tumor volumes were again increased after end of treatment to varying extents.

REFERENCES

Ausiello C. M., Urbani F., Lande R., la Sala A., Di Carlo B., Baj G., Surico N., Hilgers J., Deaglio S., Funaro A., Malavasi F. (2000) Functional topography of discrete domains of human CD38. Tissue Antigens. 2000 December; 56(6): 539-47.

Chamow, S. M., Zhang, D. Z., Tan, X. Y, Mathre, S. M., Marsters, S. A., Peers, D. H., Byrn, R. A., Ashknazi, A., Junghans, R. P (1994). humanized, bispecific immunoadhesin-antibody that retargets CD3+ effectors to kill HIV-1-infected cells. J Immunol. 1994 Nov. 1; 153(9):4268-80

Dattamajumdar, A. K., Jacobsen, D. P., Hood, L. E., Osman, G. E. (1996). Rapid cloning of rearranged mouse inimunoglobulin variable genes. Immunogentetics 43, 141-151

Funaro, A., Spagnoli, G. C., Ausiello, C. M., Alessio, M., Roggero, S., Delia, D., Zaccolo, M., and Malavasi, F. (1990) Involvement of the multilineage CD38 molecule in a unique pathway of cell activation and proliferation. J. Immunol. 145, 2390-2396.

Hoshino S., Kukimoto I., Kontani K., Inoue S., Kanda Y., Malavasi F., Katada T. (1997) Mapping of the catalytic and epitopic sites of human CD38/NAD+glycohydrolase to a functional domain in the carboxyl terminus. J Immunol. 158(2):741-7.

Jackson D. G., Bell J. I. (1990) Isolation of a cDNA encoding the human CD38 (T10) molecule, a cell surface glycoprotein with an unusual discontinuous pattern of expression during lymphocyte differentiation. J Immunol. 144(7):2811-5.

Knappik, A., Ge, L., Honegger, A., Pack, P., Fischer, M., Wellnhofer, G., Hoess, A., Wolle, J., Piuckthun, A., and Virnekas, B. (2000). Fully synthetic human combinatorial antibody libraries (HuCAL) based on modular consensus frameworks and CDRs randomized with trinucleotides. J Mol Biol 296, 57-86.

Konopleva M., Estrov Z., Zhao S., Andreeff M., Mehta K. (1998) Ligation of cell surface CD38 protein with agonistic monoclonal antibody induces a cell growth signal in myeloid leukemia cells. J Immunol. 161(9):4702-8.

Krebber, A., Bornhauser, S., Burmester, J., Honegger, A., Willuda, J., Bossard, H. R., Plückthun, A. (1997). Reliable cloning of functional antibody variable domains from hybridomas and spleen cell repertoires employing a reengineered phage display system. J. Imm. Meth. 201, 35-55.

Krebs, B., Rauchenberger, R., Reiffert, S., Rothe, C., Tesar, M., Thomassen, E., Cao, M., Dreier, T., Fischer, D., Hoss, A., Inge, L., Knappik, A., Marget, M., Pack, P., Meng, X. Q., Schier, R., Soblemann, P., Winter, J., Wolle, J., and Kretzschmar, T. (2001). Highthroughput generation and engineering of recombinant human antibodies. J Immunol. Methods 254, 67-84.

Löhning, C. (2001). Novel methods for displaying (poly) peptides/proteins on bacteriophage particles via disulfide bonds. WO 01/05950.

Malavasi, F., Caligaris-Cappio, F., Milanese, C., Dellabona, P., Richiardi, P., Carbonara, A. O. (1984). Characterization of a murine monoclonal antibody specific for human early lymphohemopoietic cells. Hum. Immunol. 9: 9-20

Namba, M., Otsuki, T., Mori, M., Togawa, A., Wada, H., Sugihara, T., Yawata, Y., Kimoto, T. (1989). Establishment of five human myeloma cell lines. In Vitro Cell Dev. Biol. 25: 723.

Nata K., Takarnura T., Karasawa T., Kumagai T., Hashioka W., Tohgo A., Yonekura H., Takasawa S., Nakamura S., Okamoto H. (1997). Human gene encoding CD38 (ADP-ribosyl cyclase/cyclic ADP-ribose hydrolase): organization, nucleotide sequence and alternative splicing. Gene 186(2):285-92.

Naundorf, S., Preithner, S., Mayer, P., Lippold, S., Wolf, A., Hanakam, F., Fichtner, I., Kufer, P., Raum, T., Riethmüller, G., Baeuerle, P. A., Dreier, T. (2002). Int. J. Cancer 100, 101-110.

Plückthun A, and Pack P. (1997) New protein engineering approaches to multivalent and bispecific antibody fragments. Immunotechnology 3(2):83-105.

Rauchenberger R., Borges B., Thomassen-Wolf E., Rom E., Adar R., Yaniv Y., Malka M., Chumakov I., Kotzer S., Resnitzky D., Knappik A., Reiffert S., Prassler J., Jury K., Waldherr D., Bauer S., Kretzschmar T., Yayon A., Rothe C. (2003). Human combinatorial Fab library yielding specific and functional antibodies against the human fibroblast growth factor receptor 3. J Biol Chem. 278(40):38194-205.

Zhou, H., Fisher, R. J., Papas, T. S. (1994). Optimization of primer sequences for mouse scFv repertoire display library construction. Nucleic Acids Res. 22: 888-889.

The invention claimed is:

1. An isolated human antibody that specifically binds an epitope of CD38 (SEQ ID NO: 22),
  wherein said antibody mediates killing of a CD38+ target cell by antibody dependent cellular cytotoxicity with at least five-fold better efficacy than chimeric OKT10 antibody (SEQ ID NOS: 23 and 24) under the same or substantially the same conditions when a human PBMC cell is employed as the effector cell,
  wherein said CD38+ target cell is selected from the group consisting of LP-1 (DSMZ: ACC41) and RPMI-8226 (ATCC: CCL-155), and
  wherein the ratio of effector cells to target cells is between about 30:1 and about 50:1.

2. An isolated antibody according to claim 1, comprising an H-CDR1, H-CDR2 and H-CDR3 depicted in SEQ ID NO: 5 and an L-CDR1, L-CDR2 and L-CDR3 depicted in SEQ ID NO: 13.

3. An isolated antibody according to claim 1, comprising an H-CDR1, H-CDR2 and H-CDR3 depicted in SEQ ID NO: 6 and an L-CDR1, L-CDR2 and L-CDR3 depicted in SEQ ID NO: 14.

4. An isolated antibody according to claim 1, comprising an H-CDR1, H-CDR2 and H-CDR3 depicted in SEQ ID NO: 7 and an L-CDR1, L-CDR2 and L-CDR3 depicted in SEQ ID NO: 15.

5. An isolated antibody according to claim 1, comprising an H-CDR1, H-CDR2 and H-CDR3 depicted in SEQ ID NO: 8 and an L-CDR1, L-CDR2 and L-CDR3 depicted in SEQ ID NO: 16.

6. An isolated antibody to according to claim 1, which is an IgG.

7. An isolated antibody to according to claim 6, which is an IgG1.

8. An isolated human antibody that specifically binds to an epitope of CD38 (SEQ ID NO: 22),
  wherein said antibody mediates killing of a CD38-transfected CHO cell by cell dependent cytotoxicity with at least two-fold better efficacy than chimeric OKT10 antibody (SEQ ID NOS: 23 and 24) under the same or substantially the same conditions.

9. An isolated antibody according to claim 8, comprising an H-CDR1, H-CDR2 and H-CDR3 depicted in SEQ ID NO: 5 and an L-CDR1, L-CDR2 and L-CDR3 depicted in SEQ ID NO: 13.

10. An isolated antibody according to claim 8, comprising an H-CDR1, H-CDR2 and H-CDR3 depicted in SEQ ID NO: 6 and an L-CDR1, L-CDR2 and L-CDR3 depicted in SEQ ID NO: 14.

11. An isolated antibody according to claim 8, comprising an H-CDR1, H-CDR2 and H-CDR3 depicted in SEQ ID NO: 7 and an L-CDR1, L-CDR2 and L-CDR3 depicted in SEQ ID NO: 15.

12. An isolated antibody to according to claim 8, which is an IgG.

13. An isolated antibody to according to claim 12, which is an IgG1.

14. An isolated human or humanized antibody or antibody fragment thereof containing an antigen-binding region which specifically binds within amino acids 44 to 206 of CD38 (SEQ ID NO: 22).

15. An isolated antibody or antibody fragment thereof containing an antigen-binding region of claim 14, which specifically binds within amino acids 44-66, 82-94, 142-154, 148-164, 158-170, or 192-206 of CD38 (SEQ ID NO: 22).

16. An isolated antibody or antibody fragment thereof containing an antigen-binding region of claim 15, which specifically binds within amino acids 44-66 or 148-164 of CD38 (SEQ ID NO: 22).

17. An isolated antibody or antibody fragment thereof containing an antigen-binding region of claim 16, which specifically binds within amino acids 44-66 and 148-164 of CD38 (SEQ ID NO: 22).

18. An isolated antibody or antibody fragment thereof containing an antigen-binding region of claim 15, which specifically binds within amino acids 192-206 of CD38 (SEQ ID NO: 22).

19. An isolated antibody or antibody fragment thereof containing an antigen-binding region of claim 15, which specifically binds within amino acids 82-94 or 158-170 of CD38 (SEQ ID NO: 22).

20. An isolated antibody or antibody fragment thereof containing an antigen-binding region of claim 19, which specifically binds within amino acids 82-94 and 158-170 of CD38 (SEQ ID NO: 22).

21. An isolated antibody or antibody fragment thereof containing an antigen-binding region of claim 15, which specifically binds within amino acids 82-94 or 142-154 of CD38 (SEQ ID NO: 22).

22. An isolated antibody or antibody fragment thereof containing an antigen-binding region of claim 21, which specifically binds within amino acids 82-94 and 142-154 of CD38 (SEQ ID NO: 22).

23. An isolated antibody or antibody fragment thereof containing an antigen-binding region according to claim 14, comprising an H-CDR1, H-CDR2 and H-CDR3 depicted in SEQ ID NO: 5 and an L-CDR1, L-CDR2 and L-CDR3 depicted in SEQ ID NO: 13.

24. An isolated antibody or antibody fragment thereof containing an antigen-binding region according to claim 14, comprising an H-CDR1, H-CDR2 and H-CDR3 depicted in SEQ ID NO: 6 and an L-CDR1, L-CDR2 and L-CDR3 depicted in SEQ ID NO: 14.

25. An isolated antibody or antibody fragment thereof containing an antigen-binding region according to claim 14, comprising an H-CDR1, H-CDR2 and H-CDR3 depicted in SEQ ID NO: 7 and an L-CDR1, L-CDR2 and L-CDR3 depicted in SEQ ID NO: 15.

26. An isolated antibody or antibody fragment thereof containing an antigen-binding region according to claim 14, comprising an H-CDR1, H-CDR2 and H-CDR3 depicted in SEQ ID NO: 8 and an L-CDR1, L-CDR2 and L-CDR3 depicted in SEQ ID NO: 16.

27. An isolated antibody according to claim 14, which is an IgG.

28. An isolated antibody according to claim 27, which is an IgG1.

\* \* \* \* \*

UNITED STATES PATENT AND TRADEMARK OFFICE
CERTIFICATE OF CORRECTION

PATENT NO. : 8,263,746 B2
APPLICATION NO. : 10/588568
DATED : September 11, 2012
INVENTOR(S) : Michael Tesar and Ute Jaeger It is certified that error appears in the above-identified patent and that said Letters Patent is hereby corrected as shown below:

In the claims

Col. 67, line 32, claim 1, "(SEQ ID NOS: 23 and 24)" should read -- (encoded by SEQ ID NOS: 23 and 24) --

Col. 67, line 67, claim 8, "(SEQ ID NOS: 23 and 24)" should read -- (encoded by SEQ ID NOS: 23 and 24) --

Col. 67, line 64, claim 8, "CHO cell by cell dependent cytotoxicity" should read -- CHO cell by complement dependent cytotoxicity --

Signed and Sealed this
Fifteenth Day of March, 2016

Michelle K. Lee
*Director of the United States Patent and Trademark Office*